United States Patent
Byzova et al.

(10) Patent No.: US 9,592,269 B2
(45) Date of Patent: Mar. 14, 2017

(54) COMPOUNDS AND METHODS OF MODULATING ANGIOGENESIS

(71) Applicants: THE CLEVELAND CLINIC FOUNDATION, Cleveland, OH (US); CASE WESTERN RESERVE UNIVERSITY, Cleveland, OH (US)

(72) Inventors: Tatiana Byzova, Pepper Pike, OH (US); Ganapati H. Mahabaleshwar, Cleveland, OH (US); Weiyi Feng, Woodmere, OH (US)

(73) Assignee: The Cleveland Clinic Foundation, Cleveland, OH (US)

( * ) Notice: Subject to any disclaimer, the term of this patent is extended or adjusted under 35 U.S.C. 154(b) by 0 days.

(21) Appl. No.: 14/937,289

(22) Filed: Nov. 10, 2015

(65) Prior Publication Data

US 2016/0101151 A1   Apr. 14, 2016

Related U.S. Application Data

(63) Continuation of application No. 13/175,132, filed on Dec. 14, 2012, now Pat. No. 9,180,164.

(60) Provisional application No. 61/570,433, filed on Dec. 14, 2011.

(51) Int. Cl.
*A61K 38/17* (2006.01)
*A61K 38/18* (2006.01)
*A61K 38/08* (2006.01)
*A61K 38/10* (2006.01)

(52) U.S. Cl.
CPC ............ *A61K 38/179* (2013.01); *A61K 38/08* (2013.01); *A61K 38/10* (2013.01); *A61K 38/1709* (2013.01); *A61K 38/1777* (2013.01)

(58) Field of Classification Search
CPC ..................... A61K 38/1777; A61K 38/179
See application file for complete search history.

(56) References Cited

U.S. PATENT DOCUMENTS

| 8,080,252 B2* | 12/2011 | Byzova | C07K 14/70553 424/185.1 |
| 9,180,164 B2* | 11/2015 | Byzova | A61K 38/179 |
| 2009/0298769 A1* | 12/2009 | Byzova | C07K 14/70553 514/1.1 |

\* cited by examiner

*Primary Examiner* — Ruixiang Li
(74) *Attorney, Agent, or Firm* — Tarolli, Sundheim, Covell & Tummino LLP

(57) ABSTRACT

A pharmaceutical composition includes a synthetic peptide consisting of about 10 to about 50 amino acids and having an amino acid sequence substantially homologous to consecutive amino acids of a portion of the cytoplasmic domain of at least one of $\alpha_v\beta_3$ integrin or VEGFR2 that includes a tyrosine residue, the amino acid sequence of the peptide including a phosphorylated tyrosine residue or a γ-carboxyglutamic acid residue that is substituted for a corresponding tyrosine residue of the portion of the cytoplasmic domain of $\alpha_v\beta_3$ integrin or VEGFR2.

1 Claim, 23 Drawing Sheets

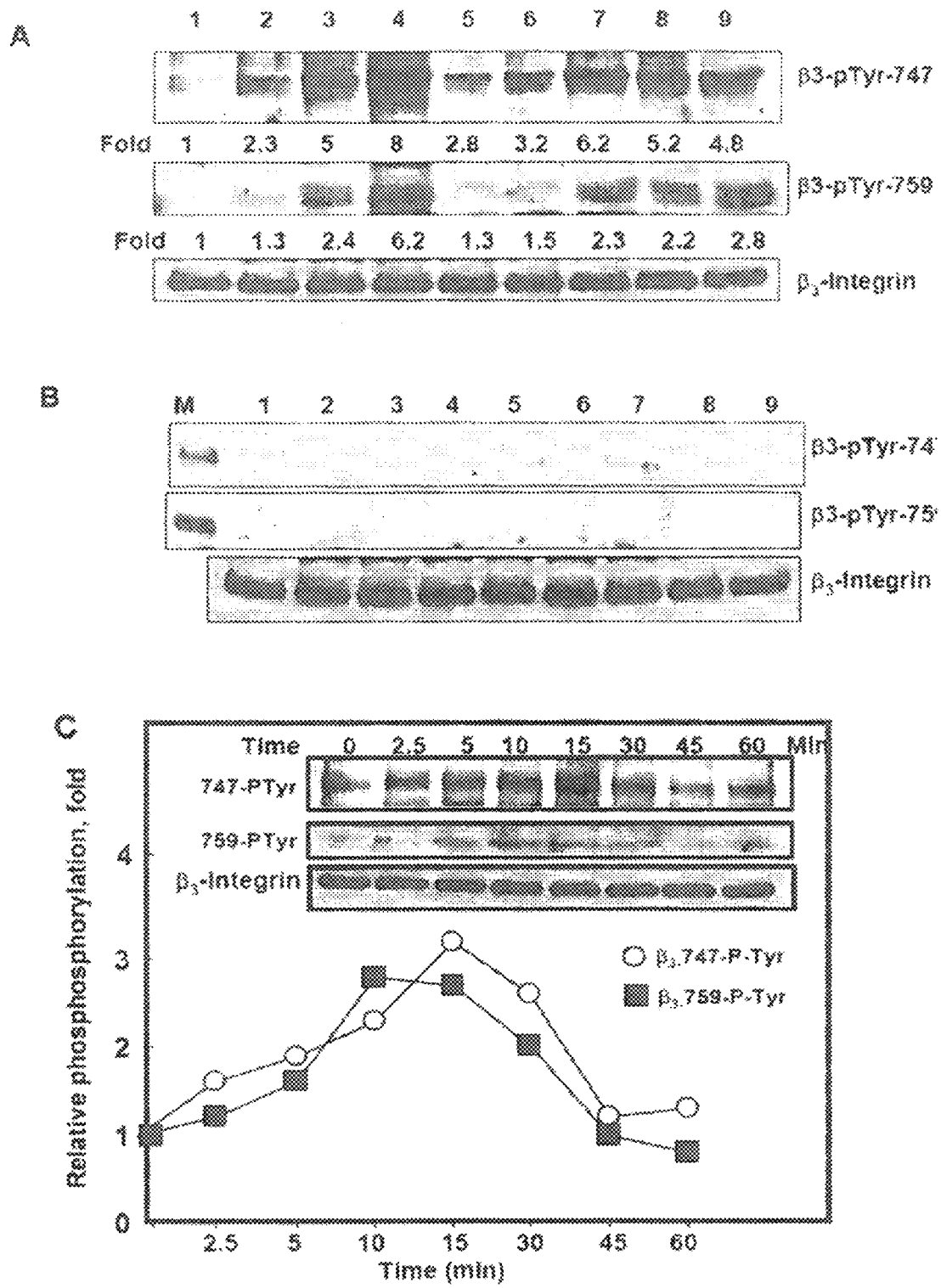
FIGS. 1A-C

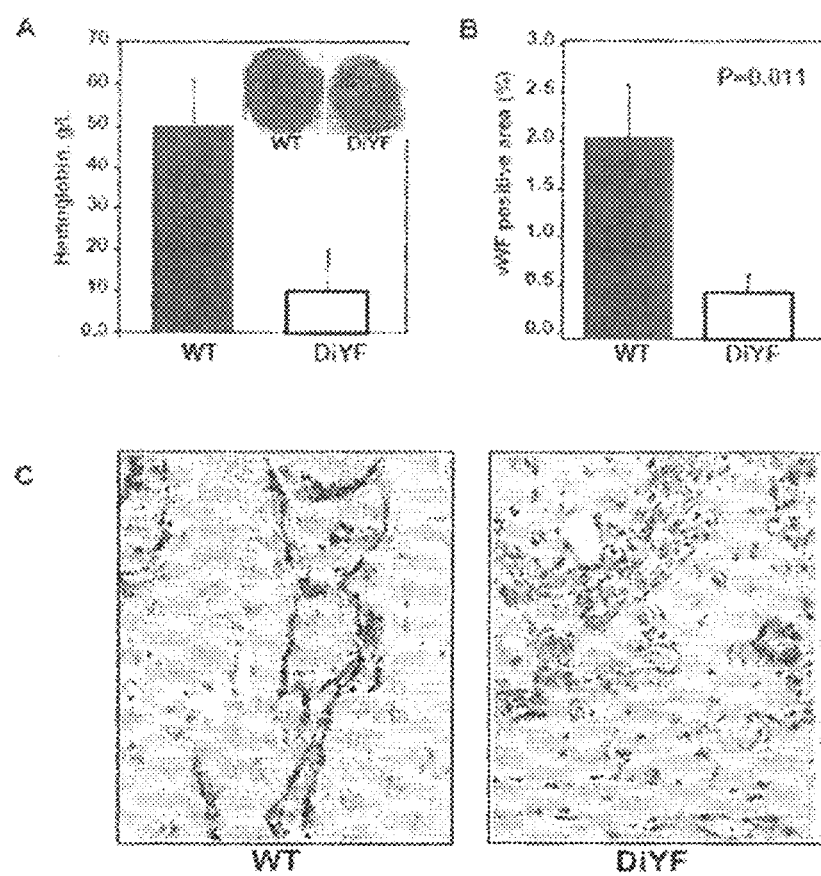
Figs. 2A-C

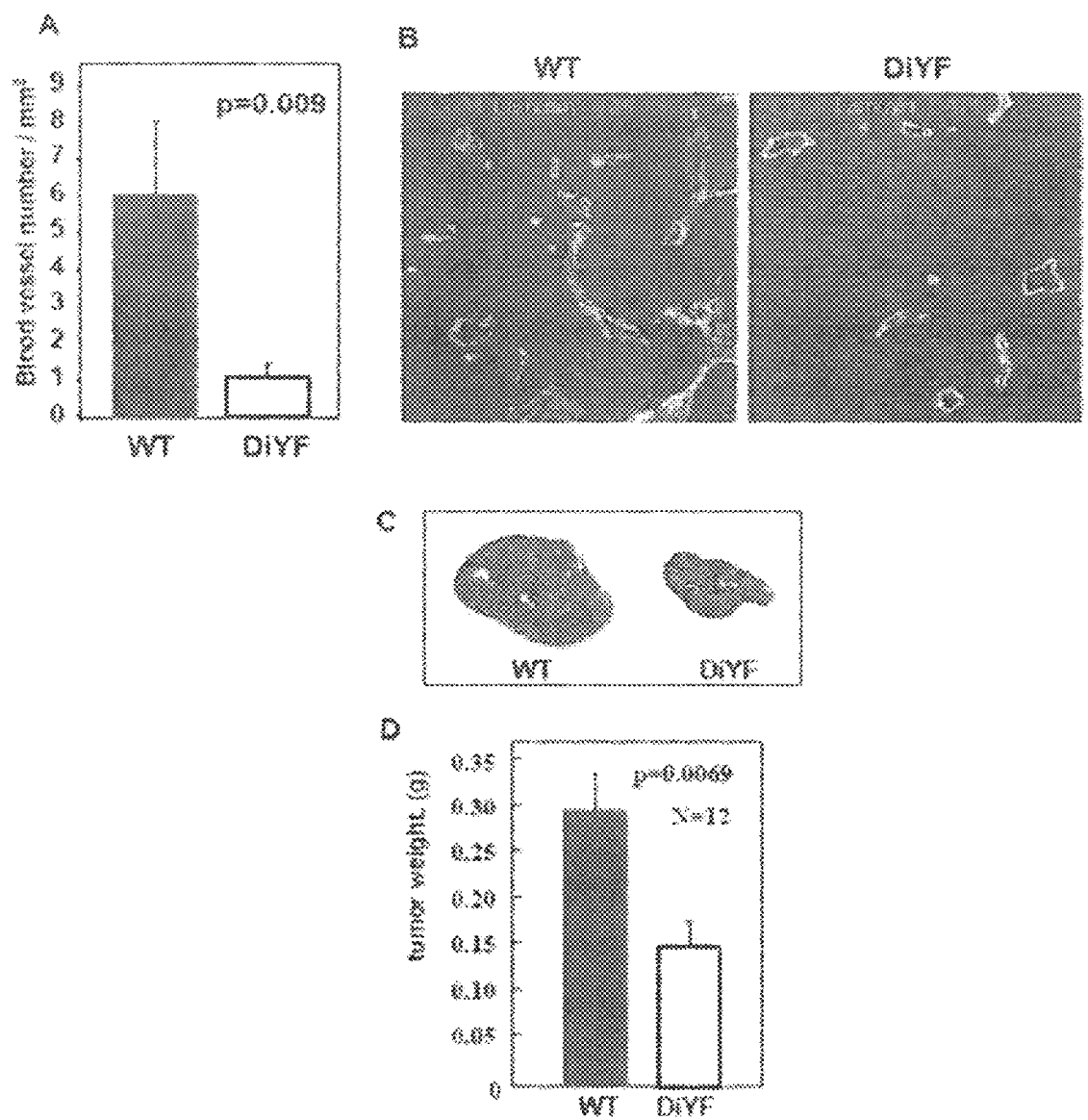
FIGS. 3A-D

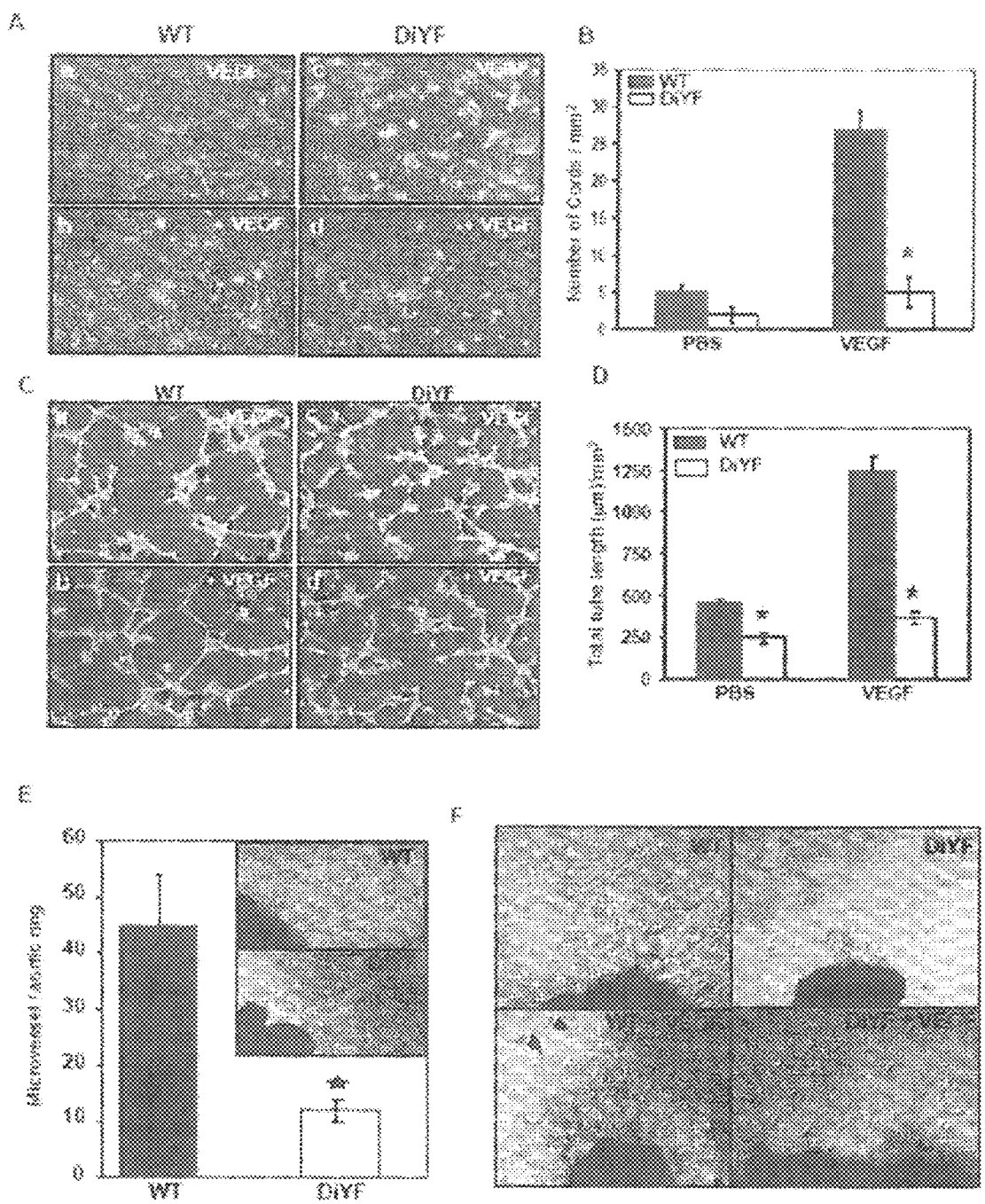
FIGS. 4A-F

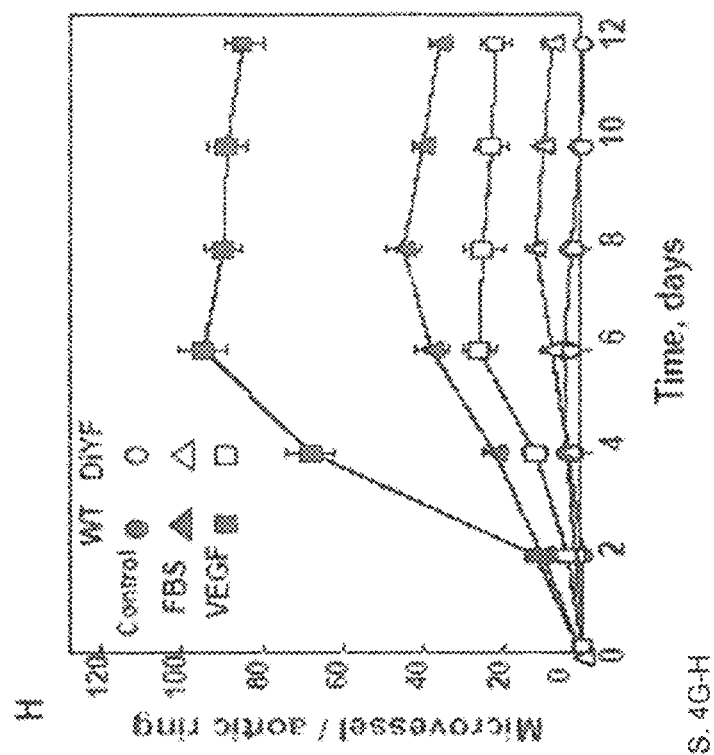
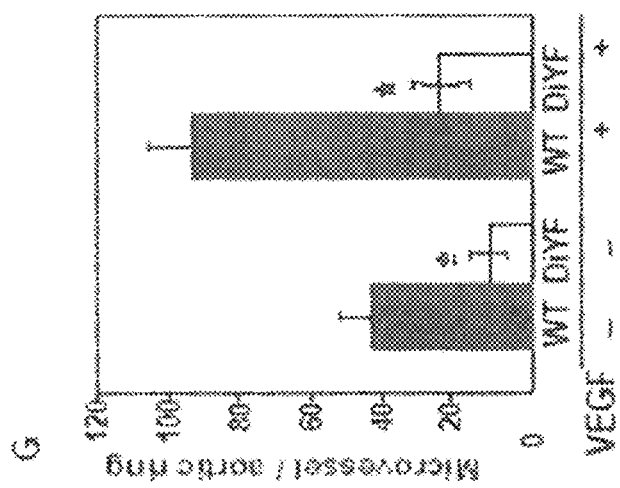
FIGS. 4G-H

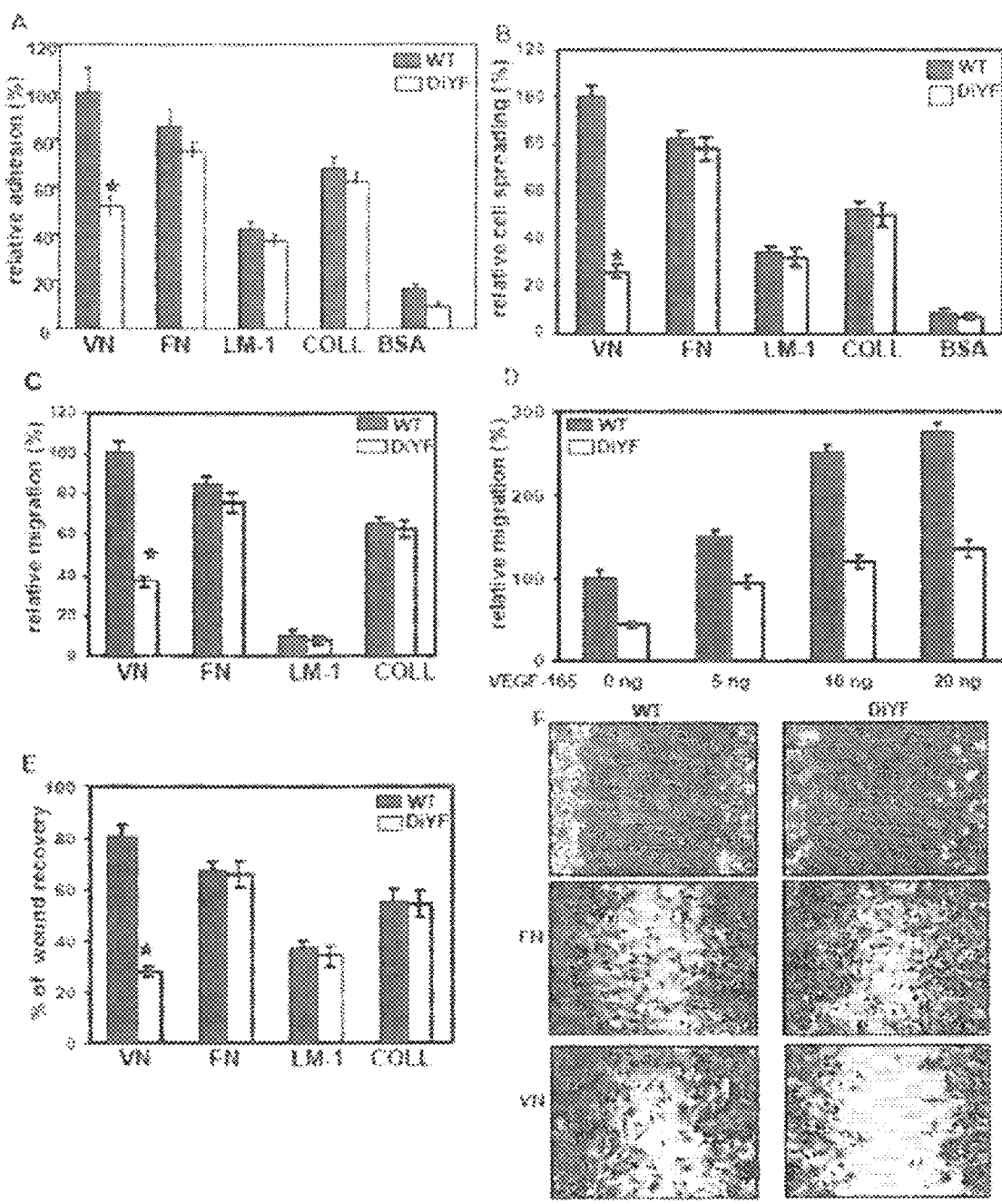
FIGS. 5A-F

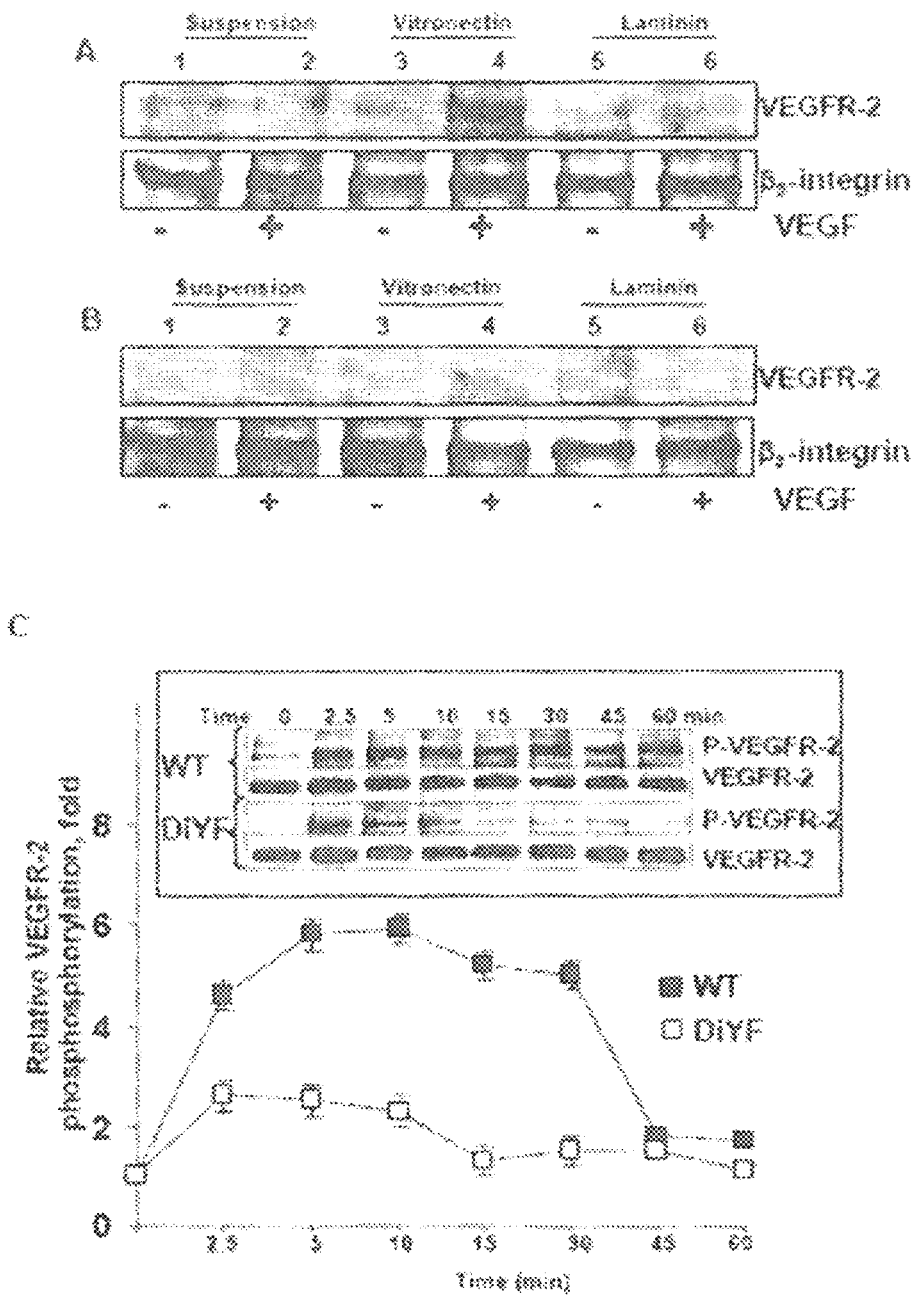
FIGS. 6A-C

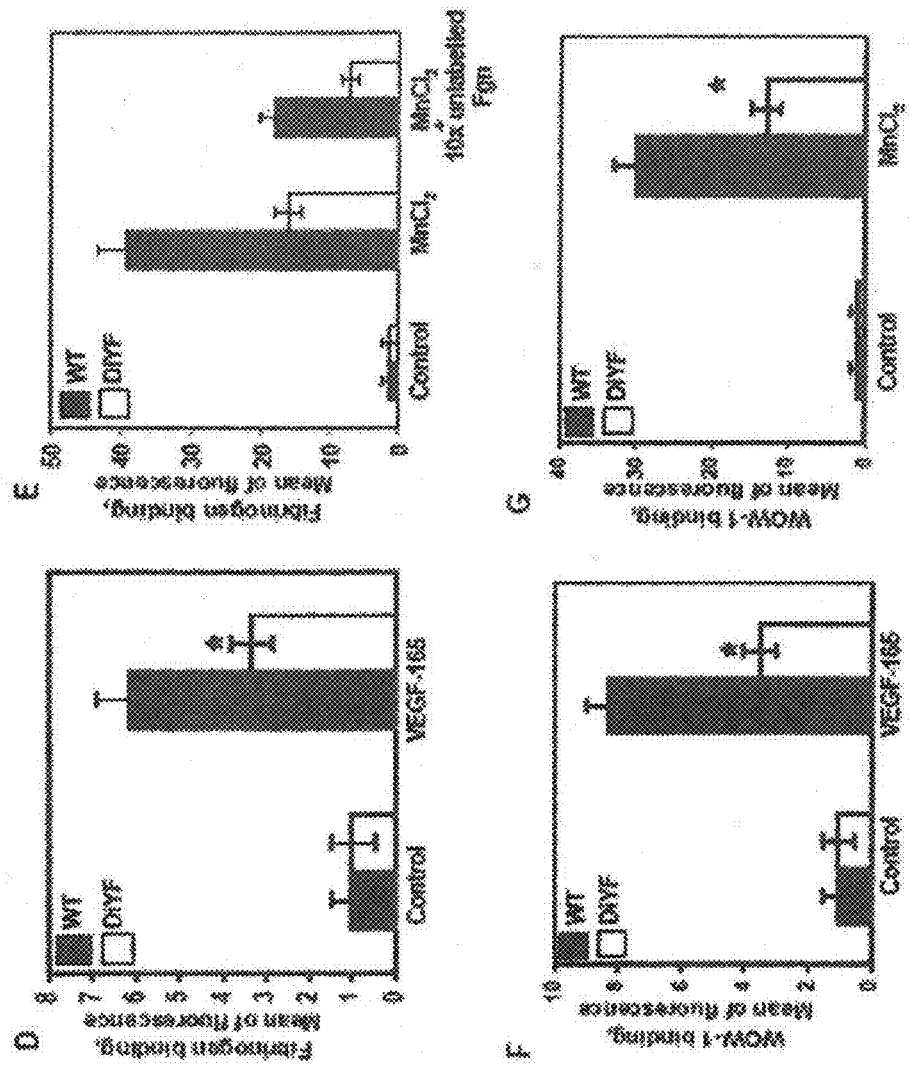
FIGS. 6D-G

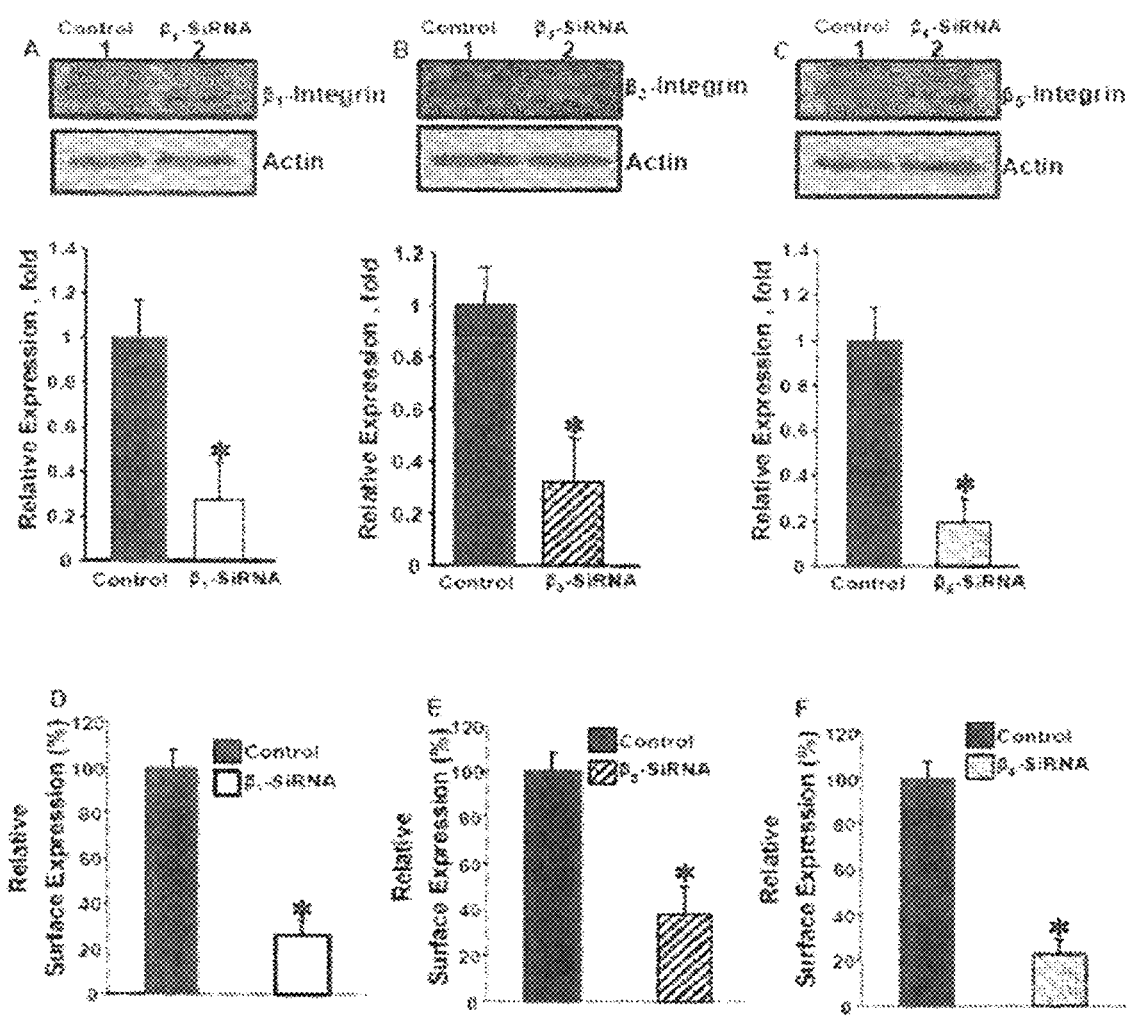
FIGS. 7A-F

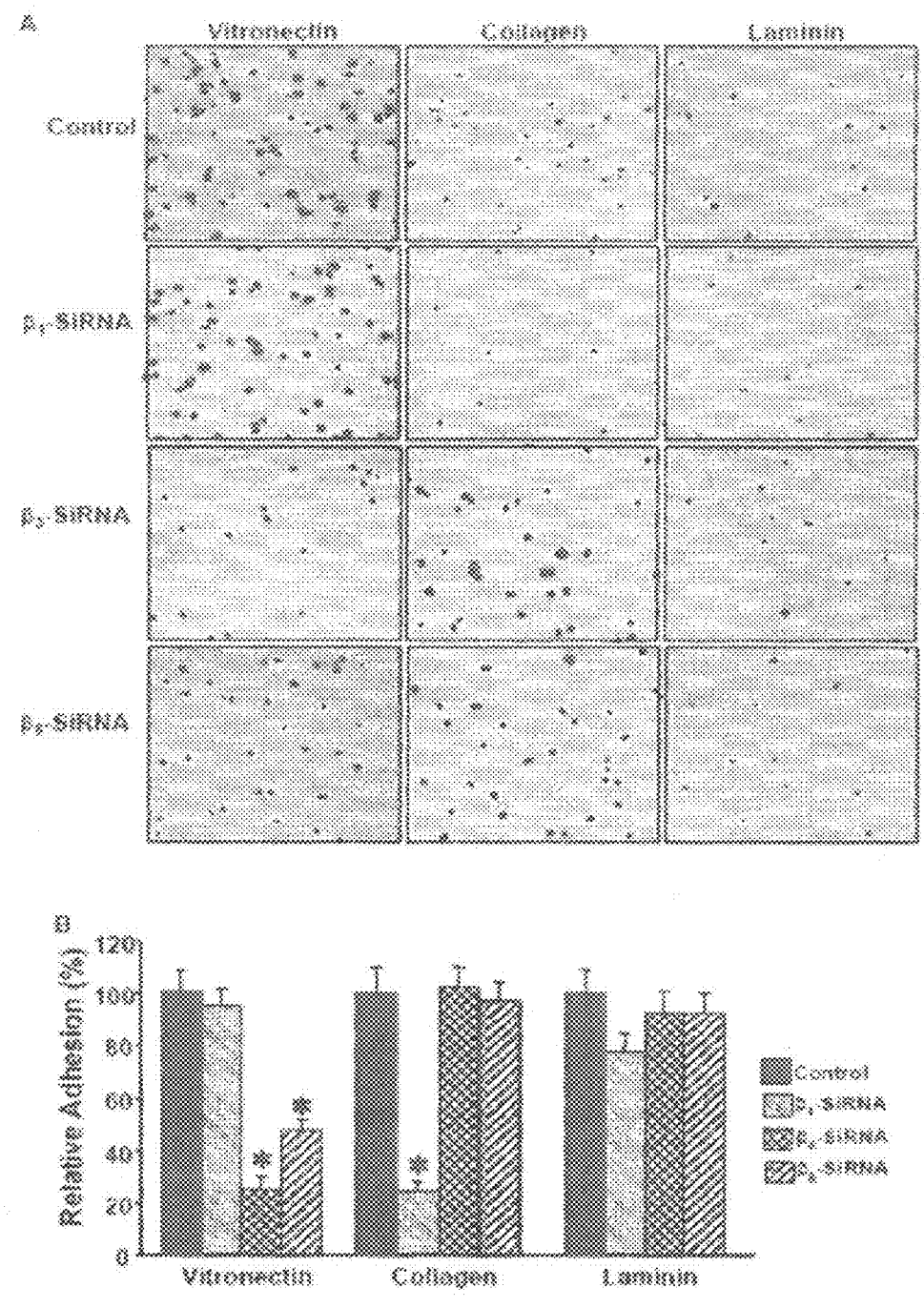
FIGS. 8A-B

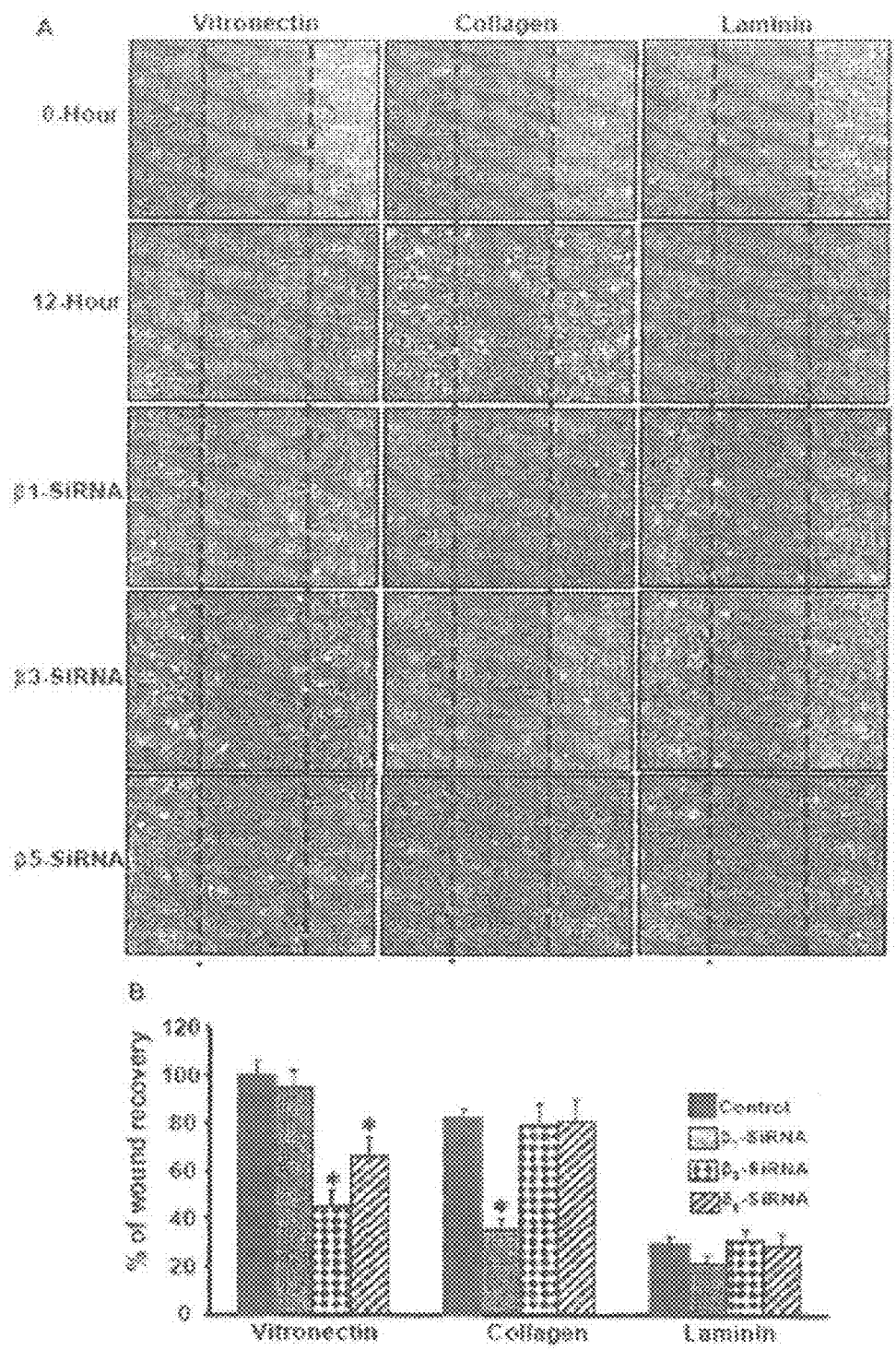
FIGS. 9A-B

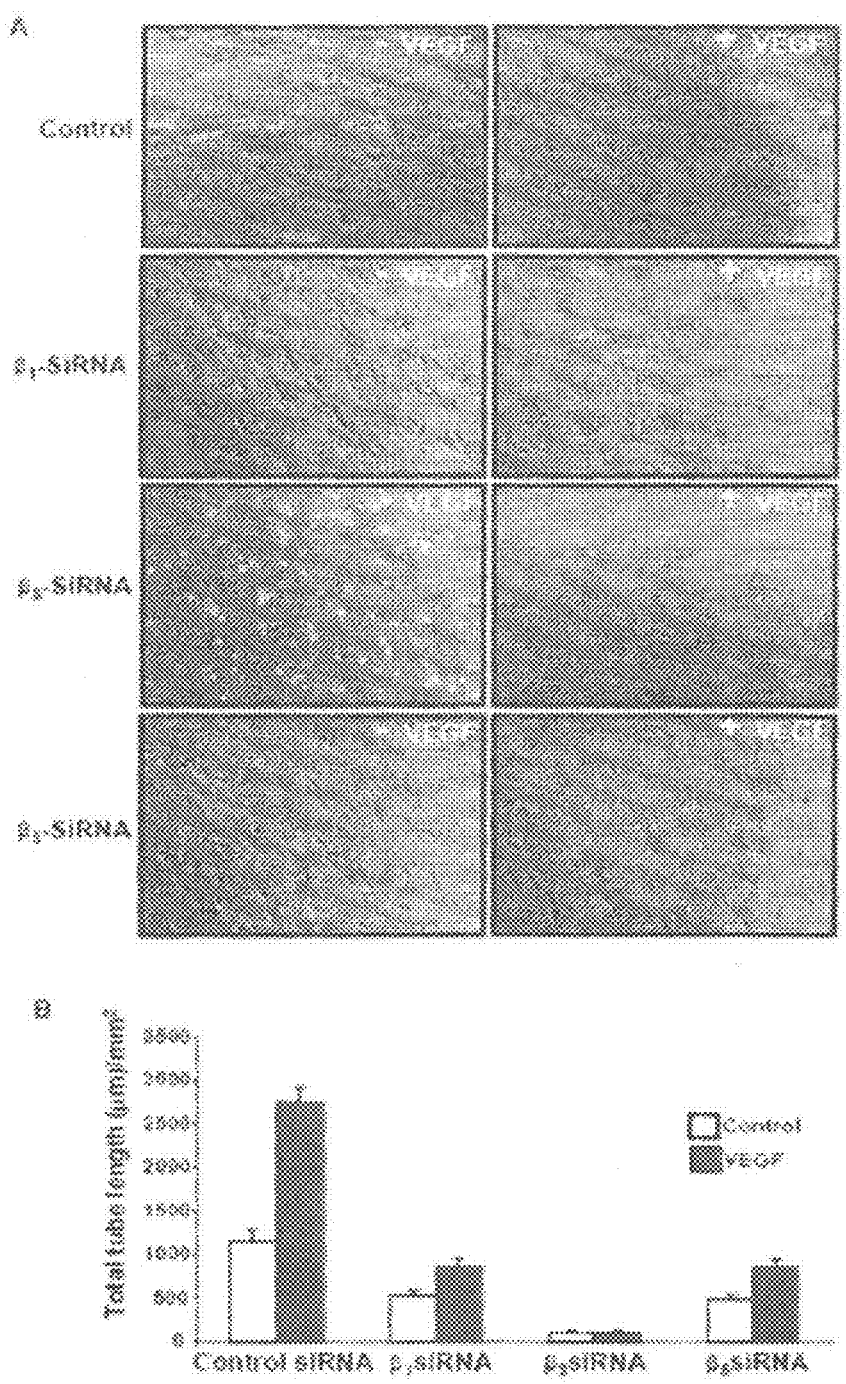
FIGS. 10A-B

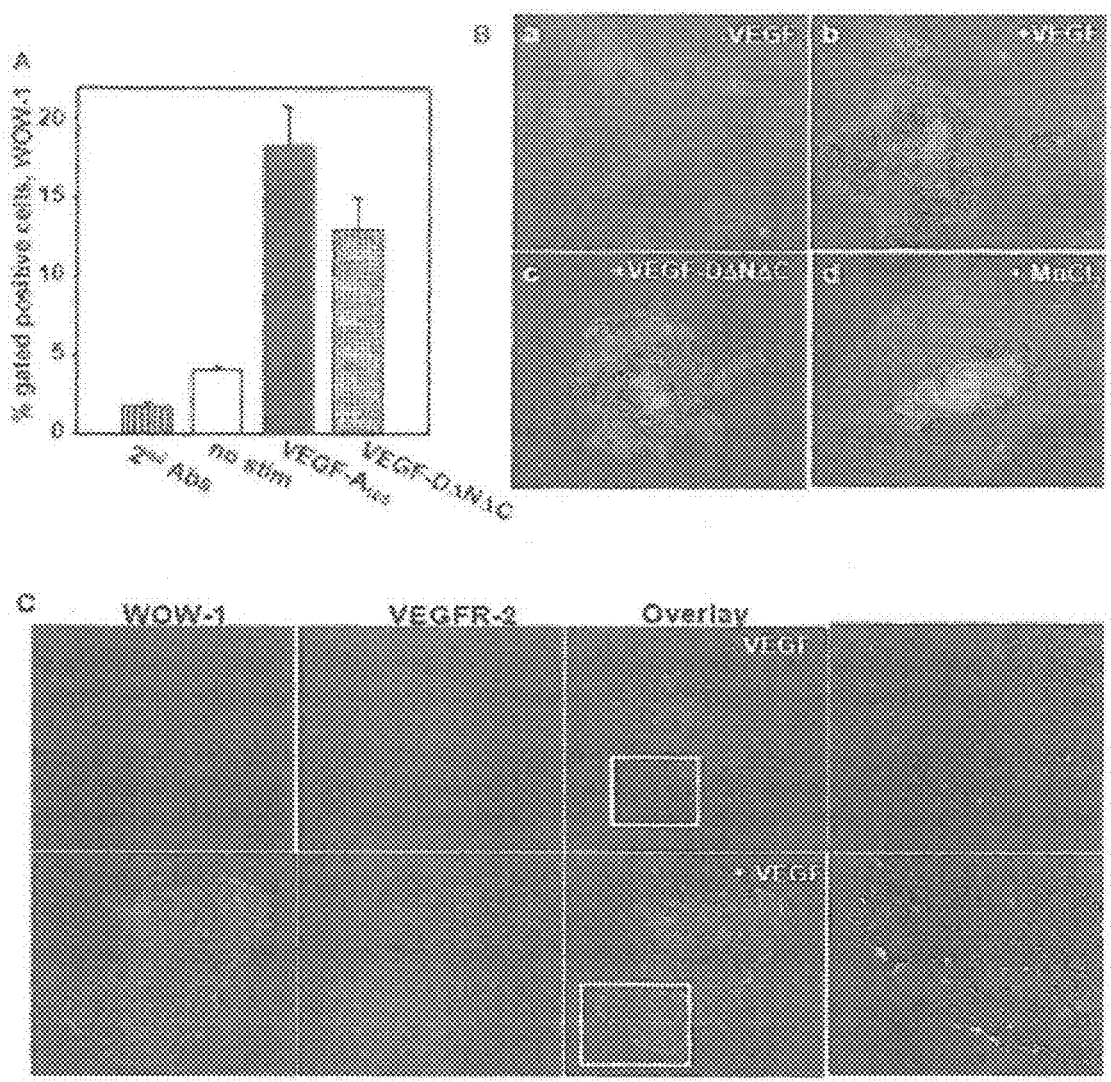
FIGS. 11A-C

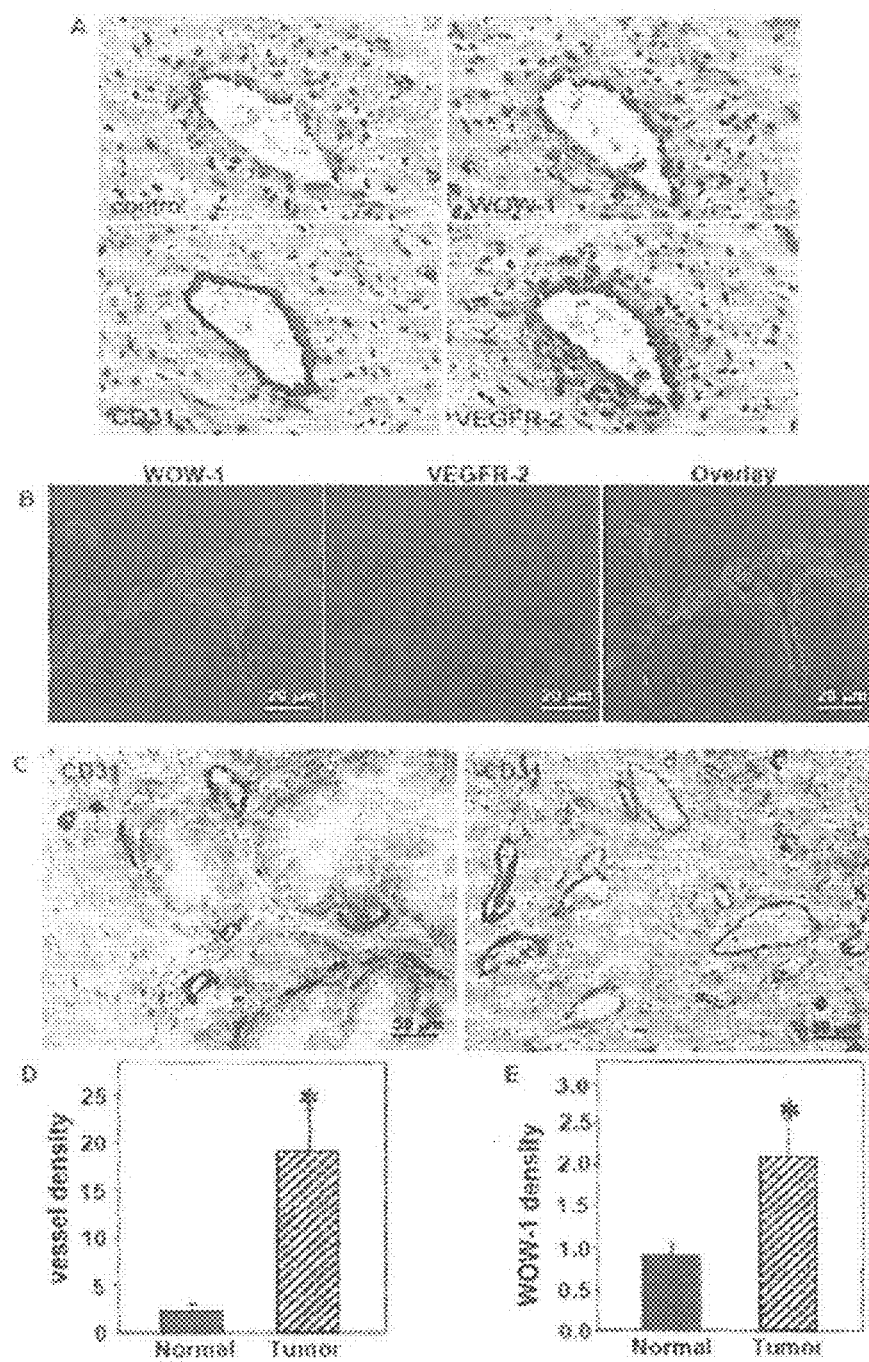
FIGS. 12A-E

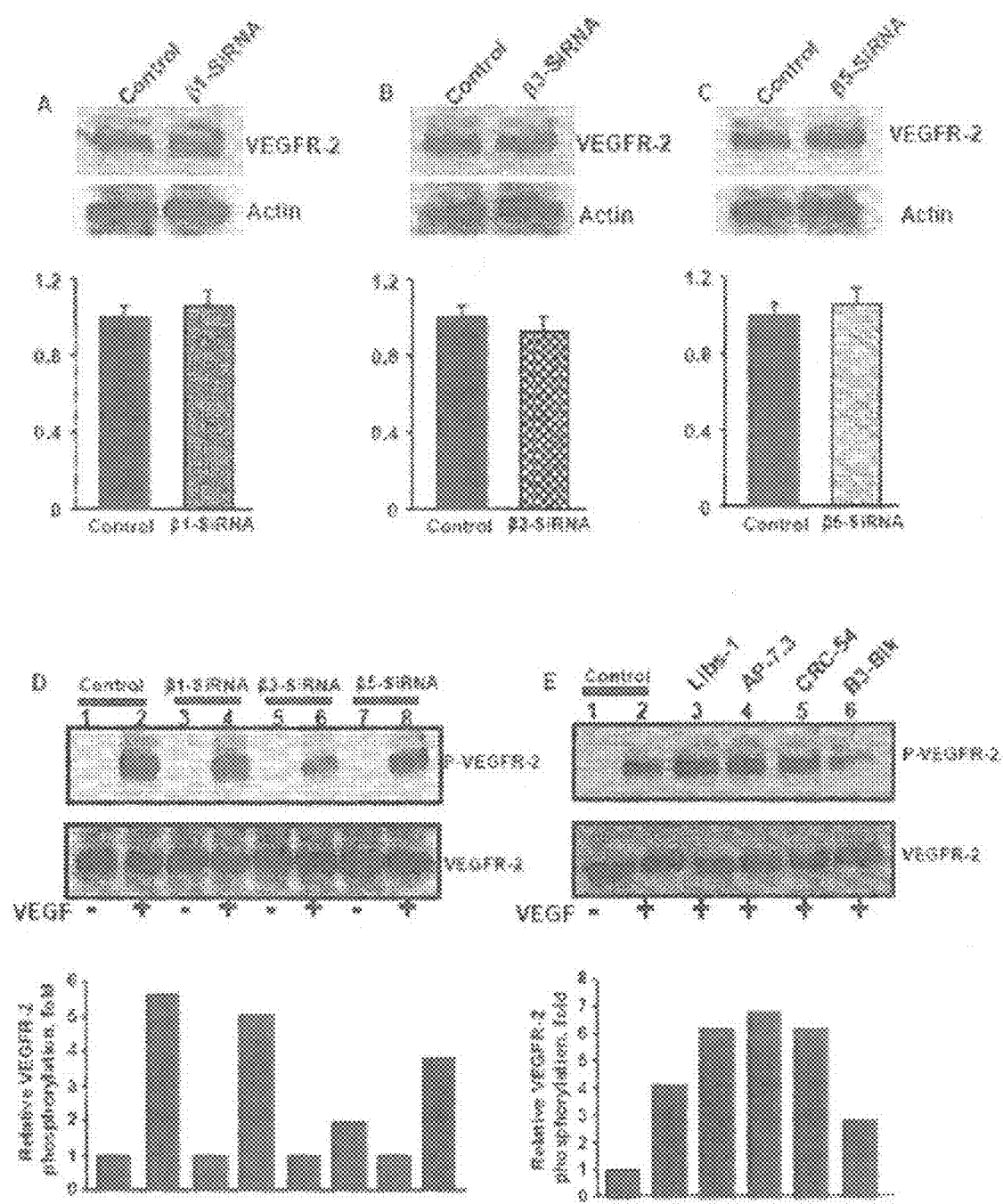
FIGS. 13A-E

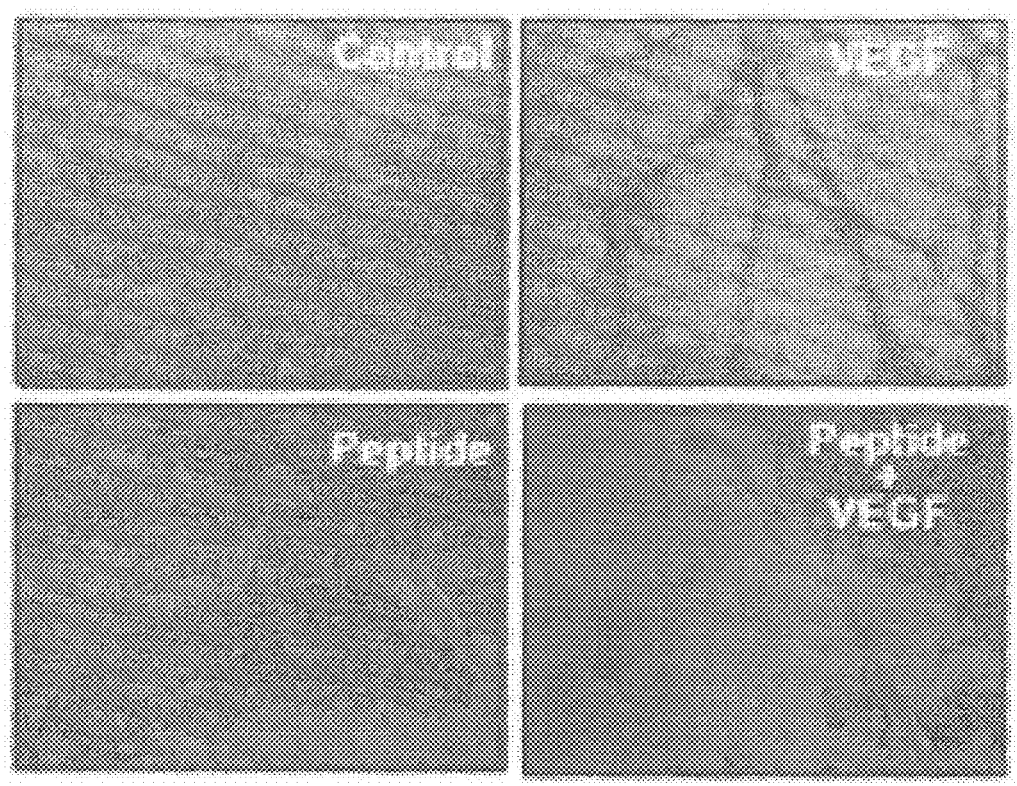
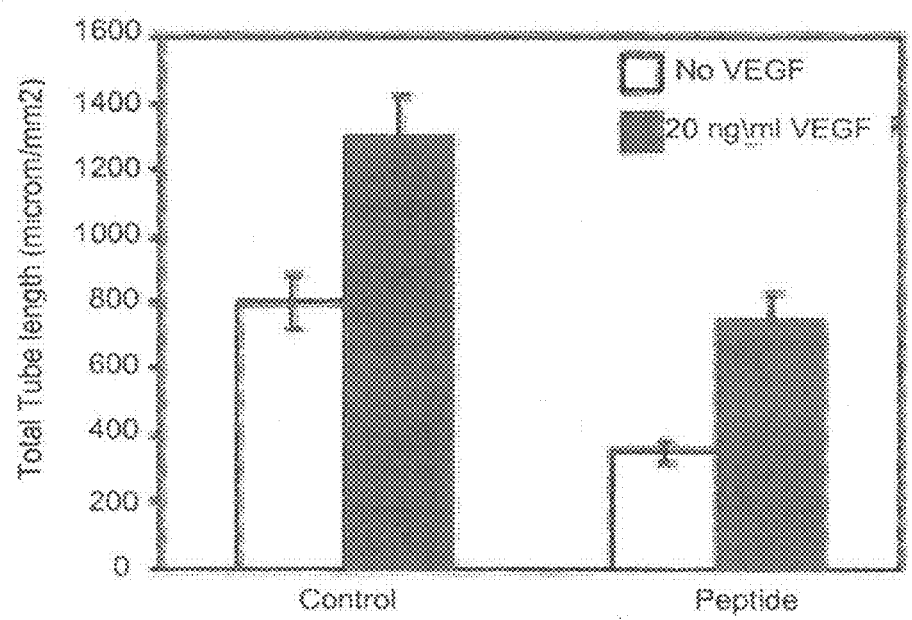
FIGS. 14A-B

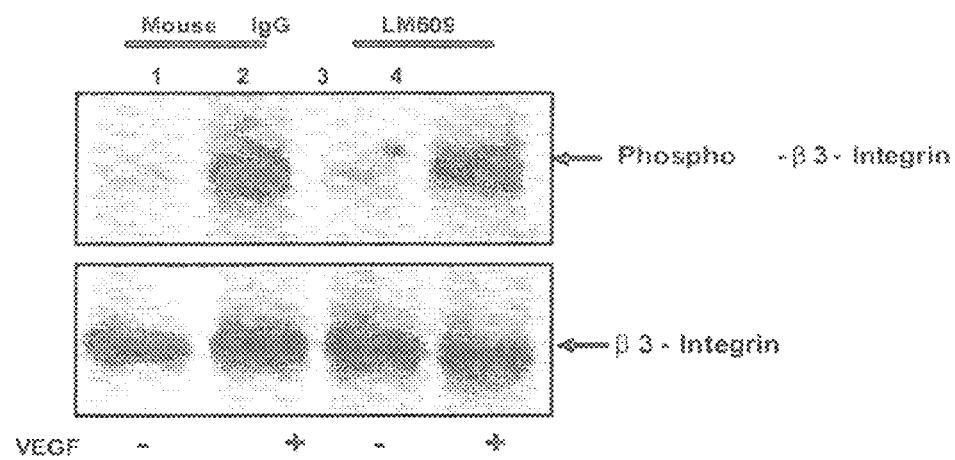
Fig. 15
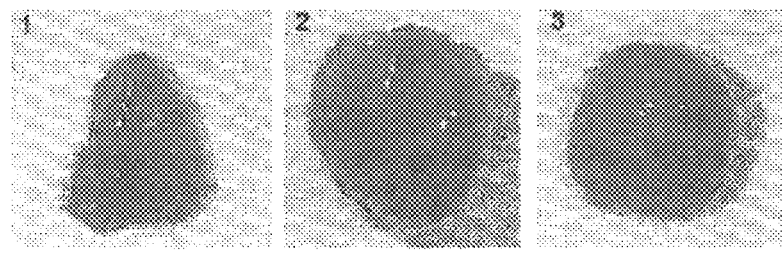
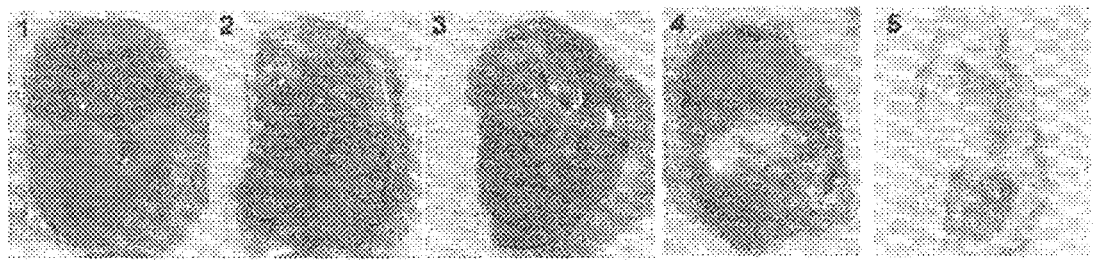
Fig. 16

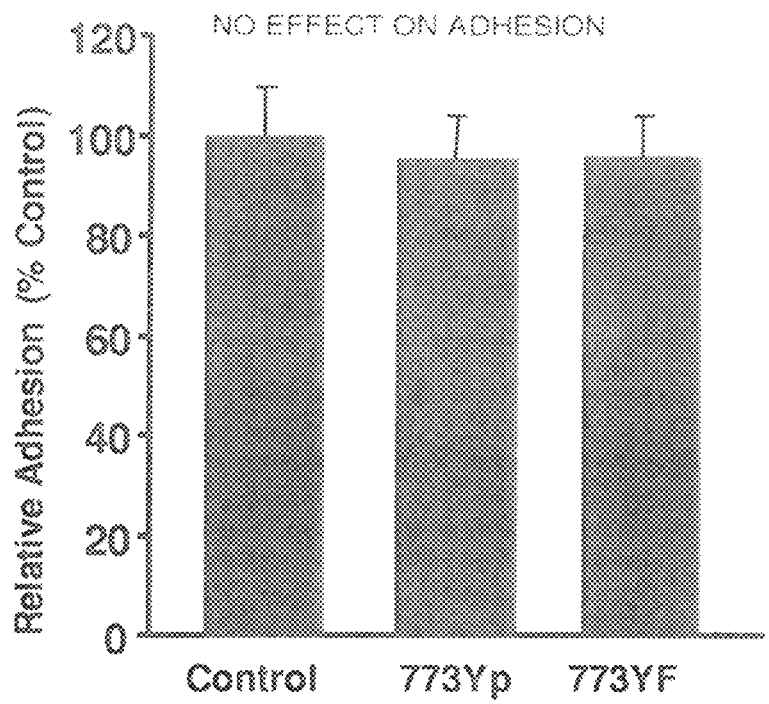
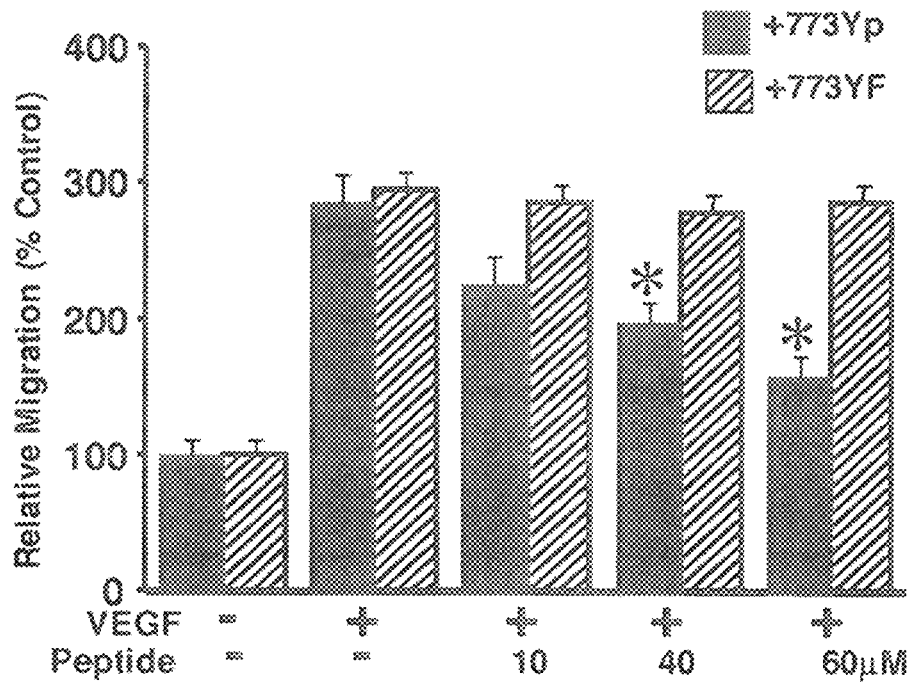
Fig. 18

Peptide 5 – linear new delivery NPLDK, Peptide 6 – linear new delivery NITDR

SEQUENCE LISTING

```
<160> NUMBER OF SEQ ID NOS: 42

<210> SEQ ID NO 1
<211> LENGTH: 17
<212> TYPE: PRT
<213> ORGANISM: Homo sapiens
<220> FEATURE:
<221> NAME/KEY: MOD_RES
<222> LOCATION: (8)..(8)
<223> OTHER INFORMATION: Yp is a phosphorylated tyrosine residude

<400> SEQUENCE: 1

Asp Thr Ala Asn Asn Pro Leu Tyr Pro Lys Glu Ala Thr Ser Thr Phe
1               5                   10                  15

Thr
```

```
<210> SEQ ID NO 2
<211> LENGTH: 23
<212> TYPE: PRT
<213> ORGANISM: Homo sapiens

<400> SEQUENCE: 2

Asp Thr Ala Asn Asn Pro Leu Tyr Lys Glu Ala Thr Ser Thr Phe Thr
1               5                   10                  15

Asn Ile Thr Tyr Arg Gly Thr
            20

<210> SEQ ID NO 3
<211> LENGTH: 38
<212> TYPE: PRT
<213> ORGANISM: Homo sapiens

<400> SEQUENCE: 3

Lys Glu Phe Ala Lys Phe Glu Glu Arg Ala Arg Ala Lys Trp Asp
1               5                   10                  15

Thr Ala Asn Asn Pro Leu Tyr Lys Glu Ala Thr Ser Thr Phe Thr Asn
            20                  25                  30

Ile Thr Tyr Arg Gly Thr
        35

<210> SEQ ID NO 4
<211> LENGTH: 16
<212> TYPE: PRT
<213> ORGANISM: Homo sapiens
<220> FEATURE:
<221> NAME/KEY: misc_feature
<222> LOCATION: (8)..(8)
<223> OTHER INFORMATION: Xaa is a Gamma-Carboxyglutamic acid

<400> SEQUENCE: 4

Asp Thr Ala Asn Asn Pro Leu Xaa Lys Glu Ala Thr Ser Thr Phe Thr
1               5                   10                  15

<210> SEQ ID NO 5
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 5

Asn Pro Leu Tyr Lys
1               5

<210> SEQ ID NO 6
<211> LENGTH: 5
<212> TYPE: PRT
<213> ORGANISM: Homo sapiens
<220> FEATURE:
<221> NAME/KEY: MOD_RES
<222> LOCATION: (4)..(4)
<223> OTHER INFORMATION: PHOSPHORYLATION

<400> SEQUENCE: 6

Asn Ile Thr Tyr Arg
1               5

<210> SEQ ID NO 7
<211> LENGTH: 5
<212> TYPE: PRT
```

```
<213> ORGANISM: Homo sapiens
<220> FEATURE:
<221> NAME/KEY: misc_feature
<222> LOCATION: (4)..(4)
<223> OTHER INFORMATION: Xaa is a Gamma-Carboxyglutamic acid

<400> SEQUENCE: 7

Asn Pro Leu Xaa Lys
1               5

<210> SEQ ID NO 8
<211> LENGTH: 5
<212> TYPE: PRT
<213> ORGANISM: Homo sapiens
<220> FEATURE:
<221> NAME/KEY: misc_feature
<222> LOCATION: (4)..(4)
<223> OTHER INFORMATION: Xaa is a Gamma-Carboxyglutamic acid

<400> SEQUENCE: 8

Asn Ile Thr Xaa Arg
1               5

<210> SEQ ID NO 9
<211> LENGTH: 5
<212> TYPE: PRT
<213> ORGANISM: Homo sapiens

<400> SEQUENCE: 9

Asn Pro Leu Asp Lys
1               5

<210> SEQ ID NO 10
<211> LENGTH: 5
<212> TYPE: PRT
<213> ORGANISM: Homo sapiens

<400> SEQUENCE: 10

Asn Ile Thr Asp Arg
1               5

<210> SEQ ID NO 11
<211> LENGTH: 20
<212> TYPE: PRT
<213> ORGANISM: Homo sapiens
<220> FEATURE:
<221> NAME/KEY: MOD_RES
<222> LOCATION: (14)..(14)
<223> OTHER INFORMATION: PHOSPHORYLATION

<400> SEQUENCE: 11

Cys Met Glu Glu Glu Glu Val Cys Asp Pro Lys Phe His Tyr Asp Asn
1               5                   10                  15

Thr Ala Gly Ile
            20

<210> SEQ ID NO 12
<211> LENGTH: 20
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION

<400> SEQUENCE: 12

Gln Thr Ser Gly Tyr Gln Ser Gly Tyr His Ser Asp Asp Thr Asp Thr
```

```
1               5                   10                  15

Thr Val Tyr Ser
            20

<210> SEQ ID NO 13
<211> LENGTH: 20
<212> TYPE: PRT
<213> ORGANISM: Homo sapiens
<220> FEATURE:
<221> NAME/KEY: MOD_RES
<222> LOCATION: (9)..(9)
<223> OTHER INFORMATION: PHOSPHORYLATION

<400> SEQUENCE: 13

Arg Asp Ile Tyr Lys Asp Pro Asp Tyr Val Arg Lys Gly Asp Ala Arg
1               5                   10                  15

Leu Pro Leu Lys
            20

<210> SEQ ID NO 14
<211> LENGTH: 23
<212> TYPE: PRT
<213> ORGANISM: Homo sapiens
<220> FEATURE:
<221> NAME/KEY: MOD_RES
<222> LOCATION: (12)..(12)
<223> OTHER INFORMATION: PHOSPHORYLATION

<400> SEQUENCE: 14

Trp Met Ala Pro Glu Thr Ile Phe Asp Arg Val Tyr Thr Ile Gln Ser
1               5                   10                  15

Asp Val Trp Ser Phe Gly Val
            20

<210> SEQ ID NO 15
<211> LENGTH: 20
<212> TYPE: PRT
<213> ORGANISM: Homo sapiens
<220> FEATURE:
<221> NAME/KEY: MOD_RES
<222> LOCATION: (6)..(6)
<223> OTHER INFORMATION: PHOSPHORYLATION

<400> SEQUENCE: 15

Leu Gly Ala Ser Pro Tyr Pro Gly Val Lys Ile Asp Glu Glu Phe Cys
1               5                   10                  15

Arg Arg Leu Lys
            20

<210> SEQ ID NO 16
<211> LENGTH: 20
<212> TYPE: PRT
<213> ORGANISM: Homo sapiens
<220> FEATURE:
<221> NAME/KEY: MOD_RES
<222> LOCATION: (10)..(10)
<223> OTHER INFORMATION: PHOSPHORYLATION

<400> SEQUENCE: 16

Glu Gly Thr Arg Met Arg Ala Pro Asp Tyr Thr Thr Pro Glu Met Tyr
1               5                   10                  15

Gln Thr Met Leu
            20

<210> SEQ ID NO 17
```

```
<211> LENGTH: 30
<212> TYPE: PRT
<213> ORGANISM: Homo sapiens
<220> FEATURE:
<221> NAME/KEY: MOD_RES
<222> LOCATION: (15)..(15)
<223> OTHER INFORMATION: PHOSPHORYLATION

<400> SEQUENCE: 17

Gly Asn Leu Leu Gln Ala Asn Ala Gln Gln Asp Gly Lys Asp Tyr Ile
1               5                   10                  15

Val Leu Pro Ile Ser Glu Thr Leu Ser Met Glu Glu Asp Ser
            20                  25                  30

<210> SEQ ID NO 18
<211> LENGTH: 20
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa is a Gamma-Carboxyglutamic acid

<400> SEQUENCE: 18

Cys Met Glu Glu Glu Glu Val Cys Asp Pro Lys Phe His Xaa Asp Asn
1               5                   10                  15

Thr Ala Gly Ile
            20

<210> SEQ ID NO 19
<211> LENGTH: 20
<212> TYPE: PRT
<213> ORGANISM: Homo sapiens
<220> FEATURE:
<221> NAME/KEY: misc_feature
<222> LOCATION: (19)..(19)
<223> OTHER INFORMATION: Xaa is a Gamma-Carboxyglutamic acid

<400> SEQUENCE: 19

Gln Thr Ser Gly Tyr Gln Ser Gly Tyr His Ser Asp Asp Thr Asp Thr
1               5                   10                  15

Thr Val Xaa Ser
            20

<210> SEQ ID NO 20
<211> LENGTH: 20
<212> TYPE: PRT
<213> ORGANISM: Homo sapiens
<220> FEATURE:
<221> NAME/KEY: misc_feature
<222> LOCATION: (9)..(9)
<223> OTHER INFORMATION: Xaa is a Gamma-Carboxyglutamic acid

<400> SEQUENCE: 20

Arg Asp Ile Tyr Lys Asp Pro Asp Xaa Val Arg Lys Gly Asp Ala Arg
1               5                   10                  15

Leu Pro Leu Lys
            20

<210> SEQ ID NO 21
<211> LENGTH: 23
<212> TYPE: PRT
<213> ORGANISM: Homo sapiens
<220> FEATURE:
<221> NAME/KEY: misc_feature
<222> LOCATION: (12)..(12)
<223> OTHER INFORMATION: Xaa is a Gamma-Carboxyglutamic acid
```

```
<400> SEQUENCE: 21

Trp Met Ala Pro Glu Thr Ile Phe Asp Arg Val Xaa Thr Ile Gln Ser
1               5                   10                  15

Asp Val Trp Ser Phe Gly Val
            20

<210> SEQ ID NO 22
<211> LENGTH: 20
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa is a Gamma-Carboxyglutamic acid

<400> SEQUENCE: 22

Leu Gly Ala Ser Pro Xaa Pro Gly Val Lys Ile Asp Glu Glu Phe Cys
1               5                   10                  15

Arg Arg Leu Lys
            20

<210> SEQ ID NO 23
<211> LENGTH: 20
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa is a Gamma-Carboxyglutamic acid

<400> SEQUENCE: 23

Glu Gly Thr Arg Met Arg Ala Pro Asp Xaa Thr Thr Pro Glu Met Tyr
1               5                   10                  15

Gln Thr Met Leu
            20

<210> SEQ ID NO 24
<211> LENGTH: 30
<212> TYPE: PRT
<213> ORGANISM: Homo sapiens
<220> FEATURE:
<221> NAME/KEY: misc_feature
<222> LOCATION: (15)..(15)
<223> OTHER INFORMATION: Xaa is a Gamma-Carboxyglutamic acid

<400> SEQUENCE: 24

Gly Asn Leu Leu Gln Ala Asn Ala Gln Gln Asp Gly Lys Asp Xaa Ile
1               5                   10                  15

Val Leu Pro Ile Ser Glu Thr Leu Ser Met Glu Glu Asp Ser
            20                  25                  30

<210> SEQ ID NO 25
<211> LENGTH: 20
<212> TYPE: PRT
<213> ORGANISM: Homo sapiens

<400> SEQUENCE: 25

Cys Met Glu Glu Glu Glu Val Cys Asp Pro Lys Phe His Asp Asp Asn
1               5                   10                  15

Thr Ala Gly Ile
            20

<210> SEQ ID NO 26
```

```
<211> LENGTH: 20
<212> TYPE: PRT
<213> ORGANISM: Homo sapiens

<400> SEQUENCE: 26

Gln Thr Ser Gly Tyr Gln Ser Gly Tyr His Ser Asp Asp Thr Asp Thr
1               5                   10                  15

Thr Val Asp Ser
            20

<210> SEQ ID NO 27
<211> LENGTH: 20
<212> TYPE: PRT
<213> ORGANISM: Homo sapiens

<400> SEQUENCE: 27

Arg Asp Ile Tyr Lys Asp Pro Asp Val Arg Lys Gly Asp Ala Arg
1               5                   10                  15

Leu Pro Leu Lys
            20

<210> SEQ ID NO 28
<211> LENGTH: 23
<212> TYPE: PRT
<213> ORGANISM: Homo sapiens

<400> SEQUENCE: 28

Trp Met Ala Pro Glu Thr Ile Phe Asp Arg Val Asp Thr Ile Gln Ser
1               5                   10                  15

Asp Val Trp Ser Phe Gly Val
            20

<210> SEQ ID NO 29
<211> LENGTH: 20
<212> TYPE: PRT
<213> ORGANISM: Homo sapiens

<400> SEQUENCE: 29

Leu Gly Ala Ser Pro Asp Pro Gly Val Lys Ile Asp Glu Glu Phe Cys
1               5                   10                  15

Arg Arg Leu Lys
            20

<210> SEQ ID NO 30
<211> LENGTH: 20
<212> TYPE: PRT
<213> ORGANISM: Homo sapiens

<400> SEQUENCE: 30

Glu Gly Thr Arg Met Arg Ala Pro Asp Asp Thr Thr Pro Glu Met Tyr
1               5                   10                  15

Gln Thr Met Leu
            20

<210> SEQ ID NO 31
<211> LENGTH: 30
<212> TYPE: PRT
<213> ORGANISM: Homo sapiens

<400> SEQUENCE: 31

Gly Asn Leu Leu Gln Ala Asn Ala Gln Gln Asp Gly Lys Asp Ile
1               5                   10                  15
```

```
Val Leu Pro Ile Ser Glu Thr Leu Ser Met Glu Glu Asp Ser
            20                  25                  30
```

<210> SEQ ID NO 32
<211> LENGTH: 12
<212> TYPE: PRT
<213> ORGANISM: Homo sapiens

<400> SEQUENCE: 32

```
Ala Ala Val Leu Leu Pro Val Leu Leu Ala Ala Pro
1               5                   10
```

<210> SEQ ID NO 33
<211> LENGTH: 24
<212> TYPE: PRT
<213> ORGANISM: Homo sapiens

<400> SEQUENCE: 33

```
His Pro Ile Gln Ile Ala Ala Phe Leu Ala Arg Ile Pro Pro Ile Ser
1               5                   10                  15

Ser Ile Gly Thr Cys Ile Leu Lys
            20
```

<210> SEQ ID NO 34
<211> LENGTH: 27
<212> TYPE: PRT
<213> ORGANISM: Homo sapiens
<220> FEATURE:
<221> NAME/KEY: MOD_RES
<222> LOCATION: (19)..(19)
<223> OTHER INFORMATION: PHOSPHORYLATION

<400> SEQUENCE: 34

```
Tyr Gly Lys Lys Arg Arg Gln Arg Arg Gly Asp Thr Ala Asn Asn
1               5                   10                  15

Pro Leu Tyr Lys Glu Ala Thr Ser Thr Phe Thr
            20                  25
```

<210> SEQ ID NO 35
<211> LENGTH: 7
<212> TYPE: PRT
<213> ORGANISM: Homo sapiens

<400> SEQUENCE: 35

```
Arg Arg Asn Pro Leu Asp Lys
1               5
```

<210> SEQ ID NO 36
<211> LENGTH: 7
<212> TYPE: PRT
<213> ORGANISM: Homo sapiens

<400> SEQUENCE: 36

```
Arg Arg Asn Ile Thr Asp Arg
1               5
```

<210> SEQ ID NO 37
<211> LENGTH: 15
<212> TYPE: PRT
<213> ORGANISM: Homo sapiens

<400> SEQUENCE: 37

```
Arg Arg Arg Lys Lys Arg Lys Arg Arg Asn Pro Leu Asp Lys
1               5                   10                  15
```

```
<210> SEQ ID NO 38
<211> LENGTH: 15
<212> TYPE: PRT
<213> ORGANISM: Homo sapiens

<400> SEQUENCE: 38

Arg Arg Arg Lys Lys Arg Lys Arg Arg Arg Asn Ile Thr Asp Arg
1               5                   10                  15

<210> SEQ ID NO 39
<211> LENGTH: 7
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa can be any naturally occurring amino acid

<400> SEQUENCE: 39

Arg Arg Asn Pro Leu Xaa Lys
1               5

<210> SEQ ID NO 40
<211> LENGTH: 7
<212> TYPE: PRT
<213> ORGANISM: Homo sapiens
<220> FEATURE:
<221> NAME/KEY: misc_feature
<222> LOCATION: (6)..(6)
<223> OTHER INFORMATION: Xaa is a Gamma-Carboxyglutamic acid

<400> SEQUENCE: 40

Arg Arg Asn Ile Thr Xaa Arg
1               5

<210> SEQ ID NO 41
<211> LENGTH: 15
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa is a Gamma-Carboxyglutamic acid

<400> SEQUENCE: 41

Arg Arg Arg Lys Lys Arg Lys Arg Arg Arg Asn Pro Leu Xaa Lys
1               5                   10                  15

<210> SEQ ID NO 42
<211> LENGTH: 15
<212> TYPE: PRT
<213> ORGANISM: Homo sapiens
<220> FEATURE:
<221> NAME/KEY: misc_feature
<222> LOCATION: (14)..(14)
<223> OTHER INFORMATION: Xaa is a Gamma-Carboxyglutamic acid

<400> SEQUENCE: 42

Arg Arg Arg Lys Lys Arg Lys Arg Arg Arg Asn Ile Thr Xaa Arg
1               5                   10                  15
```

COMPOUNDS AND METHODS OF MODULATING ANGIOGENESIS

RELATED APPLICATION

This application claims priority from U.S. Provisional Application No. 61/570,433, filed Dec. 14, 2011, the subject matter of which is incorporated herein by reference in its entirety.

GOVERNMENT FUNDING

This invention was made with government support under Grant No. NIH Grant PPG HL073311 awarded by National Institute of Health. The government has certain rights in the invention.

SEQUENCE LISTING

The instant application contains a Sequence Listing which has been submitted electronically in ASCII format and is hereby incorporated by reference in its entirety.

FIELD OF THE INVENTION

The present invention relates to compounds and methods of modulating angiogenesis and particularly relates to compounds and methods of modulating tumor growth and angiogenesis.

BACKGROUND

The process of angiogenesis involves coordinated endothelial cell (EC) proliferation, invasion, migration, and tube formation. This process is known to be induced by vascular growth factors and its receptors in coordination with extracellular matrix interacting molecules such as integrins. Integrins are heterodimeric transmembrane receptors, which play central roles in cell adhesion, migration, proliferation, differentiation and programmed cell death. $\alpha_v\beta_3$ integrin is a major integrin expressed on proliferating endothelial cells during angiogenesis and vascular remodeling. The disruption of $\alpha_v\beta_3$ integrin ligation either by blocking antibody (LM609 or Vitaxin) or by cyclic peptide antagonists (RGD) prevents blood vessel formation in mouse retina, rabbit cornea, chick chorioallantoic membrane, and human skin transplanted onto athymic mice. More importantly, function-blocking anti-$\beta_3$ antibody that recognizes at least three integrins ($\alpha_{IIb}\beta_3$, $\alpha_v\beta_3$ and $\alpha_M\beta_2$) has been shown to be beneficial in high risk angioplasty patients in part due to the blockade of $\alpha_v\beta_3$. In the studies on the role of $\alpha_v\beta_3$ in tumor vasculature and survival, histological examination of the tumor tissue treated with the $\alpha_v\beta_3$ blockers revealed reduction not only in the tumor cell viability but also in the vascular density.

Mice lacking $\alpha_v$ integrin showed relatively normal blood vessel development ($\alpha_v$ integrin knockout mice died at early stages of development due to extensive vasculature). Furthermore, studies using $\beta_3$ and $\beta_5$ null mice demonstrated an enhanced tumor growth, tumor angiogenesis and VEGF-A-induced vascular permeability due to the elevated levels of VEGFR-2 on EC. Therefore, it has been concluded that $\alpha_v\beta_3$ and $\alpha_v\beta_5$ integrin function as the negative regulators of angiogenesis by restricting the VEGF receptor-2 expression.

SUMMARY OF THE INVENTION

The present invention relates to a method of modulating angiogenesis in a cell population that includes cells that express αvβ3 integrin and VEGFR2. The method includes contacting the cell population with a therapeutically effective amount of a peptide that inhibits complexing αvβ3 integrin and VEGFR2. The peptide can consist of about 10 to about 50 amino acids and has an amino acid sequence substantially homologous to consecutive amino acids of a portion of the cytoplasmic doman of at least one of αvβ3 integrin or VEGFR2 that includes a tyrosine residue. The amino acid sequence of the peptide can include a phosphorylated tyrosine residue or an amino acid residue, which structurally mimics a phosphorylated tyrosine residue (e.g., γ-carboxyglutamic acid residue or aspartic acid residue), that is substituted for a corresponding tyrosine residue of the portion of the cytoplasmic domain of αvβ3 integrin or VEGFR2.

In an aspect of the invention, the cell population can comprise endothelial cells and the peptide can inhibit endothelial cell migration and capillary formation in the subject without affecting adhesion of the endothelial cells.

In another aspect of the invention, the peptide can inhibit tyrosine phosphorylation of the $\alpha_v\beta_3$ integrin and/or tyrosine phosphorylation of VEGFR2 upon VEGF stimulation. The peptide can also compete with $\alpha_v\beta_3$ integrin for interaction with VEGFR2.

In another aspect of the invention, the peptide can inhibit tyrosine phosphorylation of a tyrosine of the $\beta_3$ subunit of the $\alpha_v\beta_3$ integrin. In a particular aspect, the peptide can inhibit tyrosine phosphorylation of a tyrosine of the cytoplasmic domain of the $\beta_3$ subunit of the $\alpha_v\beta_3$ integrin, and more particularly, inhibit tyrosine phosphorylation of tyrosine 747 of the $\beta_3$ subunit of the $\alpha_v\beta_3$ integrin.

In a further aspect, the peptide can have an amino acid sequence that is substantially homologous to a portion of the cytoplasmic domain of the $\beta_3$ subunit of the $\alpha_v\beta_3$ integrin. The portion of the cytoplasmic domain of the $\beta_3$ subunit of the $\alpha_v\beta_3$ integrin can contain a tyrosine residue (e.g., tyrosine −747), which is capable of being phosphorylated upon complex formation of the $\alpha_v\beta_3$ integrin and VEGFR2.

In another aspect of the invention, the peptide can comprise, for example, an amino acid sequence selected from the group consisting of: SEQ ID NO:1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, and SEQ ID NO: 31.

The present invention also relates to a method of treating aberrant angiogenesis in a tissue. The method includes administering to the tissue a therapeutically effective amount of a peptide that inhibits complexing αvβ3 integrin and VEGFR2. The peptide consists of about 10 to about 50 amino acids and has an amino acid sequence substantially homologous to consecutive amino acids of a portion of the cytoplasmic doman of at least one of αvβ3 integrin or VEGFR2 that includes a tyrosine residue. The amino acid sequence of the peptide can inlcude a phosphorylated tyrosine residue or an amino acid residue, which structurally mimics a phosphorylated tyrosine residue (e.g., γ-carboxyglutamic acid residue or aspartic acid residue), that is substituted for a corresponding tyrosine residue of the portion of the cytoplasmic domain of αvβ3 integrin or VEGFR2.

In an aspect of the invention, the tissue can comprise a tumor in the subject. In another aspect, the tissue can include the choroid of an eye.

In an aspect of the invention, the peptide can inhibit tyrosine phosphorylation of the αvβ3 integrin and/or tyrosine phosphorylation of VEGFR2 upon VEGF stimulation. The peptide can also compete with αvβ3 integrin for interaction with VEGFR2.

In another aspect of the invention, the peptide can inhibit tyrosine phosphorylation of a tyrosine of the $\beta_3$ subunit of the $\alpha_v\beta_3$ integrin. In a particular aspect, the peptide can inhibit tyrosine phosphorylation of a tyrosine of the cytoplasmic domain of the $\beta_3$ subunit of the $\alpha_v\beta_3$ integrin, and more particularly, inhibit tyrosine phosphorylation of tyrosine 747 of the $\beta_3$ subunit of the $\alpha_v\beta_3$ integrin.

In a further aspect, the peptide can have an amino acid sequence that is substantially homologous to a portion of the cytoplasmic domain of the $\beta_3$ subunit of the $\alpha_v\beta_3$ integrin. The portion of the cytoplasmic domain of the $\beta_3$ subunit of the $\alpha_v\beta_3$ integrin can contain a tyrosine residue (e.g., tyrosine −747), which is capable of being phosphorylated upon complex formation of the $\alpha_v\beta_3$ integrin and VEGFR2.

In another aspect of the invention, the peptide can comprise, for example, an amino acid sequence selected from the group consisting of: SEQ ID NO:1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, and SEQ ID NO: 31.

The present invention further relates to a method of treating an angiogenic disorder in a subject. The method comprises contacting a cell population that includes cells that express αvβ3 integrin and VEGFR2 with a therapeutically effective amount of a peptide that inhibits complexing αvβ3 integrin and VEGFR2. The peptide consists of about 10 to about 50 amino acids and can have an amino acid sequence substantially homologous to consecutive amino acids of a portion of the cytoplasmic doman of at least one of αvβ3 integrin or VEGFR2 that includes a tyrosine residue. The amino acid sequence of the peptide can include a phosphorylated tyrosine residue or an amino acid residue that structurally mimics a phosphorylated tyrosine residue (e.g., γ-carboxyglutamic acid residue or aspartic acid residue) that is substituted for a corresponding tyrosine residue of the portion of the cytoplasmic domain of αvβ3 integrin or VEGFR2.

In an aspect of the invention, the peptide can inhibit tyrosine phosphorylation of the $\alpha_v\beta_3$ integrin and/or tyrosine phosphorylation of VEGFR2 upon VEGF stimulation. The peptide can also compete with $\alpha_v\beta_3$ integrin for interaction with VEGFR2.

In another aspect of the invention, the peptide can inhibit tyrosine phosphorylation of a tyrosine of the $\beta_3$ subunit of the $\alpha_v\beta_3$ integrin. In a particular aspect, the peptide can inhibit tyrosine phosphorylation of a tyrosine of the cytoplasmic domain of the $\beta_3$ subunit of the $\alpha_v\beta_3$ integrin, and more particularly, inhibit tyrosine phosphorylation of tyrosine 747 of the $\beta_3$ subunit of the $\alpha_v\beta_3$ integrin.

In a further aspect, the peptide can have an amino acid sequence that is substantially homologous to a portion of the cytoplasmic domain of the $\beta_3$ subunit of the $\alpha_v\beta_3$ integrin. The portion of the cytoplasmic domain of the $\beta_3$ subunit of the $\alpha_v\beta_3$ integrin can contain a tyrosine residue (e.g., tyrosine −747), which is capable of being phosphorylated upon complex formation of the $\alpha_v\beta_3$ integrin and VEGFR2.

In another aspect of the invention, the peptide can comprise, for example, an amino acid sequence selected from the group consisting of: SEQ ID NO:1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, and SEQ ID NO: 31.

In an aspect of the invention, the angiogenic disorder can include aberrant tumor growth. In another aspect, the angiogenic disorder can include age-related macular degeneration.

The present invention further relates to a pharmaceutical composition that includes a synthetic peptide. The peptide consists of about 10 to about 50 amino acids and has an amino acid sequence substantially homologous to consecutive amino acids of a portion of the cytoplasmic doman of at least one of αvβ3 integrin or VEGFR2 that includes a tyrosine residue. The amino acid sequence of the peptide can include a phosphorylated tyrosine residue or an amino acid residue, which structurally mimics a phosphorylated tyrosine residue (e.g., γ-carboxyglutamic acid residue or aspartic acid residue), that is substituted for a corresponding tyrosine residue of the portion of the cytoplasmic domain of αvβ3 integrin or VEGFR2.

In an aspect of the invention, the peptide can inhibit tyrosine phosphorylation of the $\alpha_v\beta_3$ integrin and/or tyrosine phosphorylation of VEGFR2 upon VEGF stimulation. The peptide can also compete with $\alpha_v\beta_3$ integrin for interaction with VEGFR2.

In another aspect of the invention, the peptide can inhibit tyrosine phosphorylation of a tyrosine of the $\beta_3$ subunit of the $\alpha_v\beta_3$ integrin. In a particular aspect, the peptide can inhibit tyrosine phosphorylation of a tyrosine of the cytoplasmic domain of the $\beta_3$ subunit of the $\alpha_v\beta_3$ integrin, and more particularly, inhibit tyrosine phosphorylation of tyrosine 747 of the $\beta_3$ subunit of the $\alpha_v\beta_3$ integrin.

In a further aspect, the peptide can have an amino acid sequence that is substantially homologous to a portion of the cytoplasmic domain of the $\beta_3$ subunit of the $\alpha_v\beta_3$ integrin. The portion of the cytoplasmic domain of the $\beta_3$ subunit of the $\alpha_v\beta_3$ integrin can contain a tyrosine residue (e.g., tyrosine −747), which is capable of being phosphorylated upon complex formation of the $\alpha_v\beta_3$ integrin and VEGFR2.

In another aspect of the invention, the peptide can comprise, for example, an amino acid sequence selected from the group consisting of: SEQ ID NO:1, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, and SEQ ID NO: 31.

BRIEF DESCRIPTION OF DRAWINGS

FIGS. 1 (A-C) illustrate extracellular matrix proteins and VEGF induce $\beta_3$ integrin cytoplasmic tyrosine motif phosphorylation. (A-B) $\beta_3$ integrin tyrosine phosphorylation upon adhesion to integrin ligands. Wild type (A) and DiYF (B) cells were either held in suspension (lane-1) or plated on poly-L-lysine (lane-2), gelatin (lane-3,4) with (lane 4) or without (lane 3) pervanadate treatment, laminin (lane-5), collagen (lane-6), vitronectin (lane-7), fibronectin (lane-8), fibrinogen (lane-9) and incubated at 37° C. for 60 mins. Cell lysates containing equal amount of protein were subjected to Western blot analysis using rabbit anti-integrin $\beta_3$ [$pY^{747}$] (upper panel A and B) and [$pY^{759}$] (middle panel A and B) antibody. Cell lysates were also analyzed for $\beta_3$ integrin expression as a loading control (lower panel A and B). (C) VEGF induces $\beta_3$ integrin tyrosine phosphorylation. WT and DiYF mouse lung EC were treated with 20 ng/ml of VEGF-A165 for 0 to 60 min as indicated. Phosphorylation status of $\beta_3Y^{747}$ (upper panel) and $\beta_3Y^{759}$ (middle panel) was assessed as described in A. Amount of $\beta_3$ integrin in all samples is shown in lower panel. Densitometry analysis was performed using KODAK 1D image analysis software and fold changes over control are shown.

FIGS. 2 (A-C) illustrate $\beta_3$ integrin cytoplasmic tyrosine motif is critical for endothelial cell adhesion, spreading and migration. (A-B) Adhesion and spreading of WT and DiYF endothelial cells on various integrin ligands. Plates were coated with 10 μg/ml vitronectin (VN), fibronectin (FN), laminin-1 (LM-1), collagen (COLL) or bovine serum albumin (BSA) over night at 4° C. Wild type and DiYF mouse lung EC were harvested and re-suspended in serum free media at $5 \times 10^5$ cells/ml. 100 μl cell suspension was plated on each well coated with integrin ligands. After incubation at 37° C. for 45 min wells were gently washed three times with DMEM and photographs were taken. The numbers of attached and spread cells per field were counted. Adhesion and spreading of WT EC on vitronectin was assigned a value of 100%. (P values were 0.000017 and 0.00003 for cell adhesion and spreading, respectively.) (C). Migration of WT and DiYF endothelial cells on various integrin ligands. Tissue culture inserts were coated with various integrin ligands. WT and DiYF mouse lung EC were trypsinized and seeded into the top chamber. Cells were allowed to migrate, fixed and stained with crystal violet. The non-migrated cells adhered to the top surface were removed and three random fields were photographed using Leica inverted phase contrast microscope. Number of cells migrated onto vitronectin-coated insert was assigned 100% (P=0.00004). (D) VEGF-induced migration of WT and DiYF mouse lung EC. Migration assay was performed as described above using vitronectin as a substrate. The lower chamber contained 0-20 ng/ml of VEGFA165. Cells were allowed to migrate, fixed, stained and photographed. Number of WT EC migrated in the absence of VEGF was referred as 100%. (E-F) Reduced migration of DiYF endothelial cells on $\beta_3$ integrin ligand. Wild type and DiYF EC were serum starved and wounded across the cell monolayer by scraping away a swath of cells. Wells were rinsed twice with sterile PBS and further cultured in DMEM medium containing 2% FBS. After wounding sites were photographed immediately (time zero) and 12 h later using phase contrast microscope (Leica) (P=0.00004). The data represents the results of three independent experiments. Images were acquired using a Leica DMIRB phase contrast microscope, objective 5×, and a Micromax RTE/CCD-1300-V-HS camera.

FIGS. 3 (A-D) illustrate $\beta_3$ integrin tyrosine 747 and 759 mutations impair angiogenic properties of EC. (A-B) Functional $\beta_3$ integrin is essential for endothelial cell organization into precapillary cords. WT and DiYF mouse lung endothelial cells were collected and re-suspended in DMEM containing 10% FCS. Equal numbers of cells were seeded on Matrigel coated plates and cells were allowed to adhere. After 24 h cells were overlaid with Matrigel with or without 40 ng/ml VEGF and maintained in culture for 6-8 days. Three random fields were photographed periodically using phase contrast microscope (Leica) (panel A). Results of quantification of cords numbers per field are presented (panel B) (P=0.0004). (C-D) $\beta_3$ integrin cytoplasmic tyrosine residues are critical for capillary tube formation. Single cell suspension of WT and DiYF mouse lung EC were transferred on Matrigel coated plates and further incubated at 37° C. for 8 h with or without 20 ng/ml VEGF. Endothelial capillary tubes formed in Matrigel were observed using an inverted phase contrast microscope (Leica) and photographs were taken. The length of tubes in random fields from each well was analyzed using ImagePro software and shown in panel D. The data represents the results of three independent experiments. Images were acquired using a Leica DMIRB phase contrast microscope, objective 5×, and a Micromax RTE/CCD-1300-V-HS camera.

FIGS. 4 (A-H) illustrate $\beta_3$ integrin cytoplasmic tyrosine mutations result in impaired capillary growth ex vivo. (A-B) $\beta_3$ integrin cytoplasmic tyrosine motif is required for normal microvessel growth. Wild type (upper panel) and DiYF (lower panel) mouse aortic rings were embedded in Matrigel and maintained at 37° C. for six days. Microvessels outgrowths from aortic rings were observed periodically and photographed using Leica DMIRB phase contrast microscope. Numbers of microvessel sprouts from aortic rings were counted and represented as bar diagram (panel B). (C-D) Defective $\beta_3$ integrin tyrosine phosphorylation reduces VEGF-induced microvessel outgrowth. Wild type and DiYF mouse aortic rings were implanted in Matrigel with or without 40 ng/ml VEGF and maintained under aseptic condition for six days. Microvessel growths from implants were observed periodically and microphotographed. Representative images were shown in panel C. Numbers of microvessel outgrowth from aortic implants were counted and shown in panel D). (E-G) In ex vivo aortic ring assay using WT and DiYF aortic rings was performed in the presence of DMEM without any supplements (panel E), with endothelial growth supplement (panel F), or with 40 ng/ml VEGF together with endothelial growth supplement (panel G). Aortic rings were observed every two days, numbers of sprouts from each implant were counted and photographs were taken. Growth kinetics of wild type and DiYF aortic rings under various conditions were analyzed and represented as growth curves. The data represents the results of three independent experiments performed in triplicates. Images were acquired using a Leica DMIRB phase contrast microscope, objective 5×, and a Micromax RTE/CCD-1300-V-HS camera.

FIGS. 5 (A-F) illustrate $\beta_3$ integrin phosphorylation controls integrin activation. (A-B) DiYF EC exhibit reduced fibrinogen binding in response to growth factors. Wild type and DiYF mouse lung EC were serum starved for 4 h and washed twice with 1×PBS. These cells were incubated with FITC-fibrinogen in the presence or absence of 20 ng/ml VEGF for 45 min at 37° C. Cells were fixed with 0.4% formaldehyde, washed and analyzed by flow cytometry. Bars represent mean fluorescence intensity of three independent experiments performed in triplicates (panel A). Wild type and DiYF mouse lung endothelial cells were stimulated with 1 mM $MnCl_2$. $MnCl_2$ induced fibrinogen binding was diminished by 10 fold excess of unlabelled fibrinogen showing specificity of binding (panel B). *Indicates significant difference between WT and DiYF EC (P<0.05). (C-D) $\beta_3$ integrin cytoplasmic tyrosine motif is essential for interaction with monovalent ligand WOW-1

Figure 17:
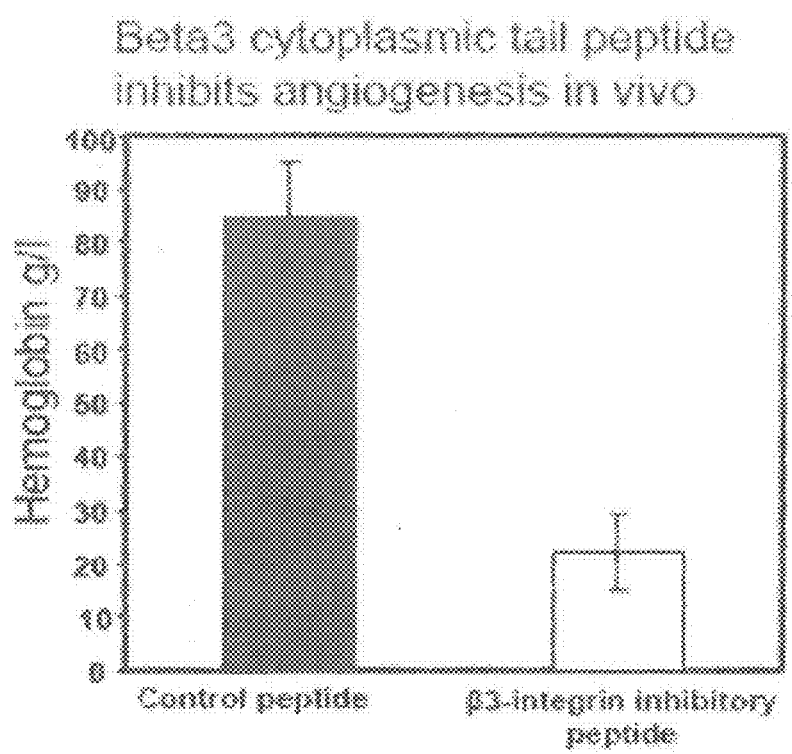

Fab. Wild type and DiYF mouse lung endothelial cells were serum starved for 4 h, washed twice with PBS and incubated with WOW-1 Fab in the presence or absence of 20 ng/ml VEGF for 45 min at 37° C. Cells were washed and incubated with FITC-conjugated goat anti-mouse IgG for 30 min at room temperature. Cells were fixed with 0.4% formaldehyde, washed and analyzed by flow cytometry. Bars represent mean fluorescence intensity of three independent experiments performed in triplicates (panel C). Wild type and DiYF mouse lung endothelial cells were also induced with 1 mM $MnCl_2$ as positive control (panel B). *Indicates significant difference between wild type and DiYF endothelial cells ($P<0.05$).

FIGS. 6 (A-G) illustrate $\beta_3$ integrin cytoplasmic tyrosine residues are required for VEGF induced VEGF receptor and $\beta_3$ integrin interaction. Wild type (C) and DiYF (D) mouse lung endothelial cells were either kept in suspension (lanes 1 and 2) or plated on vitronectin coated (lanes 3 and 4) or laminin coated (lanes 5 and 6) plates. These cells were treated with 20 ng/ml VEGF for 15 min (lanes 2, 4 and 6), cells were lysed, immunoprecipitated with rabbit-anti mouse $\beta_3$ integrin antibody and analyzed Western blot using rabbit-anti mouse VEGF receptor antibody. The same blots were reprobed with rabbit-anti mouse $\beta_3$ integrin antibody to conform equal loading (middle panel of C and D). IgG bands also conform equal amount of antibody have been used for immunoprecipitation (Lower panel of C and D).

FIGS. 7 (A-F) illustrate knockdowns of beta subunits of integrins on endothelial cells by specific siRNAs. A-C, HUVECs were transfected with control siRNA or integrin specific siRNA and cell lysates were analyzed for expression of $\beta 1$ (A), $\beta 3$ (B), or $\beta 5$ (C) integrin subunits using specific antibody. Densitometry analysis was performed and results are shown in bar graphs (lower panel). D-E, Cell surface expression of $\beta 1$ (D), $\beta 3$ (E), or $\beta 5$ (F) integrin subunits in endothelial cells was assessed by FACS analysis. Cells were fixed with 3% paraformaldehyde, stained with primary antibody against corresponding integrin and with secondary antibody labeled with Alexa 488. Mean of fluorescence intensity was measured; the value obtained using control cells, was assigned 100%. Asterisks indicate significant difference over control ($P<0.0038$).

FIGS. 8 (A-B) illustrate specificity of integrins in reorganization on distinct ECM ligands. (A-B) HUVECs were transfected with control siRNA or siRNA specific for $\beta 1$, $\beta 3$, or $\beta 5$ integrin. Wells of the microtiter plates were coated with vitronectin, collagen, or laminin-1 and were incubated overnight at 4° C. siRNA-transfected EC were harvested and resuspended in serum-free media at $5\times10^5$ cells/mL. The cell suspension (100 μL) was plated on a microtiter well coated with integrin ligand. After incubation at 37° C. for 45 min, wells were gently washed three times with DMEM and photographs were taken (panel A). The numbers of attached cells per field were counted and untransfected cells adhered on the individual ECM ligand were assigned a value of 100% (panel B). Asterisks indicate significant difference over control ($P<0.0046$).

FIGS. 9 (A-B) illustrate Vitronectin ($\alpha_v\beta_3$) and collagen ($\alpha 5\beta 1$) receptors regulate endothelial cell migration. (A-B) HUVECs were transfected with control siRNA or siRNA specific for $\beta 1$, $\beta 3$, or $\beta 5$ integrin. These cells were grown to confluence on 12-well plates precoated with individual integrin ligand. Cells were serum starved and wounded across the cell monolayer by scraping away a swath of cells. Wells were rinsed twice with sterile PBS and further cultured in DMEM medium containing 2% FBS. Sites were photographed immediately after wounding (zero hour) and 12 h later using a phase contrast microscope (panel A). Images were acquired using a Leica DMIRB phase contrast microscope, objective 5×, and a Micromax RTE/CCD-1300-V-HS camera. The mean wound area recovery by nontransfected endothelial cells on vitronectin for 12 hours was designated as 100% and relative % of wound recovery for siRNA-transfected EC were determined (panel B). Asterisks indicate significant difference over control ($P<0.0058$).

FIGS. 10 (A-B) illustrate $\beta 3$ integrin regulates endothelial cell morphogenesis in vitro. (A-B) HUVECs were transfected with control siRNA or siRNA specific for $\beta 1$, $\beta 3$, or $\beta 5$ integrin. Cells were transferred to Matrigel coated plates and further incubated at 37° C. for 8 h with or without 20 ng/mL VEGF. Endothelial capillary tubes formed in Matrigel were observed using an inverted phase contrast microscope and photographs were taken (panel A). Mean length of tubes from five random fields were measured using ImagePro software (panel B). Asterisks indicate significant difference over control.

FIGS. 11 (A-C) illustrate activated $\alpha_v\beta_3$ integrin co-localizes with VEGFR-2 on endothelial cells. (A) To evaluate VEGF/VEGFR-2 dependent activation of $\alpha_v\beta_3$ integrin, semiconfluent, serum starved HUVECs were induced with VEGF-A165 or VEGFDΔNΔC. These cells were further incubated with WOW-1 Fab fragment and goat anti-mouse IgG labeled with AlexaFluor 488. Fixed cells were then analyzed by flow cytometry. (B) HUVECs were grown on the gelatin-coated glass coverslips. These cells were serum starved and induced with VEGF-A165, VEGF-DΔNΔC, or MnC12 in presence of WOW-1 Fab fragment. Cells were washed and further incubated with goat anti-mouse IgG labeled with AlexaFluor 488. Cells were fixed, observed under fluorescence microscope and photographs were taken. (C) $\alpha_v\beta_3$ integrin and VEGFR-2 co-localize on endothelial cells. HUVECs were serum-starved overnight and stimulated with 20 ng/mL VEGF for 5 minutes. These cells were stained with WOW-1 and anti-VEGFR-2, followed by the incubation with goat anti-mouse IgG labeled with AlexaFluor 488 and goat anti-rabbit IgG conjugated with AlexaFluor 594. Without stimulatory signal (upper panel), very little co-localization of $\beta 3$ integrin and VEGFR-2 was observed. Upon VEGF stimulation (lower panel), the affinity of $\alpha_v\beta_3$ increases and co-localized with VEGFR-2.

FIGS. 12 (A-E) illustrate the level of $\alpha_v\beta_3$ integrin activation is index for degree of tumor angiogenesis. (A) Activated $\alpha_v\beta_3$ integrin co-localizes with VEGFR-2 on endothelial cells of proliferating blood vessel. Parallel prostate tumor tissue sections were cut and stained for WOW-1 (activated $\alpha_v\beta_3$ integrin), CD31 (endothelial cell marker), and VEGFR-2. Blood vessels (revealed by CD31 staining) were positively stained for both WOW-1 and VEGFR-2, indicating the co-localization of activated $\alpha_v\beta_3$ with VEGFR-2 in tumor vasculature. (B) Frozen parallel prostate tumor sections were stained for activated αVβ3 integrin (WOW-1 Fab) and VEGFR-2. Tissue sections were analyzed under a confocal microscope and photographs were taken. (C-D) Normal prostate tissue (panel C) and prostate tumor sections (panel D) were stained for CD-31 and WOW-1. Vascular density was increased at least by 6 times in prostate tumors compared to normal prostate tissue. (E) Vascular density was positively correlated with the density of WOW-1-positive vasculature in the two tissue samples. Asterisks indicate significant difference over normal tissue.

FIGS. 13 (A-E) illustrate VEGF-induced VEGFR-2 phosphorylation is subordinate to αvβ3 integrin activation status. (A-C) Effect of integrin knockdown on VEGFR-2 expression was evaluated by transfecting HUVECs with siRNA specific for (A) β1, (B) β3, or (C) β5 integrin. Cell lysates were analyzed for expression of VEGFR-2. Densitometry analysis was performed and results are shown as bar graphs (lower panels). (D-E) αvβ3 integrin activation dependent phosphorylation of VEGFR-2. HUVECs were transfected with β1, β3, or β5 integrant-specific siRNA and induced with 20 ng/mL VEGF for 5 min. (D) Cell lysates were analyzed for phosphorylation of VEGFR-2 using specific antibody. Densitometry analysis was performed and results are shown as bar graphs (lower panel). (E) HUVECs were incubated with αvβ3 integrin-activating antibody (Libs-1, AP-7.3, CRC-54) or β3 integrin blocking antibody. These cells were induced with VEGF for 5 min and cell lysates were analyzed for phosphorylation of VEGFR-2 using specific antibody. Densitometry analysis was performed and results are shown as bar graphs (lower panel).

FIGS. 14 (A-B) illustrate (A) photographs of endothelial cell tube formation in a matrigel assay for endothelial cells subjected to VEGF, a peptide in accordance with the present invention, and VEGF in conjunction with a peptide in accordance with the present invention; and (B) a graph showing the results.

FIG. 15 are blots illustrating the phosphorylation status of β3 integrin upon treatment with LM609 antibody (vitaxin).

FIG. 16 illustrates photographs of matrigel plugs in accordance with an aspect of the invention.

FIG. 17 illustrates a graph showing that β3 cytoplasmic tail peptide inhibits angiogenesis in vivo.

FIG. 18 illustrates charts showeing that an inhibiting peptide in accordance with an aspect of the present invention (A) has no effect on endothelial cell adhesion and (B) prevents endothelial cell migration.

Figure 19:
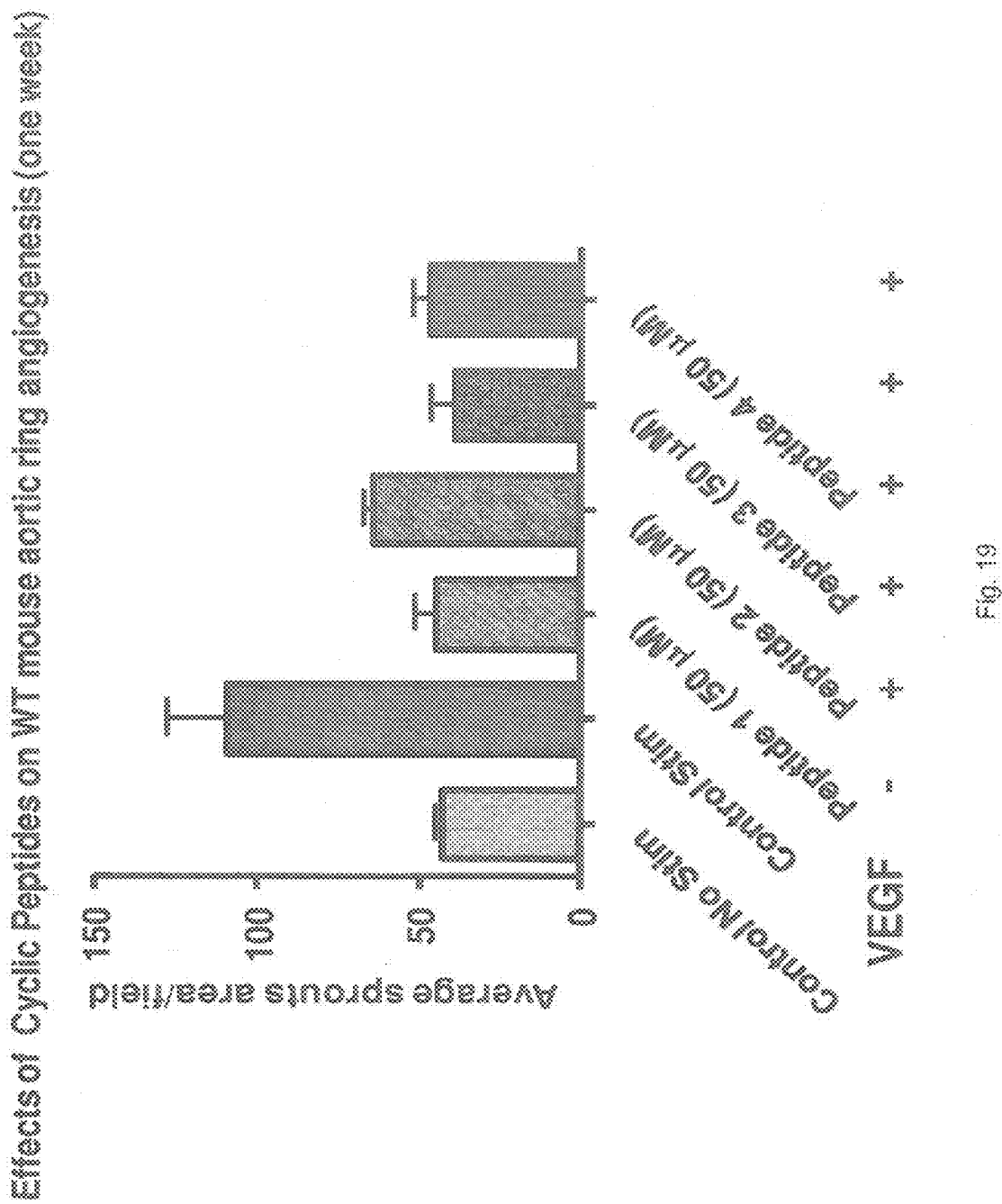

FIG. 19 illustrates a chart showing the effect of cylic inhibiting peptides in accordance with an aspect of the present invention on WT mousute aortic ring angiogenesis after one week.

Figure 20:
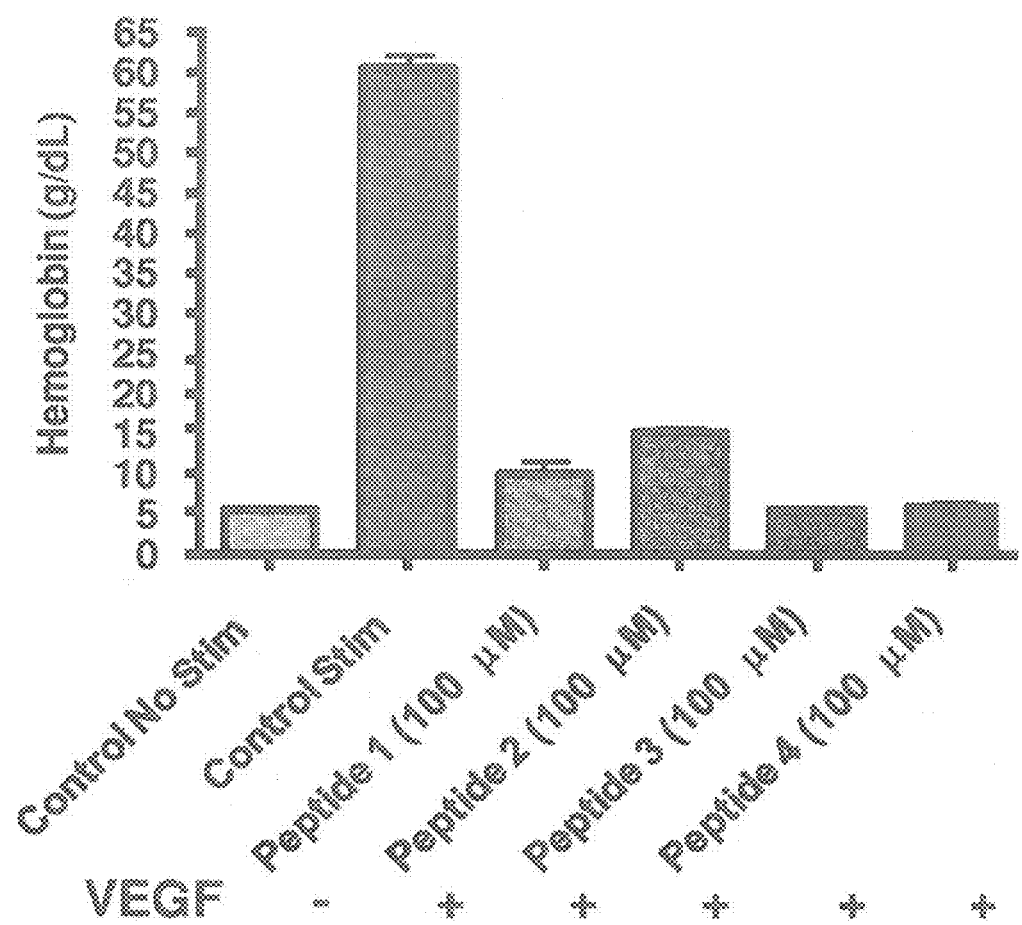

FIG. 20 illustrates a chart showing the effects of cyclic inhibiting peptides in accordance with an aspect of the invention on matrigel plug angiogenesis.

Figure 21:
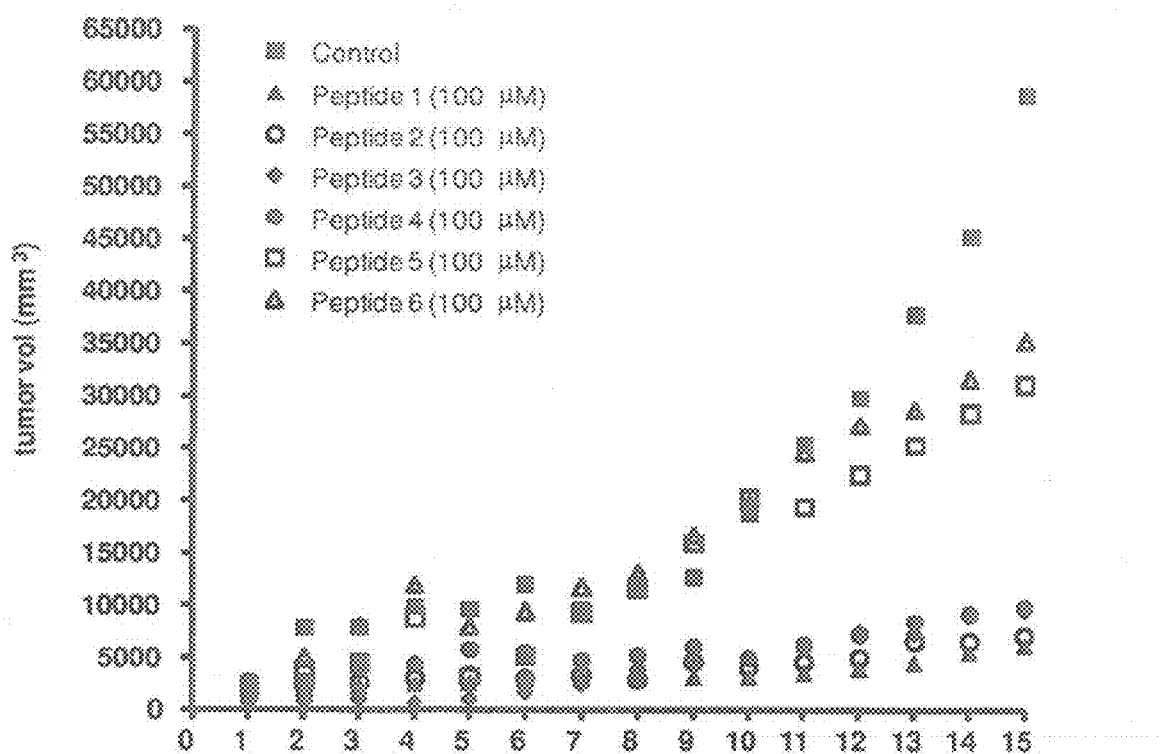

FIG. 21 illustrates a chart showing the effects of cyclic and linear inhibiting peptides in accordance with an aspect of the invention on progression of implanted tumors.

Figure 22:
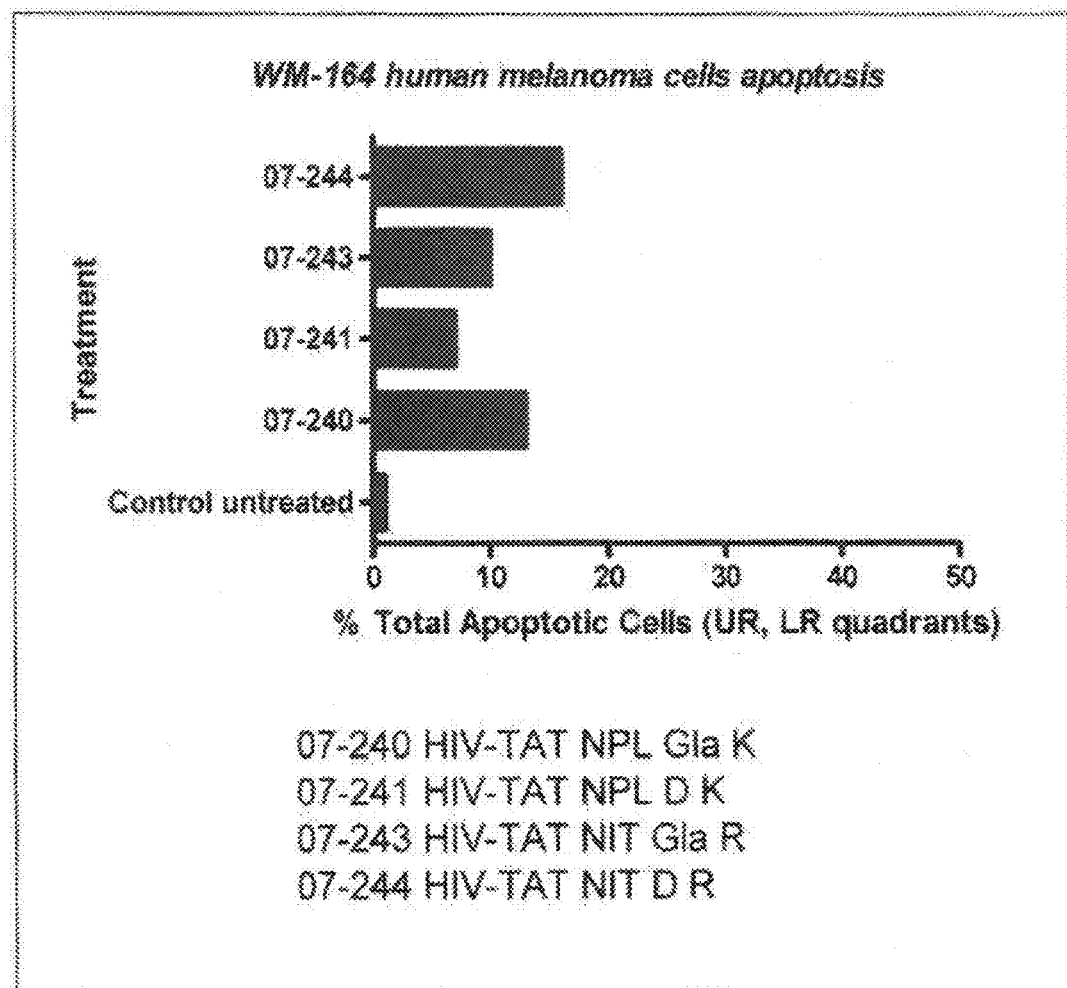

FIG. 22 illustrates a chart showing the effects of cyclic inhibiting peptides in accordance with an aspect of the invention on inducing apoptosis in melanoma cells.

DETAILED DESCRIPTION

Methods involving conventional molecular biology techniques are described herein. Such techniques are generally known in the art and are described in detail in methodology treatises, such as Current Protocols in Molecular Biology, ed. Ausubel et al., Greene Publishing and Wiley-Interscience, New York, 1992 (with periodic updates). Unless otherwise defined, all technical terms used herein have the same meaning as commonly understood by one of ordinary skill in the art to which the present invention pertains. Commonly understood definitions of molecular biology terms can be found in, for example, Rieger et al., Glossary of Genetics: Classical and Molecular, 5th Edition, Springer-Verlag: New York, 1991, and Lewin, Genes V, Oxford University Press: New York, 1994.

For convenience, certain terms employed in the specification, examples, and appended claims are collected here. Unless defined otherwise, all technical and scientific terms used herein have the same meaning as commonly understood by one of ordinary skill in the art to which this invention belongs.

The terms "peptide(s)", "protein(s)" and "polypeptide(s)" are used interchangeably herein. As used herein, "polypeptide" refers to any peptide or protein comprising two or more amino acids joined to each other by peptide bonds or modified peptide bonds (i.e., peptide isomers). "Polypeptide(s)" refers to both short chains, commonly referred as peptides, oligopeptides or oligomers, and to longer chains generally referred to as proteins.

The terms "polynucleotide sequence" and "nucleotide sequence" are also used interchangeably herein.

"Recombinant," as used herein, means that a protein is derived from a prokaryotic or eukaryotic expression system.

The term "wild type" refers to the naturally-occurring polynucleotide sequence encoding a protein, or a portion thereof, or protein sequence, or portion thereof, respectively, as it normally exists in vivo.

The term "mutant" refers to any change in the genetic material of an organism, in particular a change (i.e., deletion, substitution, addition, or alteration) in a wild type polynucleotide sequence or any change in a wild type protein. The term "variant" is used interchangeably with "mutant". Although it is often assumed that a change in the genetic material results in a change of the function of the protein, the terms "mutant" and "variant" refer to a change in the sequence of a wild type protein regardless of whether that change alters the function of the protein (e.g., increases, decreases, imparts a new function), or whether that change has no effect on the function of the protein (e.g., the mutation or variation is silent).

As used herein, the term "nucleic acid" refers to polynucleotides, such as deoxyribonucleic acid (DNA), and, where appropriate, ribonucleic acid (RNA). The term should also be understood to include, as equivalents, analogs of either, RNA or DNA made from nucleotide analogs, and, as applicable to the embodiment being described, single (sense or antisense) and double-stranded polynucleotides.

As used herein, the term "gene" or "recombinant gene" refers to a nucleic acid comprising an open reading frame encoding a polypeptide, including both exon and (optionally) intron sequences.

As used herein, the term "vector" refers to a nucleic acid molecule capable of transporting another nucleic acid to which it has been linked. Preferred vectors are those capable of autonomous replication and/or expression of nucleic acids to which they are linked. Vectors capable of directing the expression of genes to which they are operatively linked are referred to herein as "expression vectors".

A polynucleotide sequence (DNA, RNA) is "operatively linked" to an expression control sequence when the expression control sequence controls and regulates the transcription and translation of that polynucleotide sequence. The term "operatively linked" includes having an appropriate start signal (e.g., ATG) in front of the polynucleotide sequence to be expressed, and maintaining the correct reading frame to permit expression of the polynucleotide sequence under the control of the expression control sequence, and production of the desired polypeptide encoded by the polynucleotide sequence.

"Transcriptional regulatory sequence" is a generic term used throughout the specification to refer to nucleic acid sequences, such as initiation signals, enhancers, and promoters, which induce or control transcription of protein coding sequences with which they are operably linked. In some examples, transcription of a recombinant gene is under the control of a promoter sequence (or other transcriptional regulatory sequence) which controls the expression of the recombinant gene in a cell-type in which expression is intended. It will also be understood that the recombinant gene can be under the control of transcriptional regulatory sequences which are the same or which are different from those sequences, which control transcription of the naturally occurring form of a protein.

As used herein, the term "tissue-specific promoter" means a nucleic acid sequence that serves as a promoter, i.e., regulates expression of a selected nucleic acid sequence operably linked to the promoter, and which affects expression of the selected nucleic acid sequence in specific cells of a tissue, such as cells of epithelial cells. The term also covers so-called "leaky" promoters, which regulate expression of a selected nucleic acid primarily in one tissue, but cause expression in other tissues as well.

"Homology" and "identity" are used synonymously throughout and refer to sequence similarity between two peptides or between two nucleic acid molecules. Homology can be determined by comparing a position in each sequence, which may be aligned for purposes of comparison. When a position in the compared sequence is occupied by the same base or amino acid, then the molecules are homologous or identical at that position. A degree of homology or identity between sequences is a function of the number of matching or homologous positions shared by the sequences.

A "chimeric protein" or "fusion protein" is a fusion of a first amino acid sequence encoding a polypeptide with a second amino acid sequence defining a domain (e.g. polypeptide portion) foreign to and not substantially homologous with any domain of the first polypeptide. A chimeric protein may present a foreign domain which is found (albeit in a different protein) in an organism which also expresses the first protein, or it may be an "interspecies", "intergenic", etc. fusion of protein structures expressed by different kinds of organisms.

The term "isolated" as used herein with respect to nucleic acids, such as DNA or RNA, refers to molecules separated from other DNAs, or RNAs, respectively, which are present in the natural source of the macromolecule. The term isolated as used herein also refers to a nucleic acid or peptide that is substantially free of cellular material or culture medium when produced by recombinant DNA techniques, or chemical precursors or other chemicals when chemically synthesized. Moreover, an "isolated nucleic acid" is meant to include nucleic acid fragments, which are not naturally occurring as fragments and would not be found in the natural state.

The phrases "parenteral administration" and "administered parenterally" as used herein means modes of administration other than enteral and topical administration, usually by injection, and includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, subcapsular, subarachnoid, intraspinal and intrasternal injection and infusion.

The phrases "systemic administration," "administered systemically," "peripheral administration" and "administered peripherally" as used herein mean the administration of a compound, drug or other material other than directly into the central nervous system, such that it enters the animal's system and, thus, is subject to metabolism and other like processes, for example, subcutaneous administration.

The present invention relates generally to a method of modulating angiogenesis in a tissue, and thereby affecting events in the tissue that depend on angiogenesis. The method comprises administering to the tissue a therapeutically effective amount of an agent that modulates (e.g., inhibits or stimulates) complex formation of $\alpha_v\beta_3$ integrin and VEGFR2.

In accordance with one aspect of the invention, it was found that VEGF stimulation via activation of it major receptor VEGFR2 leads to the tyrosine phosphorylation of the cytoplasmic domain of $\alpha_v\beta_3$ integrin and integrin activation. In vivo and in vitro experiments show that tyrosine residues of the cytoplasmic domain of $\alpha_v\beta_3$ integrin are essential for complex formation with VEGFR2 and for sustained activation of VEGFR2. Impaired or inhibited cytoplamic $\beta_3$ integrin and VEGFR2 complex formation, reduced VEGFR2 activation and inhibited angiogenesis. The inhibition of $\alpha_v\beta_3$ integrin and VEGFR2 complex formation suppresses the function of both receptors. This is exemplified by reduced angiogenesis in mice with impaired $\beta_3$ tyrosine phosphorylation. A similar complex formation between $\alpha_v\beta_3$ integrin and VEGFR2 also occurs on tumor cells to promote tumor angiogenesis.

A population of cells or tissue that express $\alpha_v\beta_3$ integrin and VEGFR2, such as endothelial cells and tumor cells, can be contacted (e.g., directly or locally) with a therapeutically effective amount of an agent that upon localization to the cytoplasm of the cells can inhibit complex formation of $\alpha_v\beta_3$ integrin and VEGFR2. The inhibition of the complex formation of $\alpha_v\beta_3$ integrin and VEGFR2 can be used to suppress angiogenesis in endothelial cells and tumor-induced angiogenesis. The inhibition of the complex formation of $\alpha_v\beta_3$ integrin and VEGFR2 can inhibit endothelial cell motility, migration, and/or dispersal as well as inhibit capillary formation without affecting the adhesion of the endothelial cells.

Moreover, since it was found that tumors express $\alpha_v\beta_3$ integrin and VEGFR2 and over-express VEGF resulting in VEGF dependent autocrine loop, the agents in accordance with the present invention can potentially suppress tumor cell motility, migration, dispersal and/or metastases.

Additionally, complex formation of $\alpha_v\beta_3$ integrin and VEGFR2 occurs only in cells stimulated with VEGF or exposed to certain integrin ligands (e.g., vitronectin). Stimulation and over stimulation with VEGF is associated with pathological conditions, such as tumor angiogenesis. On normal quiescent endothelial cells, $\alpha_v\beta_3$ integrin may be expressed but it does not complex with VEGFR2. The method of the present invention can target activated endothelial cells associated with pathological conditions (e.g., pathological or aberrant angiogenesis) and tumor cells without targeting normal quiescent endothelial cells. This is in contrast to agents, such as VITAXIN, that block ligand binding to $\alpha_v\beta_3$ integrin or VEGFR2.

One aspect of the present invention therefore relates to a method of inhibiting pathological or aberrant angiogenesis by administering a therapeutically effective amount of agent that substantially inhibits complex formation of $\alpha_v\beta_3$ integrin and VEGFR2 but does not block or inhibit binding of natural ligands to VEGFR2 and $\alpha_v\beta_3$ integrin. As used herein, "inhibit", "inhibiting" or "inhibition" includes any measurable reproducible substantial reduction in: the interaction of $\alpha_v\beta_3$ integrin and VEGFR2; angiogenesis; symptoms of diseases correlated to angiogenesis; or any other activities complex formation of $\alpha_v\beta_3$ integrin and VEGFR2 may mediate. A substantial reduction is a "reproducible", i.e., consistently observed reduction in complex formation. A "substantial reduction" in terms of the present application is defined as a reproducible reduction (in complex formation of $\alpha_v\beta_3$ integrin and VEGFR2) of at least about 25%, or about 50%.

The present method of inhibiting angiogenesis in a tissue comprises contacting a tissue in which angiogenesis is occurring, or is at risk for occurring, with a composition comprising a therapeutically effective amount of an agent that is capable of inhibiting complex formation of $\alpha_v\beta_3$ integrin and VEGFR2 (i.e., $\alpha_v\beta_3$ integrin/VEGFR2 complex inhibiting agent). Thus, the method comprises administering to a patient a therapeutically effective amount of a physiologically tolerable composition containing an agent that is an inhibitor of complex formation of $\alpha_v\beta_3$ integrin and VEGFR2.

The dosage ranges for the administration of the agent depend upon the form of the inhibitor, and its potency, and are amounts large enough to produce the desired effect in which angiogenesis and the disease symptoms mediated by angiogenesis are ameliorated. The dosage should not be so large as to cause adverse side effects. The dosage can also be adjusted by the individual physician in the event of any complication.

A therapeutically effective amount is an amount of agent that is an inhibitor of complex formation of $\alpha_v\beta_3$ integrin and VEGFR2 sufficient to produce a measurable inhibition of angiogenesis in the tissue being treated, i.e., an angiogenesis-inhibiting amount. Inhibition of angiogenesis can be measured in situ by immunohistochemistry or by other methods known to one skilled in the art.

In one aspect of the invention, the agent can comprise a "complex inhibiting peptide", "inhibiting peptide", or "peptide inhibitor" that competes with $\alpha_v\beta_3$ integrin or VEGFR2 for interaction between the two receptors. The inhibiting peptide can have an amino acid sequence of about 5 to about 50 amino acids (e.g., about 5 to about 30 amino acids) that corresponds to an about 5 to about 50 amino acid cytoplasmic portion of the amino acid sequence of the VEGFR2 or $\alpha_v\beta_3$ integrin. By corresponding to, it is meant the inhibiting peptide has an amino acid sequence with a sequence identity that is substantially homologous to a portion of the amino acid sequence of $\alpha_v\beta_3$ integrin or VEGFR2. By substantially homologous, it is meant the inhibiting peptide has at least about 70%, about 80%, about 90% or about 100% sequence identity with a portion of the amino acid sequence of $\alpha_v\beta_3$ integrin or VEGFR2.

In one example, the inhibiting peptide can correspond to an about 5 to about 50 amino acid portion of the cytoplasmic domain of $\alpha_v\beta_3$ integrin or VEGFR2. Particular peptides include those that correspond to a cytoplasmic portion of $\alpha_v\beta_3$ integrin or VEGFR2 domain that includes a tyrosine residue. It was found that phosphorylation of tyrosine is required for complex formation of $\alpha_v\beta_3$ integrin and VEGFR2. A peptide comprising an amino acid sequence that corresponds to a portion of the amino acid sequence of $\alpha_v\beta_3$ integrin or VEGFR2 containing a tyrosine residue can compete with the tyrosine residue for phosphorylation.

In another example, the inhibiting peptide can consist of about 5 to about 50 amino acids and have an amino acid sequence substantially homologous to consecutive amino acids of a portion of the cytoplasmic doman of at least one of $\alpha_v\beta_3$ integrin or VEGFR2 that includes a tyrosine residue. The amino acid sequence of the inhibiting peptide can include a phosphorylated tyrosine residue or an amino acid residue that structurally mimics a phosphorylated tyrosine residue that is substituted for a corresponding tyrosine residue of the portion of the cytoplasmic domain of $\alpha_v\beta_3$ integrin or VEGFR2. By "substituted for a corresponding tyrosine residue" it is meant that the inhibiting peptide has an amino acid sequence substantially homologous to an amino acid sequence of $\alpha_v\beta_3$ integrin or VEGFR2, which includes a tyrosine residue, but the amino acid sequence of the inhibiting peptide includes a phosphorylated tyrosine residue or an amino acid residue that structurally mimics a phosphorylated tyrosine residue instead of the tyrosine residue.

Examples of amino acid residues that structurally mimic a phosphorylated tyrosine residue (i.e., structural mimetic amino acid residues of phosphorylated tyrosine residues) are γ-carboxyglutamic acid residue (Gla) and aspartic acid residue (D). Other examples of amino acid residues that structurally mimic phosphorylated tyrosine can be determined using in silico conformation screening techniques. Inhibiting peptides formed from the structural mimetic peptides of phosphorylated tyrosine can be readily screened using in vitro and in vivo inhibiting described in the Examples.

In an embodiment of the present invention, the inhibiting peptide can have an amino acid sequence of about 5 to about 30 amino acids and is substantially homologous to (or has a sequence identity of) a portion of the cytoplasmic domain of $\beta_3$ integrin that includes tyrosine 747. The inhibiting peptide can include a phosphorylated tyrosine residue or a structural mimetic amino acid residue of phosphorylated tyrosine instead of a tyrosine residue (i.e., tyrosine residue corresponding to tyrosine 747).

An example of an inhibiting peptide that can be used as an agent in accordance with the present invention has the amino acid sequence of: DTANNPLYpKEATSTFT (SEQ ID NO: 1), where Yp is a phophorylated tyrosine residue.

This inhibiting peptide corresponds to a portion of the cytoplasmic domain of $\beta_3$ integrin comprising the amino acid sequence DTANNPLYKEATSTFTNITYRGT. (SEQ ID NO: 2). The integrin $\beta_3$ cytoplasmic domain can include the amino acid sequence of KEFAKFEEERARAKWD-TANNPLYKEATSTFTNITYRGT (SEQ ID NO: 3).

Other examples of peptides having an amino acid sequence substantially homologous to consecutive amino acids of a portion of the cytoplasmic doman of at least one of $\alpha_v\beta_3$ integrin, which includes a tyrosine residue, and having a phosphorylated tyrosine residue or an amino acid residue, which structurally mimics a phosphorylated tyrosine residue, that is substituted for a corresponding tyrosine residue of the portion of the cytoplasmic domain of $\alpha_v\beta_3$ integrin, which can be used as an agent in accordance with the present invention can be selected from the group consisting of:

```
                                    (SEQ ID NO: 4)
       DTANNPLXKEATSTFT (SEQ ID NO: 5)
       NPLYpK;

(SEQ ID NO: 6)
       NITYpR;

(SEQ ID NO: 7)
       NPLXK;

(SEQ ID NO: 8)
       NITXR,
```

-continued

NPLDK; (SEQ ID NO: 9)

NITDR, (SEQ ID NO: 10)

where Yp is a phosphorylated tyrosine residue and X is a γ-carboxyglutamic acid residue.

Still other examples of peptides that can be used as an agent in accordance with the present invention and that correspond to a portion of the amino acid sequence of VEGRFR2 can comprises an amino acid sequence selected from group consisting of:

CMEEEEVCDPKFHYpDNTAGI; (SEQ ID NO: 11)

QTSGYQSGYHSDDTDTTVYpS; (SEQ ID NO: 12)

RDIYKDPDYpVRKGDARLPLK; (SEQ ID NO: 13)

WMAPETIFDRVYpTIQSDVWSFGV; (SEQ ID NO: 14)

LGASPYpPGVKIDEEFCRRLK; (SEQ ID NO: 15)

EGTRMRAPDYpTTPEMYQTML; (SEQ ID NO: 16)

GNLLQANAQQDGKDYpIVLPISETLSMEEDS; (SEQ ID NO: 17)

CMEEEEVCDPKFHXDNTAGI; (SEQ ID NO: 18)

QTSGYQSGYHSDDTDTTVXS; (SEQ ID NO: 19)

RDIYKDPDXVRKGDARLPLK; (SEQ ID NO: 20)

WMAPETIFDRVXTIQSDVWSFGV; (SEQ ID NO: 21)

LGASPXPGVKIDEEFCRRLK; (SEQ ID NO: 22)

EGTRMRAPDXTTPEMYQTML; (SEQ ID NO: 23)

GNLLQANAQQDGKDXIVLPISETLSMEEDS, (SEQ ID NO: 24)

CMEEEEVCDPKFHDDNTAGI; (SEQ ID NO: 25)

QTSGYQSGYHSDDTDTTVDS; (SEQ ID NO: 26)

RDIYKDPDDVRKGDARLPLK; (SEQ ID NO: 27)

WMAPETIFDRVDTIQSDVWSFGV; (SEQ ID NO: 28)

LGASPDPGVKIDEEFCRRLK; (SEQ ID NO: 29)

EGTRMRAPDDTTPEMYQTML; (SEQ ID NO: 30)
and

GNLLQANAQQDGKDDIVLPISETLSMEEDS; (SEQ ID NO: 31)

where Yp is a phosphorylated tyrosine residue and X is a γ-carboxyglutamic acid residue.

The peptides in accordance with the present invention can be subject to various changes, substitutions, insertions, and deletions where such changes provide for certain advantages in its use. In this regard, a peptide that is an inhibitor of complex formation of $\alpha_v\beta_3$ integrin and VEGFR2 corresponds to, rather than is identical to, the sequence of a recited peptide where one or more changes are made and it retains the ability to function as an inhibitor of complex formation of $\alpha_v\beta_3$ integrin and VEGFR2.

The peptides of the present invention can also be modified by natural processes, such as posttranslational processing, and/or by chemical modification techniques, which are known in the art. Modifications may occur anywhere in the peptide including the peptide backbone, the amino acid side-chains and the amino or carboxy termini. It will be appreciated that the same type of modification may be present in the same or varying degrees at several sites in a given peptide. Modifications comprise for example, without limitation, acetylation, acylation, addition of acetomidomethyl (Acm) group, ADP-ribosylation, amidation, covalent attachment to fiavin, covalent attachment to a heme moiety, covalent attachment of a nucleotide or nucleotide derivative, covalent attachment of a lipid or lipid derivative, covalent attachment of phosphatidylinositol, cross-linking, cyclization, disulfide bond formation, demethylation, formation of covalent cross-links, formation of cystine, formation of pyroglutamate, formylation, gamma-carboxylation, glycosylation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation and ubiquitination (for reference see, Protein-structure and molecular properties, 2nd Ed., T. E. Creighton, W. H. Freeman and Company, New-York, 1993).

Other type of peptide modifications may include for example, amino acid insertion (i.e., addition), deletion and substitution (i.e., replacement), either conservative or non-conservative in the polypeptide sequence where such changes do not substantially alter the overall competitive inhibitor ability of the polypeptide.

Peptides of the present invention may also include, for example, biologically active mutants, variants, fragments, chimeras, and analogues; fragments encompass amino acid sequences having truncations of one or more amino acids, wherein the truncation may originate from the amino terminus (N-terminus), carboxy terminus (C-terminus), or from the interior of the protein. Analogues of the invention involve an insertion or a substitution of one or more amino acids. Variants, mutants, fragments, chimeras and analogues may inhibit angiogenesis and/or promote tumor apoptosis (without being restricted to the present examples).

The peptide of the present invention can also be in the form of a conjugate protein or drug delivery construct having at least a transport subdomain(s) or moiety(ies) (i.e., transport moieties). The transport moieties can facilitate uptake of the complex inhibiting polypeptide into a mammalian (i.e., human or animal) tissue or cell. The transport moieties can be covalently linked to the polypeptdie. The covalent link can include a peptide bond or a labile bond (e.g., a bond readily cleavable or subject to chemical change in the interior target cell environment). Additionally, the transport moieties can be cross-linked (e.g., chemically cross-linked, UV cross-linked) to the polypeptide.

The transport moieties can be repeated more than once in the polypeptide. The repetition of a transport moiety may affect (e.g., increase) the uptake of the peptide by a desired cell. The transport moiety may also be located either at the amino-terminal region of an active agent or at its carboxy-terminal region or at both regions. The polypeptide of the present invention can also be in the form of a conjugate protein or drug delivery construct having at least a transport subdomain(s) or moiety(ies) (i.e., transport moieties).

In an aspect of the invention, the transport moiety can include at least one transport peptide sequence that allows the inhibiting peptides to penetrate into a cell, such as an endothelial cell or tumor cell. Examples of transport sequences that can be used in accordance with the present invention include a TAT-mediated protein delivery sequence (Vives (1997) 272: 16010-16017), polyargine sequences (Wender et al. 2000, PNAS 24: 13003-13008) and antennapedia (Derossi (1996) J. Biol. Chem. 271: 18188-18193). Other examples of known transport moieties, subdomains and the like are described in, for example, Canadian patent document No. 2,301,157 (conjugates containing homeodomain of antennapedia) as well as in U.S. Pat. Nos. 5,652,122, 5,670,617, 5,674,980, 5,747,641, and 5,804,604, all of which are incorporated herein by reference in their entirety, (conjugates containing amino acids of Tat HIV protein; herpes simplex virus-1 DNA binding protein VP22, a Histidine tag ranging in length from 4 to 30 histidine repeats, or a variation derivative or homologue thereof capable of facilitating uptake of the active cargo moiety by a receptor independent process.

A 16 amino acid region of the third alpha-helix of antennapedia homeodomain has also been shown to enable proteins (made as fusion proteins) to cross cellular membranes (PCT international publication number WO 99/11809 and Canadian application No.: 2,301,157 (Crisanti et al,) incorporated by reference in their entirety). Similarly, HIV Tat protein was shown to be able to cross cellular membranes (Frankel A. D. et al., Cell, 55: 1189).

In addition, the transport moiety(ies) can include polypeptides having a basic amino acid rich region covalently linked to the inhibiting peptide. As used herein, the term "basic amino acid rich region" relates to a region of a protein with a high content of the basic amino acids such as arginine, histidine, asparagine, glutamine, lysine. A "basic amino acid rich region" may have, for example 15% or more (up to 100%) of basic amino acids. In some instance, a "basic amino acid rich region" may have less than 15% of basic amino acids and still function as a transport agent region. More preferably, a basic amino acid region will have 30% or more (up to 100%) of basic amino acids.

The transport moiety(ies) may further include a proline rich region. As used herein, the term proline rich region refers to a region of a polypeptide with 5% or more (up to 100%) of proline in its sequence. In some instance, a proline rich region may have between 5% and 15% of prolines. Additionally, a proline rich region refers to a region, of a polypeptide containing more prolines than what is generally observed in naturally occurring proteins (e.g., proteins encoded by the human genome). Proline rich regions of the present invention can function as a transport agent region.

Other transport sequences that have been tested in other contexts, (i.e., to show that they work through the use of reporter sequences), are known. One transport peptide, AAVLLPVLLAAP (SEQ ID NO: 32), is rich in proline. This transport made as a GST-MTS fusion protein and is derived from the h region of the Kaposi FGF signal sequence (Royas et al. (1998) Nature Biotech. 16: 370-375). Another example is the sperm fertiline alpha peptide, HPIQIAAFLARIPPIS-SIGTCILK (SEQ ID NO: 33) (See Pecheur, J. Sainte-Marie, A. Bienvenuje, D. Hoekstra. 1999. J. Membrane Biol. 167: 1-17).

In one example, the inhibiting peptide can be provided as a fusion protein (polypeptide) that includes a carboxy terminal inhibiting peptide and an amino terminal transport moiety. The amino terminal transport moiety can be a transport subdomain of HIV (e.g., HIV-1) TAT protein, homeoprotein transport sequence, a Histidine tag or a functional derivative and analogues thereof (i.e. pharmaceutically acceptable chemical equivalents thereof). In another example, the fusion protein (polypeptide) can include a carboxy terminal inhibiting peptide and an amino terminal transport moiety that includes a homeodomain of antennapedia.

In another aspect of the invention, the inhibiting peptide can be non-covalently linked to a transfection agent. An example of a non-covalently linked polypeptide transfection agent is the Chariot protein delivery system (See U.S. Pat. No. 6,841,535; Morris et al. (1999) J. Biol. Chem. 274(35): 24941-24946; and Morris et al. (2001) Nature Biotech. 19:1173-1176), all herein incorporated by reference in their entirety.

The Chariot protein delivery system includes a peptide transfection agent that can non-covalently complex with the inhibit peptide of the present invention. Upon cellular internalization, the transfection agent dissociates and the inhibiting peptide is free to complex formation of $av\beta 3$ integrin and VEGFR2. The complex of the Chariot transfection peptide and the inhibiting peptide can be delivered to and internalized by mammalian cells allowing for higher dosages of therapeutics to be delivered to the site of pathology.

In an aspect of the invention, the transport moiety can include at least one transport peptide, such as the TAT-mediated protein delivery sequence described in Vives (1997) 272: 16010-16017. An example of a peptide in accordance with the present that includes a cell penetrating peptide can have the following amino acid sequence <u>YGKKRRQRRRG</u> DTANNPLYpKEATSTFT (SEQ ID NO: 34), where the underlined portion comprises the cell penetrating peptide portion.

Other examples of inhibiting peptides in accordance with the present invention that include a cell penetrating sequence can have the following amino acid sequences:

<u>RR</u>(NPLDK) (SEQ ID NO: 35)

<u>RR</u>(NITDR) (SEQ ID NO: 36)

<u>RRRKKRKRRR</u>(NPLDK) (SEQ ID NO: 37)

<u>RRRKKRKRRR</u>(NITDR) (SEQ ID NO: 38)

<u>RR</u>(NPLXK) (SEQ ID NO: 39)

<u>RR</u>(NITXR) (SEQ ID NO: 40)

<u>RRRKKRKRRR</u>(NPLXK); (SEQ ID NO: 41)
and

<u>RRRKKRKRRR</u>(NITXR) (SEQ ID NO: 42)

where X is a γ-carboxyglutamic acid residue, the underlined portion comprises the cell penetrating peptide portion, and the portion of the peptide in parentheses is a cyclic inhibiting peptide linked with a disulfide bridge.

Any peptide or compound of the present invention may also be used in the form of a pharmaceutically acceptable salt. Acids, which are capable of forming salts with the peptides of the present invention, include inorganic acids such as trifluoroacetic acid (TFA) hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like.

Bases capable of forming salts with the peptides of the present invention include inorganic bases such as sodium hydroxide, ammonium hydroxide, potassium hydroxide and the like; and organic bases such as mono-, di- and tri-alkyl and aryl amines (e.g., triethylamine, diisopropyl amine, methyl amine, dimethyl amine and the like) and optionally substituted ethanolamines (e.g. ethanolamine, diethanolamine and the like).

A peptide of the present invention also referred to herein as a subject peptide, can be synthesized by any of the techniques that are known to those skilled in the polypeptide art, including recombinant DNA techniques. Synthetic chemistry techniques, such as a solid-phase Merrifield-type synthesis, can be used for reasons of purity, antigenic specificity, freedom from undesired side products, ease of production and the like. A summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, Adv. Enzymol., 32:221-96, 1969; Fields et al., in J. Peptide Protein Res., 35:161-214, 1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

In another aspect, the αvβ3 integrin/VEGFR2 complex inhibiting peptides in accordance with the present invention can be provided in a pharmaceutical compositions. The pharmaceutical compositions will generally comprise an effective amount of agent, dissolved or dispersed in a pharmaceutically acceptable carrier or aqueous medium. Combined therapeutics are also contemplated, and the same type of underlying pharmaceutical compositions may be employed for both single and combined medicaments.

The phrases "pharmaceutically or pharmacologically acceptable" refer to molecular entities and compositions that do not produce an adverse, allergic or other untoward reaction when administered to an animal, or a human, as appropriate. Veterinary uses are equally included within the invention and "pharmaceutically acceptable" formulations include formulations for both clinical and/or veterinary use.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. For human administration, preparations should meet sterility, pyrogenicity, general safety and purity standards as required by FDA Office of Biologics standards. Supplementary active ingredients can also be incorporated into the compositions.

"Unit dosage" formulations are those containing a dose or sub-dose of the administered ingredient adapted for a particular timed delivery. For example, exemplary "unit dosage" formulations are those containing a daily dose or unit or daily sub-dose or a weekly dose or unit or weekly sub-dose and the like.

In an aspect of the invention, the αvβ3 integrin/VEGFR2 complex inhibiting peptides of the present invention can be formulated for parenteral administration, e.g., formulated for injection via the intravenous, intramuscular, sub-cutaneous, transdermal, intravitreal, or other such routes, including peristaltic administration and direct instillation into a tumor or disease site (intracavity administration). The preparation of an aqueous composition that contains such an αvβ3 integrin/VEGFR2 complex modulating agent as an active ingredient will be known to those of skill in the art in light of the present disclosure. Typically, such compositions can be prepared as injectables, either as liquid solutions or suspensions; solid forms suitable for using to prepare solutions or suspensions upon the addition of a liquid prior to injection can also be prepared; and the preparations can also be emulsified.

The pharmaceutical forms that can be used for injectable use include sterile aqueous solutions or dispersions; formulations including sesame oil, peanut oil or aqueous propylene glycol; and sterile powders for the extemporaneous preparation of sterile injectable solutions or dispersions. In all cases, the form should be sterile and fluid to the extent that syringability exists. It should be stable under the conditions of manufacture and storage and should be preserved against the contaminating action of microorganisms, such as bacteria and fungi.

Compositions of the αvβ3 integrin/VEGFR2 complex inhibiting peptides can be formulated into a sterile aqueous composition in a neutral or salt form. Solutions as free base or pharmacologically acceptable salts can be prepared in water suitably mixed with a surfactant, such as hydroxypropylcellulose. Pharmaceutically acceptable salts, include the acid addition salts (formed with the free amino groups of the protein), and those that are formed with inorganic acids such as, for example, hydrochloric or phosphoric acids, or such organic acids as acetic, trifluoroacetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Examples of carriers include solvents and dispersion media containing, for example, water, ethanol, polyol (for example, glycerol, propylene glycol, and liquid polyethylene glycol, and the like), suitable mixtures thereof, and vegetable oils. In many cases, it will be preferable to include isotonic agents, for example, sugars or sodium chloride. The proper fluidity can be maintained, for example, by the use of a coating, such as lecithin, by the maintenance of the required particle size in the case of dispersion and/or by the use of surfactants.

Under ordinary conditions of storage and use, all such preparations should contain a preservative to prevent the growth of microorganisms. The prevention of the action of microorganisms can be brought about by various antibacterial and antifungal agents, for example, parabens, chlorobutanol, phenol, sorbic acid, thimerosal, and the like. Prolonged absorption of the injectable compositions can be brought about by the use in the compositions of agents delaying absorption, for example, aluminum monostearate and gelatin.

Prior to or upon formulation, the $\alpha v\beta 3$ integrin/VEGFR2 complex inhibiting peptides can be extensively dialyzed to remove undesired small molecular weight molecules, and/or lyophilized for more ready formulation into a desired vehicle, where appropriate. Sterile injectable solutions are prepared by incorporating the active agents in the required amount in the appropriate solvent with various of the other ingredients enumerated above, as desired, followed by filtered sterilization. Generally, dispersions are prepared by incorporating the various sterilized active ingredients into a sterile vehicle that contains the basic dispersion medium and the required other ingredients from those enumerated above.

In the case of sterile powders for the preparation of sterile injectable solutions, the preferred methods of preparation are vacuum-drying and freeze-drying techniques that yield a powder of the active ingredient, plus any additional desired ingredient from a previously sterile-filtered solution thereof.

Examples of pharmaceutical compositions in accordance with the invention will generally include an amount of the $\alpha v\beta 3$ integrin/VEGFR2 complex inhibiting agent admixed with an acceptable pharmaceutical diluent or excipient, such as a sterile aqueous solution, to give a range of final concentrations, depending on the intended use. The techniques of preparation are generally well known in the art as exemplified by Remington's Pharmaceutical Sciences, 16th Ed. Mack Publishing Company, 1980, incorporated herein by reference. Moreover, for human administration, preparations should meet sterility, pyrogenicity, general safety and purity standards as required by FDA Office of Biological Standards. Upon formulation, the polypeptide or conjugate solutions will be administered in a manner compatible with the dosage formulation and in such amount as is therapeutically effective.

Formulations of the $\alpha v\beta 3$ integrin/VEGFR2 complex inhibiting agents are easily administered in a variety of dosage forms, such as the type of injectable solutions described above, but other pharmaceutically acceptable forms are also contemplated, e.g., tablets, pills, capsules or other solids for oral administration, suppositories, pessaries, nasal solutions or sprays, aerosols, inhalants, topical formulations, liposomal forms and the like. The type of form for administration will be matched to the disease or disorder to be treated.

Pharmaceutical "slow release" capsules or "sustained release" compositions or preparations may be used and are generally applicable. Slow release formulations are generally designed to give a constant drug level over an extended period and may be used to deliver $\alpha v\beta 3$ integrin/VEGFR2 complex modulating agents in accordance with the present invention. The slow release formulations are typically implanted in the vicinity of the disease site, for example, at the site of a tumor.

Examples of sustained-release preparations include semipermeable matrices of solid hydrophobic polymers containing the polypeptide or immunoconjugate, which matrices are in the form of shaped articles, e.g., films or microcapsule. Examples of sustained-release matrices include polyesters; hydrogels, for example, poly(2-hydroxyethyl-methacrylate) or poly(vinylalcohol); polylactides, e.g., U.S. Pat. No. 3,773,919; copolymers of L-glutamic acid and $\gamma$ ethyl-L-glutamate; non-degradable ethylene-vinyl acetate; degradable lactic acid-glycolic acid copolymers, such as the Lupron Depot (injectable microspheres composed of lactic acid-glycolic acid copolymer and leuprolide acetate); and poly-D-(−)-3-hydroxybutyric acid.

While polymers such as ethylene-vinyl acetate and lactic acid-glycolic acid enable release of molecules for over 100 days, certain hydrogels release proteins for shorter time periods. When encapsulated polypeptides remain in the body for a long time, they may denature or aggregate as a result of exposure to moisture at 37° C., thus reducing biological activity and/or changing immunogenicity. Rational strategies are available for stabilization depending on the mechanism involved. For example, if the aggregation mechanism involves intermolecular S—S bond formation through thio-disulfide interchange, stabilization is achieved by modifying sulfhydryl residues, lyophilizing from acidic solutions, controlling moisture content, using appropriate additives, developing specific polymer matrix compositions, and the like.

In certain embodiments, liposomes and/or nanoparticles may also be employed with the $\alpha v\beta 3$ integrin/VEGFR2 complex inhibiting agents. The formation and use of liposomes is generally known to those of skill in the art, as summarized below.

Liposomes are formed from phospholipids that are dispersed in an aqueous medium and spontaneously form multilamellar concentric bilayer vesicles (also termed multilamellar vesicles (MLVs). MLVs generally have diameters of from 25 nm to 4 μm. Sonication of MLVs results in the formation of small unilamellar vesicles (SUVs) with diameters in the range of 200 to 500 μm, containing an aqueous solution in the core.

Phospholipids can form a variety of structures other than liposomes when dispersed in water, depending on the molar ratio of lipid to water. At low ratios, the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. Varying the liposome formulation can alter which mechanism is operative, although more than one may operate at the same time.

Nanocapsules can generally entrap compounds in a stable and reproducible way. To avoid side effects due to intracellular polymeric overloading, such ultrafine particles (sized around 0.1 μm) should be designed using polymers able to be degraded in vivo. Biodegradable polyalkyl-cyanoacrylate nanoparticles that meet these requirements are contemplated for use in the present invention, and such particles may be are easily made.

In an aspect of the invention, the αvβ3 integrin/VEGFR2 complex inhibiting agents may be advantageously employed in the preparation of pharmaceutical compositions suitable for use as ophthalmic solutions, including those for intravitreal and/or intracameral administration. For the treatment of any of the foregoing or other disorders a composition comprising αvβ3 integrin/VEGFR2 complex inhibiting agents of the invention can be administered to the eye or eyes of the subject in need of treatment in the form of an ophthalmic preparation prepared in accordance with conventional pharmaceutical practice, see for example "Remington's Pharmaceutical Sciences" 15th Edition, pages 1488 to 1501 (Mack Publishing Co., Easton, Pa.).

The ophthalmic preparation can contain the αvβ3 integrin/VEGFR2 complex inhibiting peptides in a pharmaceutically acceptable solution, suspension or ointment. Some variation in concentration will necessarily occur, depending on the particular compound employed, the condition of the subject to be treated and the like, and the person responsible for treatment will determine the most suitable concentration for the individual subject. The ophthalmic preparation will preferably be in the form of a sterile aqueous solution containing, if desired, additional ingredients, for example preservatives, buffers, tonicity agents, antioxidants and stabilizers, nonionic wetting or clarifying agents, viscosity-increasing agents and the like.

Examples of preservatives for use in such a solution include benzalkonium chloride, benzethonium chloride, chlorobutanol, thimerosal and the like. Suitable buffers include boric acid, sodium and potassium bicarbonate, sodium and potassium borates, sodium and potassium carbonate, sodium acetate, sodium biphosphate and the like, in amounts sufficient to maintain the pH at between about pH 6 and pH 8, and preferably, between about pH 7 and pH 7.5. Suitable tonicity agents are dextran 40, dextran 70, dextrose, glycerin, potassium chloride, propylene glycol, sodium chloride, and the like, such that the sodium chloride equivalent of the ophthalmic solution is in the range 0.9 plus or minus 0.2%.

Examples of antioxidants and stabilizers include sodium bisulfite, sodium metabisulfite, sodium thiosulfite, thiourea and the like. Examples of wetting and clarifying agents include polysorbate 80, polysorbate 20, poloxamer 282 and tyloxapol. Suitable viscosity-increasing agents include dextran 40, dextran 70, gelatin, glycerin, hydroxyethylcellulose, hydroxmethylpropylcellulose, lanolin, methylcellulose, petrolatum, polyethylene glycol, polyvinyl alcohol, polyvinylpyrrolidone, carboxymethylcellulose and the like. The ophthalmic preparation will be administered topically to the eye of the subject in need of treatment by conventional methods, for example in the form of drops or by bathing the eye in the ophthalmic solution.

In another aspect, the αvβ3 integrin/VEGFR2 complex modulating agents can be formulated for topical administration. Topical formulations include those for delivery via the mouth (buccal) and through the skin. "Topical delivery systems" also include transdermal patches containing the ingredient to be administered. Delivery through the skin can further be achieved by iontophoresis or electrotransport, if desired.

Formulations suitable for topical administration in the mouth include lozenges comprising the ingredients in a flavored basis, usually sucrose and acacia or tragacanth; pastilles comprising the active ingredient in an inert basis such as gelatin and glycerin, or sucrose and acacia; and mouthwashes comprising the ingredient to be administered in a suitable liquid carrier.

Formulations suitable for topical administration to the skin include ointments, creams, gels and pastes comprising the ingredient to be administered in a pharmaceutical acceptable carrier. The formulation of αvβ3 integrin/VEGFR2 complex modulating agents for topical use, such as in creams, ointments and gels, includes the preparation of oleaginous or water-soluble ointment bases, as is well known to those in the art. For example, these compositions may include vegetable oils, animal fats, and more preferably, semisolid hydrocarbons obtained from petroleum. Particular components used may include white ointment, yellow ointment, cetyl esters wax, oleic acid, olive oil, paraffin, petrolatum, white petrolatum, spermaceti, starch glycerite, white wax, yellow wax, lanolin, anhydrous lanolin and glyceryl monostearate. Various water-soluble ointment bases may also be used, including glycol ethers and derivatives, polyethylene glycols, polyoxyl 40 stearate and polysorbates.

Formulations for rectal administration may be presented as a suppository with a suitable base comprising, for example, cocoa butter or a salicylate. Formulations suitable for vaginal administration may be presented as pessaries, tampons, creams, gels, pastes, foams or spray formulations containing in addition to the active ingredient such carriers as are known in the art to be appropriate.

Local delivery via the nasal and respiratory routes is contemplated for treating various conditions. These delivery routes are also suitable for delivering agents into the systemic circulation. Formulations of active ingredients in carriers suitable for nasal administration are therefore also included within the invention, for example, nasal solutions, sprays, aerosols and inhalants. Where the carrier is a solid, the formulations include a coarse powder having a particle size, for example, in the range of 20 to 500 microns, which is administered, e.g., by rapid inhalation through the nasal passage from a container of the powder held close up to the nose.

Examples of formulations wherein the carrier is a liquid are useful in nasal administration. Nasal solutions are usually aqueous solutions designed to be administered to the nasal passages in drops or sprays and are prepared so that they are similar in many respects to nasal secretions, so that normal ciliary action is maintained. In addition, antimicrobial preservatives, similar to those used in ophthalmic preparations, and appropriate drug stabilizers, if required, may be included in the formulation. Various commercial nasal preparations are known and include, for example, antibiotics and antihistamines and are used for asthma prophylaxis.

Inhalations and inhalants are pharmaceutical preparations designed for delivering a drug or compound into the respiratory tree of a patient. A vapor or mist is administered and reaches the affected area. This route can also be employed to deliver agents into the systemic circulation. Inhalations may be administered by the nasal or oral respiratory routes. The administration of inhalation solutions is only effective if the droplets are sufficiently fine and uniform in size so that the mist reaches the bronchioles.

Another group of products, also known as inhalations, and sometimes called insufflations, comprises finely powdered or liquid drugs that are carried into the respiratory passages by the use of special delivery systems, such as pharmaceutical aerosols, that hold a solution or suspension of the drug in a liquefied gas propellant. When released through a suitable valve and oral adapter, a metered does of the inhalation is propelled into the respiratory tract of the patient. Particle size is of major importance in the administration of this type of preparation. It has been reported that the optimum particle size for penetration into the pulmonary cavity is of the order of 0.5 to 7 μm. Fine mists are produced by pressurized aerosols and hence their use in considered advantageous.

In accordance with another aspect of the present invention, the αvβ3 integrin/VEGFR2 complex inhibiting agents may be used to treat animals and patients with aberrant angiogenesis, such as that contributing to a variety of diseases and disorders. The most prevalent and/or clinically important of these, outside the field of cancer treatment, include arthritis, rheumatoid arthritis, psoriasis, atherosclerosis, diabetic retinopathy, age-related macular degeneration, Grave's disease, vascular restenosis, including restenosis following angioplasty, arteriovenous malformations (AVM), meningioma, hemangioma and neovascular glaucoma. Other potential targets for intervention include angiofibroma, atherosclerotic plaques, corneal graft neovascularization, hemophilic joints, hypertrophic scars, osler-weber syndrome, pyogenic granuloma retrolental fibroplasia, scleroderma, trachoma, vascular adhesions, synovitis, dermatitis, various other inflammatory diseases and disorders, and even endometriosis. Further diseases and disorders that are treatable by the invention, and the unifying basis of such angiogenic disorders, are set forth below.

One disease in which angiogenesis is involved is rheumatoid arthritis, wherein the blood vessels in the synovial lining of the joints undergo angiogenesis. In addition to forming new vascular networks, the endothelial cells release factors and reactive oxygen species that lead to pannus growth and cartilage destruction. The factors involved in angiogenesis may actively contribute to, and help maintain, the chronically inflamed state of rheumatoid arthritis. Factors associated with angiogenesis also have a role in osteoarthritis, contributing to the destruction of the joint.

Another example of a disease mediated by angiogenesis is ocular neovascular disease. This disease is characterized by invasion of new blood vessels into the structures of the eye, such as the choroid, retina, or cornea. It is the most common cause of blindness and is involved in approximately twenty eye diseases. In age-related macular degeneration, the associated visual problems are caused by an ingrowth of chorioidal capillaries through defects in Bruch's membrane with proliferation of fibrovascular tissue beneath the retinal pigment epithelium. Angiogenic damage is also associated with diabetic retinopathy, retinopathy of prematurity, corneal graft rejection, neovascular glaucoma and retrolental fibroplasia.

Other diseases associated with corneal neovascularization include, but are not limited to, epidemic keratoconjunctivitis, Vitamin A deficiency, contact lens overwear, atopic keratitis, superior limbic keratitis, pterygium keratitis sicca, sjogrens, acne rosacea, phylectenulosis, syphilis, Mycobacteria infections, lipid degeneration, chemical burns, bacterial ulcers, fungal ulcers, Herpes simplex infections, Herpes zoster infections, protozoan infections, Kaposi sarcoma, Mooren ulcer, Terrien's marginal degeneration, mariginal keratolysis, rheumatoid arthritis, systemic lupus, polyarteritis, trauma, Wegeners sarcoidosis, Scleritis, Steven's Johnson disease, periphigoid radial keratotomy, and corneal graph rejection.

Diseases associated with retinal/choroidal neovascularization include, but are not limited to, diabetic retinopathy, macular degeneration, sickle cell anemia, sarcoid, syphilis, pseudoxanthoma elasticum, Pagets disease, vein occlusion, artery occlusion, carotid obstructive disease, chronic uveitis/vitritis, mycobacterial infections, Lyme's disease, systemic lupus erythematosis, retinopathy of prematurity, Eales disease, Bechets disease, infections causing a retinitis or choroiditis, presumed ocular histoplasmosis, Bests disease, myopia, optic pits, Stargarts disease, pars planitis, chronic retinal detachment, hyperviscosity syndromes, toxoplasmosis, trauma and post-laser complications.

Other diseases include, but are not limited to, diseases associated with rubeosis and diseases caused by the abnormal proliferation of fibrovascular or fibrous tissue including all forms of proliferative vitreoretinopathy.

Chronic inflammation also involves pathological angiogenesis. Such disease states as ulcerative colitis and Crohn's disease show histological changes with the ingrowth of new blood vessels into the inflamed tissues. Bartonellosis, a bacterial infection found in South America, can result in a chronic stage that is characterized by proliferation of vascular endothelial cells.

Another pathological role associated with angiogenesis is found in atherosclerosis. The plaques formed within the lumen of blood vessels have been shown to have angiogenic stipulatory activity. VEGF expression in human coronary atherosclerotic lesions has been demonstrated. This evidences the pathophysiological significance of VEGF in the progression of human coronary atherosclerosis, as well as in recanalization processes in obstructive coronary diseases. The present invention provides an effective treatment for such conditions.

One of the most frequent angiogenic diseases of childhood is the hemangioma. In most cases, the tumors are benign and regress without intervention. In more severe cases, the tumors progress to large cavernous and infiltrative forms and create clinical complications. Systemic forms of hemangiomas, the hemangiomatoses, have a high mortality rate.

Therapy-resistant hemangiomas exist that cannot be treated with therapeutics currently in use.

Angiogenesis is also responsible for damage found in hereditary diseases such as Osler-Weber-Rendu disease, or hereditary hemorrhagic telangiectasia. This is an inherited disease characterized by multiple small angiomas, tumors of blood or lymph vessels. The angiomas are found in the skin and mucous membranes, often accompanied by epistaxis (nosebleeds) or gastrointestinal bleeding and sometimes with pulmonary or hepatic arteriovenous fistula.

Angiogenesis is also involved in normal physiological processes such as reproduction and wound healing. Angiogenesis is an important step in ovulation and also in implantation of the blastula after fertilization. Prevention of angiogenesis could be used to induce amenorrhea, to block ovulation or to prevent implantation by the blastula.

In wound healing, excessive repair or fibroplasia can be a detrimental side effect of surgical procedures and may be caused or exacerbated by angiogenesis. Adhesions are a frequent complication of surgery and lead to problems such as small bowel obstruction.

Diseases and disorders characterized by undesirable vascular permeability can also be treated by the present invention. These include edema associated with brain tumors, ascites associated with malignancies, Meigs' syndrome, lung inflammation, nephrotic syndrome, pericardial effusion and pleural effusion, as disclosed in WO 98/16551, specifically incorporated herein by reference.

Each of the foregoing diseases and disorders, along with all types of tumors, as described in the following sections, can be effectively treated by the present invention in accordance with the knowledge in the art, as disclosed in, e.g., U.S. Pat. No. 5,712,291 (specifically incorporated herein by reference), that unified benefits result from the application of anti-angiogenic strategies to the treatment of angiogenic diseases.

The αvβ3 integrin/VEGFR2 complex inhibiting peptides of the invention can also be utilized in the treatment of tumors. Tumors in which angiogenesis is important include malignant tumors, and benign tumors, such as acoustic neuroma, neurofibroma, trachoma and pyogenic granulomas. Angiogenesis is particularly prominent in solid tumor formation and metastasis. However, angiogenesis is also associated with blood-born tumors, such as leukemias, and various acute or chronic neoplastic diseases of the bone marrow in which unrestrained proliferation of white blood cells occurs, usually accompanied by anemia, impaired blood clotting, and enlargement of the lymph nodes, liver, and spleen. Angiogenesis also plays a role in the abnormalities in the bone marrow that give rise to leukemia-like tumors.

Angiogenesis is important in two stages of tumor metastasis. In the vascularization of the primary tumor, angiogenesis allows cells to enter the blood stream and to circulate throughout the body. After tumor cells have left the primary site, and have settled into the secondary, metastasis site, angiogenesis must occur before the new tumor can grow and expand. Therefore, prevention of angiogenesis can prevent metastasis of tumors and contain the neoplastic growth at the primary site, allowing treatment by other therapeutics, particularly, therapeutic agent-targeting agent constructs.

The αvβ3 integrin/VEGFR2 complex inhibiting peptides provided by this invention are thus broadly applicable to the treatment of any malignant tumor having a vascular component. In using the αvβ3 integrin/VEGFR2 complex inhibiting peptides of the invention in the treatment of tumors, particularly vascularized, malignant tumors, the agents may be used alone or in combination with, e.g., chemotherapeutic, radiotherapeutic, apoptopic, anti-angiogenic agents and/or immunotoxins or coaguligands.

Typical vascularized tumors for treatment are the solid tumors, particularly carcinomas, which require a vascular component for the provision of oxygen and nutrients. Exemplary solid tumors that may be treated using the invention include, but are not limited to, carcinomas of the lung, breast, ovary, stomach, pancreas, larynx, esophagus, testes, liver, parotid, biliary tract, colon, rectum, cervix, uterus, endometrium, kidney, bladder, prostate, thyroid, squamous cell carcinomas, adenocarcinomas, small cell carcinomas, melanomas, gliomas, glioblastomas, neuroblastomas, and the like. WO 98/45331 is also incorporated herein by reference to further exemplify the variety of tumor types that may be effectively treated using an anti-VEGF polypeptide.

Knowledge of the role of angiogenesis in the maintenance and metastasis of tumors has led to a prognostic indicator for cancers such as breast cancer. The amount of neovascularization found in the primary tumor was determined by counting the microvessel density in the area of the most intense neovascularization in invasive breast carcinoma. A high level of microvessel density was found to correlate with tumor recurrence. Control of angiogenesis by the therapies of the present invention will reduce or negate the recurrence of such tumors.

The present invention is contemplated for use in the treatment of any patient that presents with a solid tumor. In light of the specific properties of the αvβ3 integrin/VEGFR2 complex inhibiting peptides, the therapeutics of the present invention will have reduced side effects. Particular advantages will result in the maintenance or enhancement of host immune responses against the tumor, as mediated by macrophages, and in the lack of adverse effects on bone tissue. The invention will thus be the anti-angiogenic therapy of choice for the treatment of pediatric cancers and patients having, or at risk for developing, osteoporosis and other bone deficiencies.

Although all malignancies and solid tumors may be treated by the invention, the unconjugated polypeptides comprising αvβ3 integrin/VEGFR2 complex inhibiting peptides are particularly contemplated for use in treating patients with more angiogenic tumors, or patients at risk for metastasis.

The present invention is also intended as a preventative or prophylactic treatment. These aspects of the invention include the ability of the invention to treat patients presenting with a primary tumor who may have metastatic tumors, or tumor cells in the earlier stages of metastatic tumor seeding. As an anti-angiogenic strategy, the present invention may also be used to prevent tumor development in subjects at moderate or high risk for developing a tumor, as based upon prognostic tests and/or close relatives suffering from a hereditary cancer.

Therapeutically effective doses of the αvβ3 integrin/VEGFR2 complex inhibiting peptides are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors are widely used in pre-clinical testing.

In using the αvβ3 integrin/VEGFR2 complex inhibiting peptides in anti-angiogenic therapies, one can also draw on other published data in order to assist in the formulation of doses for clinical treatment. For instance, although the agents and methods of the present invention have distinct advantages over those in the art, the information in the literature concerning treatment with other polypeptides and tyrosine kinase inhibitors can still be used in combination with the data and teaching in the present application to design and/or optimize treatment protocols and doses.

Any dose, or combined medicament of the αvβ3 integrin/VEGFR2 complex inhibiting peptides, that results in any consistently detectable anti-angiogenic effect, inhibition of metastasis, tumor vasculature destruction, tumor thrombosis, necrosis and/or general anti-tumor effect will define a useful invention. The present invention may also be effective against vessels downstream of the tumor, i.e., target at least a sub-set of the draining vessels, particularly as cytokines released from the tumor will be acting on these vessels, changing their antigenic profile.

It will also be understood that even in such circumstances where the anti-angiogenic and/or tumor effects of the dose, or combined therapy of the αvβ3 integrin/VEGFR2 complex inhibiting peptides, are towards the low end of the intended therapeutic range, it may be that this therapy is still equally or even more effective than all other known therapies in the context of the particular tumor target or patient. It is unfortunately evident to a clinician that certain tumors and conditions cannot be effectively treated in the intermediate or long term, but that does not negate the usefulness of the present therapy, particularly where it is at least about as effective as the other strategies generally proposed.

In designing appropriate doses of αvβ3 integrin/VEGFR2 complex inhibiting peptides for the treatment of vascularized tumors, one may readily extrapolate from the knowledge in the literature in order to arrive at appropriate doses for clinical administration. To achieve a conversion from animal to human doses, one would account for the mass of the agents administered per unit mass of the experimental animal and, preferably, account for the differences in the body surface area (m2) between the experimental animal and the human patient. All such calculations are well known and routine to those of ordinary skill in the art.

It will be understood that lower doses may be more appropriate in combination with other agents, and that high doses can still be tolerated.

The intention of the therapeutic regimens of the present invention is generally to produce significant anti-tumor effects while still keeping the dose below the levels associated with unacceptable toxicity. In addition to varying the dose itself, the administration regimen can also be adapted to optimize the treatment strategy. In administering the particular doses, one would preferably provide a pharmaceutically acceptable composition (according to FDA standards of sterility, pyrogenicity, purity and general safety) to the patient systemically. Intravenous injection is generally preferred. Continuous infusion over a time period of about 1 or 2 hours or so is also contemplated.

Whether used for treating angiogenic diseases, such as arthritis, psoriasis, atherosclerosis, diabetic retinopathy, age-related macular degeneration, Grave's disease, vascular restenosis, hemangioma and neovascular glaucoma (or other diseases described above), or solid tumors, the present invention can be combined with other therapies.

The αvβ3 integrin/VEGFR2 complex inhibition based treatment methods of the present invention may be combined with any other methods generally employed in the treatment of the particular tumor, disease or disorder that the patient exhibits. So long as a particular therapeutic approach is not known to be detrimental to the patient's condition in itself, and does not significantly counteract the polypeptides comprising αvβ3 integrin/VEGFR2 complex inhibiting based treatment, its combination with the present invention is contemplated.

In accordance with another aspect of the invention, methods of, and uses in, significantly inhibiting αvβ3 integrin and VEGFR2 complex formation without inhibiting natural ligand binding to αvβ3 integrin are provided. These methods comprise contacting, in the presence of VEGF, a population of cells or tissues that includes a population of endothelial cells that express VEGFR2 (KDR/Flk-1) and αvβ3 integrin with a composition comprising a biologically effective amount of at least one peptide that inhibits complexing of αvβ3 integrin and/or VEGFR2.

Proliferation inhibition methods and uses are provided, including those to specifically inhibit VEGF-induced endothelial cell proliferation and/or migration, which generally comprise contacting a population of cells or tissues that includes a population of endothelial cells and VEGF with a composition comprising a biologically effective amount of the at least one αvβ3 integrin/VEGFR2 complex inhibiting peptide under conditions effective to inhibit VEGF-induced endothelial cell proliferation and/or migration.

The foregoing methods and uses can be performed in vitro and in vivo. In the latter case the tissues or cells are located within an animal and the at least one αvβ3 integrin/VEGFR2 complex inhibiting agent is administered to the animal. In both cases, the methods and uses become methods and uses for inhibiting angiogenesis, comprising contacting a tissue comprising, or a population of, potentially angiogenic blood vessels, i.e., those potentially exposed to VEGF, with an anti-angiogenic composition comprising a biologically effective amount of the at least αvβ3 integrin/VEGFR2 complex inhibiting peptides under conditions effective to inhibit angiogenesis.

Where populations of potentially angiogenic blood vessels are maintained ex vivo, the present invention has utility in drug discovery programs. In vitro screening assays, with reliable positive and negative controls, are useful as a first step in the development of drugs to inhibit or promote angiogenesis, as well as in the delineation of further information on the angiogenic process. Where the population of potentially angiogenic blood vessels is located within an animal or patient, the anti-angiogenic composition is administered to the animal as a form of therapy.

"Biologically effective amounts", in terms of each of the foregoing inhibitory methods are therefore amounts of the at least one αvβ3 integrin/VEGFR2 complex inhibiting peptide effective to inhibit αvβ3 integrin and VEGFR2 complex formation without substantially inhibiting natural or native ligand binding to αvβ3 integrin.

The present invention thus further provides methods of, and uses in, treating a disease associated with angiogenesis, including all forms of cancer associated with angiogenesis, comprising administering to an animal or patient with such a disease or cancer a therapeutically effective amount of at least a first pharmaceutical composition that comprises at least αvβ3 integrin/VEGFR2 complex inhibiting peptide.

The foregoing anti-angiogenic treatment methods and uses will generally involve the administration of the pharmaceutically effective composition to the animal or patient systemically, such as by transdermal, intramuscular, intravenous injection and the like. However, any route of administration that allows the therapeutic agent to localize to the angiogenic site or sites, including tumor or intratumoral vascular endothelial cells, will be acceptable. Therefore, other suitable routes of delivery include oral, rectal, nasal, topical, and vaginal. U.S. Pat. No. 5,712,291, is specifically incorporated herein by reference for purposes including further describing the various routes of administration that may be included in connection with the treatment of an angiogenic disease or disorder. For conditions associated with the eye, ophthalmic formulations and administration are contemplated.

"Administration", as used herein, means provision or delivery of the αvβ3 integrin/VEGFR2 complex inhibiting agent in an amount(s) and for a period of time(s) effective to exert anti-angiogenic and/or anti-tumor effects. The passive administration of proteinaceous therapeutics is generally preferred, in part, for its simplicity and reproducibility.

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

EXAMPLES

Example 1

Integrin Phosphorylation and Signaling is Critical for VEGF-Induced Cellular Responses and Pathological Angiogenesis In Vivo We sought to directly establish the role of $\beta_3$ integrin tyrosine phosphorylation and integrin signaling in VEGF-stimulated responses of EC as well as in pathological angiogenesis in vivo. To this end, we knocked in a mutant form of $\beta_3$ integrin, in which both tyrosines 747 and 759 were substituted for phenylalanines ((DiYF $\beta_3$ integrin), instead of wild type in mice. In this study we combined in vivo and ex vivo angiogenesis assays with an extensive characterization of EC derived from both WT and DiYF mice in order to perform a complete analysis of the role of integrin $\beta_3$ and its signaling in functional responses to VEGF.

Results

Tyrosine Phosphorylation of $\beta_3$ Cytoplasmic Motif in EC Occurs Upon Adhesion to Integrin Ligands Previous studies using model cell lines and platelets demonstrated that $\beta_3$ integrin cytoplasmic tyrosine phosphorylation is involved in outside-in integrin signaling. Therefore, we assessed whether EC adhesion to extracellular matrix proteins is able to induce beta 3 tyrosine phosphorylation. Accordingly, we isolated EC's from the lungs of wild type (WT) and DiYF mice, plated them on various substrates and assessed the phosphorylation of beta 3 on Tyr747 and Tyr459 (FIG. 1A). Very low levels of 747 as well as 759 $\beta_3$ phosphorylation were observed in cells kept in suspension or plated on the poly-lysine as a control substrate. Extracellular matrix proteins which serve as ligands for $\alpha_v\beta_3$ such as vitronectin, fibronectin, fibrinogen and gelatin strongly stimulated Tyr759 and Tyr747 phosphorylation. At the same time, laminin and collagen, which are recognized primarily not by integrins other than $\alpha_v\beta_3$ induced lower levels of tyrosine phosphorylation. Sodium pervanadate known to block phosphatase activity was used as a positive control in this experiment. As anticipated, no tyrosine phosphorylation of $\beta_3$ integrin was observed in DiYF EC under any conditions.

VEGF Treatment of EC Induces Tyrosine Phosphorylation of Beta 3

The role of $\beta_3$ subunit phosphorylation in extracellular matrix recognition was previously assessed in model cell lines, such as CHO cells and K562 cells. This system does not provide any insight on the most important functions of the $\beta_3$ integrin, namely its role in angiogenesis and in the regulation of VEGF or FGF-induced EC responses. These processes can be only assessed in EC expressing appropriate receptors and signaling intermediates. Thus, we determined whether VEGF treatment is able to affect the phosphorylation status of $\beta_3$. Treatment of EC in suspension with VEGF-A165 induced Tyr747 as well as Tyr 759 phosphorylation of $\beta_3$ in a time-dependent manner. Both time curves of $\beta_3$ tyrosine phosphorylation followed a bell-shaped pattern, which is typical for growth factor-induced responses. Thus, not only integrin engagement but also VEGF treatment in suspension stimulated tyrosine phosphorylation of $\beta_3$ subunit in EC, suggesting a possible regulatory role of this process in VEGF-induced angiogenesis.

Angiogenesis In Vivo is Impaired in DiYF Mice

Thus, we determined whether $\beta_3$ integrin phosphorylation is crucial for a complete angiogenic response to VEGF in vivo. Accordingly, we implanted Matrigel containing VEGF-A subcutaneously into WT and DiYF mice and assessed angiogenic response based on the amount of hemoglobin extracted from Matrigel. As shown in FIG. 2A, hemoglobin concentration was at least 5 fold lower in Matrigel plugs isolated from DiYF mice compared to WT counterparts. The vascular density in Matrigel implants assessed by vWF staining was 4.2 fold lower in DiYF mice than in WT controls (p=0.01) (FIG. 2B). In Matrigel plugs from WT mice, large vWF-positive blood vessels were observed (FIG. 2C). In contrast, only 50% of Matrigel plugs from DiYF mice exhibited any staining for vWF and had a distinguishable vasculature (FIG. 2C). Thus, VEGF-induced angiogenesis was significantly impaired in DiYF mice.

Next, we assessed tumor-induced pathological angiogenesis in DiYF and WT mice. To this end, mouse melanoma cells were implanted subcutaneously into mice and 10 day after, tumors were excised. The vascular density in tumors grown in DiYF mice was 6 fold lower than that in WT mice (p=0.009) (FIG. 3A). Tissue section analysis revealed the presence of well-developed blood vessels, which were positively stained for vWF, CD31 and laminin (basement membrane component) in tumors from WT mice. In contrast, in tumors formed in DiYF mice, blood vessels were sparse and thin-walled based on laminin staining (FIG. 3B). As a result of defective vascularization, the average weight of tumors formed in DiYF mice was at least 2 fold lower compared to WT (0.14 g vs 0.29 g) (FIGS. 3C and D). Thus, $\beta_3$ integrin phosphorylation plays a crucial role in the regulation of pathological angiogenesis in vivo.

DiYF Mutations within the $\beta_3$ Integrin Cytoplasmic Domain Impair Angiogenic Properties of EC Previous studies demonstrated that $\alpha_v\beta_3$ integrin controls cell growth rate, migration, invasive potential and angiogenic phenotype of EC. Therefore, we assessed whether impaired $\beta_3$ integrin tyrosine phosphorylation affects an ability of EC to form capillaries and tubes ex vivo. WT but not DiYF EC was able to form well-assembled and complete capillary cord-like structures in the presence of VEGF-A (FIG. 3A). In contrast, DiYF EC remained randomly scattered without any sings of organization (FIG. 4A). From FIG. 4B it is evident that the number of cords formed by WT EC was 5.4 fold higher compared to DiYF cells.

It is known that the major phenotypic characteristic of EC is its ability to assemble into the interconnected network of tube-like structures when grown in three-dimensional matrix. WT but not DiYF EC formed clearly defined and well connected network of EC tubes (FIG. 4C). These structures were relatively stable and remained well-organized for at least 18 hours. As evident from FIG. 4C, DiYF EC were not able to complete the tube formation and no obvious pattern was formed even in the presence of VEGF. An extend of tube formation was quantified by measuring the length of tubes and mean values of three independent experiments are represented in FIG. 3 D. VEGF treatment induced about 3 fold increase in the length of the tubes formed by WT EC but had a little effect on DiYF EC.

Tyrosine Phosphorylation of $\beta_3$ Integrin Controls Ex Vivo Angiogenesis in Response to VEGF We next assessed whether DiYF mutations affected an outgrowth of vascular sprouts from aortic segments isolated from mice. First, ex vivo angiogenic assay was performed in Matrigel enriched with growth factors. It was evident that aortic rings from WT mice produced extensive network of vascular sprouts while DiYF aortic rings failed to do so (FIG. 4E). To elucidate the role of $\beta_3$ integrin in VEGF induced responses, aortic ring assay was performed in the presence or absence of VEGF using growth factor reduced Matrigel. Aortic rings from WT mice produced significantly higher number of vascular sprouts both in absence and presence of VEGF (FIG. 4F). The quantification of aortic ring sprouts revealed the ability of DiYF cells to form vascular sprouts ex vivo was at least 4 fold lower regardless of stimulation (FIG. 4G). VEGF produced a mild increase in capillary formation of DiYF rings, however, the number of sprouts was only 20-25% of that in WT aortic rings (FIG. 4G). To further analyze the capillary growth from aortic rings a detailed kinetic study was undertaken. The time curves of vascular growth are presented in FIG. 4H. In the absence of stimulation, a very few microvessels were detected in both WT and DiYF implants even after a prolonged incubation; where as serum-induced neovascularization was considerably higher in WT implants as compared to DiYF (FIG. 4H). The peak values of capillary growth were observed 8 days after implantation and were 10 and 45 microvessels per ring for DiYF and WT, respectively. VEGF served as a strongest stimulus and produced extensive formation of capillaries in WT but not in DiYF aortic rings (FIG. 4H). Taken together, these results indicate that the impaired pathological angiogenesis in DiYF mice was due to the defective functional responses of endothelial cells.

$\beta_3$ Integrin Cytoplasmic Domain Phosphorylation Regulates EC Adhesion, Spreading and Migration Next, in order to further define the nature of the angiogenic defect observed in DiYF mice, we compared angiogenesis-relevant functions of EC isolated from WT and DiYF mice. We first assessed whether the mutation in $\beta_3$ integrin cytoplasmic domain had any effect on EC adhesion and subsequent cell spreading on extracellular matrix substrates. To this end, WT and DiYF EC were plated on various integrin ligands and numbers of attached and spread cells per field were counted. WT and DiYF EC adhered and spread equally well on fibronectin, laminin-1 and collagen coated plates (FIGS. 5A and B). In contrast, a significant difference in the behavior of WT and DiYF EC was found using $\alpha_v\beta_3$ ligand, vitronectin. On this substrate, DiYF EC showed a 2 fold reduction in adhesion and a 4 fold decrease in the number of spread cells (FIGS. 5A and B). Next, we compared migration of WT and DiYF EC towards various extracellular matrix proteins known to be recognized by integrins. Similar to the results of adhesion assays, WT and DiYF EC migrated equally well towards fibronectin, laminin and collagen but not towards vitronectin, where a 3 fold reduction in migration of DiYF EC versus WT was observed (FIG. 5C).

Then, we compared a VEGF-induced migratory activity of WT and DiYF EC.

Stimulation of WT EC with VEGF at 5, 10 and 20 ng/ml induced 1.5, 2.5 and 2.9 fold increases of migration compared to untreated EC (FIG. 5D). DiYF EC also responded to VEGF stimulation, however, the rate of migration was substantially reduced (FIG. 5D). Thus, tyrosine phosphorylation of $\alpha_v\beta_3$ integrin appears to play an important role in VEGF-induced EC migration to extracellular matrix. To further confirm these results, we utilized an alternative and more physiologically relevant method to assess EC migration. WT and DiYF EC were plated on various integrin ligands and were allowed to form a confluent monolayer. Then, a wound in the monolayer was created and the healing process was monitored at different time points. The quantitative aspects of wound recovery and representative images of EC are presented in FIGS. 5E and 5F, respectively. Where as WT and DiYF EC migrated equally well on fibronectin, laminin and collagen, a 3 fold reduction in migration on vitronectin was observed in DiYF EC compared to WT (FIG. 5E). Moreover, using live video microscopy, the process of EC migration and wound recovery was carefully monitored in order to characterize differences in cell movement between WT and DiYF EC. Thus, it appears that DiYF mutation impairs $\alpha_v\beta_3$ integrin-dependent and VEGF-stimulated responses of EC indicating its potential role in the regulation of a cross-talk between $\alpha_v\beta_3$ and VEGF receptor(s).

$\beta_3$ Integrin Phosphorylation is Required for Sustained Activation of VEGF Receptor-2

Next, we sought to identify a molecular mechanism responsible for abnormalities observed in DiYF EC. Previous studies using $\beta_3$ null mice demonstrated that the absence of $\beta_3$ leads to upregulation of VEGFR-2 and consequently to augmentation of angiogenic responses of EC. However, no differences in VEGFR-2 levels were observed between DiYF and WT EC of lung as well as of aortic origin (not shown). It was previously shown that integrin $\beta_3$ is able to form a complex with VEGFR-2 immediately upon stimulation with VEGF, and this association was proposed to be necessary for the activation of angiogenic program in EC. Therefore, we sought to determine whether DiYF mutations impaired an ability of $\beta_3$ integrin to interact with VEGFR-2. Low levels of $\beta_3$-VEGFR2 interactions were observed in nonstimulated WT EC in suspension or upon adhesion to extracellular matrix. VEGF stimulated a dramatic increase in a complex formation between $\beta_3$ and VEGFR-2 in WT EC plated on vitronectin, but not in suspension or on laminin, demonstrating a ligand specificity of this phenomenon. In contrast, no interaction between $\beta_3$ and VEGFR2 was observed in DiYF EC under any conditions. Thus, it appears that $\beta_3$ tyrosine phosphorylation is essential for an interaction between VEGFR-2 and $\alpha_v\beta_3$ integrin. In order to further investigate the mechanism of $\beta_3$ integrin-dependent VEGF signaling, we performed a detailed comparison of VEGFR-2 phosphorylation status in response to VEGF in WT and DiYF EC. A time course of VEGFR2 phosphorylation is presented in FIG. 6C. In WT EC, VEGF induced a bell-shaped response with a maximum 6 fold increase in VEGFR-2 phosphorylation over control. After 45 min, VEGFR-2 phosphorylation returned to the control levels. In contrast, VEGF exerted much lower increase in VEGFR-2 phosphorylation in DiYF EC with the maximum value of 2.5 fold over control. Importantly, VEGFR-2 in WT EC remained phosphorylated 3 times longer than in DiYF EC (FIG. 6C). Thus, the lack of integrin phosphorylation in DiYF EC resulted in reduced phosphorylation/activation of VEGFR-2 in response to VEGF, which, in turn, affected all the signaling events downstream of VEGFR-2.

TyRosine Phosphorylation is Critical for VEGF-Induced $\alpha_v\beta_3$ Integrin Activation An intrinsic property of integrins is an increased soluble ligand binding in response to stimulation, a process referred to as integrin activation. We and others previously reported that VEGF via VEGFR-2 is able to activate $\alpha_v\beta_3$ integrin on EC. Accordingly, we sought to determine whether impaired activation of VEGFR-2 in DiYF EC results in defective $\alpha_v\beta_3$ activation by VEGF. VEGF induced at least 6 fold increase of fibrinogen binding to WT EC and only 3 fold increase of binding to DiYF EC (FIG. 6D). MnCl$_2$, an agonist known to activate integrins and at the same time to stimulate $\beta_3$ integrin tyrosine phosphorylation, produced at least 40 fold increase in fibrinogen binding to WT EC, compared to 17 fold increase observed in DiYF EC (FIG. 6E). The specificity of ligand binding was conformed by addition of 10 fold excess of unlabelled fibrinogen. Similar results were observed when integrin activation was monitored using a monovalent activation-dependent ligand WOW-1 Fab. VEGF and MnCl$_2$ stimulated 9 and 30 fold increases, respectively, in WOW-1 binding to WT EC and 3.5 and 14 fold increases, respectively, to DiYF EC (FIGS. 6F and 6G). Thus, it is apparent that DiYF mutations within the cytoplasmic domain of $\beta_3$ integrin significantly impair the process of integrin activation, which, in turn, results in defective cell adhesion and migration.

Materials and Methods

Animals

DiYF mice were generated in the laboratory of Dr. David R. Phillips and maintained on C57/B16 background (7 generations of backcrossing). Six to eight week old wild-type (WT) and DiYF mice were used in study.

Primary Lung Endothelial Cell Isolation

Wild type and DiYF mouse lungs were excised, minced and digested using collagenase-dispase reagent (3 mg/ml). Digests were strained and the resulting cell suspension was plated on flasks coated with 1 mg/ml fibronectin. Endothelial cells were isolated and characterized.

Aortic Ring Assay

Thoracic aortas from WT and DiYF mice were removed under aseptic conditions and spliced into 1 mm thick rings. Thoracic aortic rings were placed between two layers of growth factor depleted Matrigel and allowed to solidify at room temperature. Matrigels were overlaid with either with DMEM or endothelial growth medium with or without VEGF (40 ng/ml). Microvessel outgrowth was visualized by phase contrast microscopy and numbers of vessels growing from each aortic ring were counted and photographed every two days using Leica phase contrast microscope.

Cell Adhesion and Cell Spreading Assay

Mouse lung endothelial cells were detached from the tissue culture flasks using 20 mM EDTA. Cells were washed twice with sterile PBS and re-suspended in DMEM. The cell suspensions were added to ligand-coated wells and placed in humidified incubator for 45 min. The wells were gently washed three times with DMEM and photographs were taken. The numbers of attached and spread cells per field were counted.

Cell Migration Assay

Transwell tissue culture inserts were coated with various integrin ligands for 24 h at 4° C. Both WT and DiYF lung endothelial cells were trypsinized and $1\times10^5$ cells were added into each well. The lower chamber contained varying concentrations of VEGF-A165 (0-20 ng/ml). Cells were allowed to migrate for 12 h and fixed with 3.7% formaldehyde/PBS for 15 min and stained with 0.5% crystal violet. The non-migrated cells adhered to the top surface were removed and three random 10× fields were photographed using Leica inverted phase contrast microscope.

Endothelial Wound Healing Assay

WT and DiYF mouse lung endothelial cells were grown to confluence in 12 well plates precoated with various integrin ligands. Cells were serum starved for 4 h and then a wound was created by a 1000 µl pipette tip. Wells were rinsed twice with sterile PBS to remove wound-derived loose and dislodged cells and further cultured DMEM medium containing 2% FBS. Images were recorded immediately after wounding (time zero) and 12 h later. Cell migration was quantified using image analysis of 5 randomly selected fields of denuded area. The mean wound area is expressed as percent of recovery (% R) from three identically treated plates using the equation % R=$[1-(T_f/T_0)]\times100$, where: $T_0$ is the wounded area at 0 h and $T_f$ is the wounded area after 12 h.

Fibrinogen Binding Assay

To assess fibrinogen binding, semiconfluent wild type and DiYF mouse lung endothelial cells were serum starved for 4 h and further induced with 20 ng/ml VEGF-165, 20 ng/ml b-FGF or 1 mm MnC12. Fluorescein isothiocyanate (FITC)-labeled fibrinogen was added at a final concentration of 200 nM for 45 min. Cells were fixed with 3.7% formaldehyde/PBS for 15 min and washed twice with ice-cold 1×PBS. Fluorescence-activated cell sorting (FACS) was performed using a FACS Calibur (Becton Dickinson, San Jose, Calif.) and data were analyzed using CellQuest software program.

WOW-1 Binding Assay

Wild type and DiYF mouse lung endothelial cells were serum starved for 4 h and further stimulated with 20 ng/ml VEGF-165, 20 ng/ml b-FGF or 1 mm MnC12 separately. WoW-1 Fab was added at a final concentration of 30 mg/ml, followed by addition of Fluorescein isothiocyanate (FITC) conjugated goat anti-mouse IgG at 10 µg/ml. After 30 min cells were fixed with 3.7% formaldehyde/PBS for 15 min, washed twice with 1×PBS and FACS was performed using a FACS Calibur (Becton Dickinson, San Jose, Calif.) instrument and data were analyzed using CellQuest software program.

Precapillary Cord Formation Assay

Wild type and DiYF mouse lung endothelial cells were trypsinized and washed twice with DMEM containing 10% FCS. These cells were seeded on Matrigel coated 6 well plate and cells were allowed to adhere. After 24 h, the medium was removed and cells were overlaid with 0.5 ml of Matrigel containing 40 ng/ml VEGF. All the wells were filled with 2 ml of endothelial growth medium and cells were observed and photographed every day using Leica phase contrast microscope.

Tube Formation Assay

The formation of vascular tube-like structures by wild type and DiYF mouse lung endothelial cells were assessed on the basement membrane matrix preparation. Six well plates were coated with 0.5 ml of Matrigel according to the manufacturer's instructions. Wild type and DiYF mouse lung endothelial cells were detached from the tissue culture flasks using 20 mM EDTA. Cells were washed twice with sterile 1×PBS and seeded on Matrigel coated plate. Medium was supplemented with or without 20 ng/ml VEGF and further incubated at 37° C. for 8 h. The tube formation was observed using an inverted phase contrast microscope (Leica) and photographs were taken from each well. Using ImagePro software, the degree of tube formation was quantified by measuring the length of tubes in random fields.

Immunoprecipitation and Western Blot Analysis

Semiconfluent 1, endothelial cells grown on various integrin substrates were made quiescent by 4 h starvation in serum free DMEM medium. Cells were lysed in a 50 mM Tris-HCl buffer pH 7.4,containing 150 mM NaCl, 1% Triton X-100, and protease and phosphatase inhibitors. Cell lysates were cleared by centrifugation (10000 gx for 10 mins) and further incubated with rabbit polyclonal anti-b3 integrin antibody for 3 h at 4° C. and immune complexes were recovered using protein A-agarose. Immunoprecipitates were washed two times with lysis buffer, twice with high salt buffer and twice with no salt buffer. Integrin immune complexes from agarose beads samples were boiled for 5 min in SDS-PAGE sample buffer. Immunocomplexes were resolved by SDS-PAGE (6%), and transferred to nitrocellulose membrane. These blots were probed with anti-VEGFR-2 and anti-b3 integrin antibody respectively. Proteins were detected using enhanced chemiluminescence technique (Amersham).

To analyse the $\beta_3$ integrin tyrosine phosphorylation wild type and DiYF mouse lung microvascular endothelial cells suspended in various integrin ligand coated plates and further incubated at 37° C. for 60 mins. Cells were lysed and cell lysates containing equal amount of protein were subjected to Western blot analysis using rabbit anti-integrin $\beta_3$ [pY$^{747}$] and [pY$^{759}$] antibody. Cell lysates were also analyzed for $\beta_3$ integrin expression as a loading control.

Serum starved wild type and DiYF endothelial cells were also treated with 20 ng/ml VEGF for 0-60 mins. Cell lysates were analyzed by Western blot using anti-integrin $\beta_3$ [pY$^{747}$], anti-integrin [pY$^{759}$], anti-p-VEGFR-2, anti-VEGFR-2, anti-p-ERK1/2, anti-ERK1/2, anti-p-Akt, anti-Akt, anti-p-P38MAPK and anti-MAPK antibody. The wild type and DiYF endothelial cells were lysed and equal proteins from total cell lysates were subjected SDS-PAGS and analyzed by western blot using anti-VEGFR-2 and anti-CD-31 antibody.

Statistical Analysis

Values were expressed as mean plus or minus standard deviations (SD). P values were based on the paired t test. All the experiments were repeated at least 3 or more times unless indicated otherwise. Results were considered statically significant with P value less than 0.05.

Example 2

Integrin Affinity Modulation in Angiogenesis

The aim of this study was to assess the role of each individual subfamily of integrin receptors in VEGF-induced angiogenic cellular responses using a siRNA-based short-term knockdown approach in primary endothelial cells.

Experimental

Materials

Rabbit polyclonal anti-VEGFR-2, anti-β3-integrin, anti-β5-integrin, antiβ1-integrin, mouse monoclonal anti-phospho tyrosine (PY20 and PY99) antibodies, and β1, β3, β5 integrin-specific siRNAs were purchased from Santa Cruz Biotechnology, Inc. (Santa Cruz, Calif.). Anti-VEGFR-2 and anti-phospho VEGFR-2 were from Cell Signaling Technology (Beverly, Mass.). Mouse monoclonal anti-β3-integrin blocking antibody was from Chemicon International Inc. (Temecula, Calif.). Anti-CD31 antibody was obtained from DAKO (Kyoto, Japan). Mouse monoclonal anti-β3-integrin activating antibodies were generated in our laboratory. Purified collagen, laminin, vitronectin, and VEGF were purchased from R&D Systems (Minneapolis, Minn.). Matrigel was obtained from BD Biosciences (San Jose, Calif.). The HUVEC nucleofector kit was obtained from Amaxa Biosystems (Gaithersburg, Md.). Alexa 488 conjugated goat anti-rabbit, goat anti-mouse IgG, and TRITC-conjugated goat anti-rabbit IgG were from Invitrogen (Carlsbad, Calif.). Purified WOW-1 Fab was provided by Dr. S. J. Shattil, The Scripps Research Institute, La Jolla, Calif. All other chemicals were analytical grade.

Cell Culture and Transfection

Human umbilical cord vein endothelial cells (HUVEC) cells were grown in Dulbecco's modified Eagle's medium (DMEM) supplemented with supplemented with 10% FBS, 90 µg/mL heparin sulphate, 90 µg/mL endothelial cell growth factor, 100 U/mL penicillin, 100 µg/mL streptomycin. Cells were used for the experiment between second and fifth passages. HUVECs were transiently transfected using the HUVEC nucleofector kit according to the manufacturer's instructions. Forty-eight hr after transfection, cells were serum starved and used for experiments. Cell surface expressions of integrins were detected as described previously.

Cell Adhesion Assay

HUVECs were detached from the tissue culture flasks using 20 mM EDTA. Cells were washed twice with sterile phosphate buffered saline (PBS) and re-suspended in serum-free DMEN. The cell suspensions were added to integrin ligand-coated wells and placed in a humidified incubator for 45 min. The wells were gently washed three times with DMEM and photographs were taken. The numbers of attached and spread cells per field were counted.

Endothelial Wound Healing Assay

HUVECs were grown to confluence in 12 well plates precoated with various integrin ligands. Cells were serum starved for 4 h and then a wound was created by a pipette tip. Wells were rinsed twice with sterile PBS to remove wound-derived loose and dislodged cells and further cultured in DMEM medium containing 2% FBS. Images were recorded immediately after wounding (time zero) and 12 h later. Cell migration was quantified using image analysis of five randomly selected fields of denuded area. The mean wound area is expressed as percent of recovery (% R) from three identically treated plates using the equation % R=[1−(T$_t$/T0)]×100, where T0 is the wounded area at 0 h and Tt is the wounded area after 12 h.

WOW-1 Binding Assay

Semiconfluent HUVECs were serum starved for 4 h and further stimulated with 20 ng/mL VEGF-A165 or VEGFDΔNΔC. WOW-1 Fab was added to a final concentration of 30 µg/mL, followed by addition of FITC-conjugated goat anti-mouse IgG at 10 µg/mL. After 30 min cells were fixed with 3.7% formaldehyde in PBS for 15 min, washed twice with PBS, and fluorescence-activated cell sorting (FACS) was performed using a FACS Calibur (Becton Dickinson, San Jose, Calif.) and data were analyzed using CellQuest software.

Tube Formation Assay

The formation of vascular tube-like structures by HUVECs was assessed on a basement membrane matrix preparation. Twelve-well plates were coated with 0.5 mL of Matrigel according to the manufacturer's instructions. HUVECs transfected with various β integrin-specific siRNAs. Cells were detached from tissue culture flasks using 20 mM EDTA in PBS. Cells were washed twice with sterile PBS and seeded on Matrigel-coated plates. Medium with or without 20 ng/mL VEGF was added and cells were further incubated at 37° C. for 8 h. The tube formation was observed using an inverted phase contrast microscope (Leica, Wetzlar, Germany) and photographs were taken. Using ImagePro software (Media Cybernetics, Silver Spring, Md.), the degree of tube formation was quantified by measuring the length of tubes in three random fields.

Immunohistochemistry and Immunocytochemistry Analysis

To study integrin activation status, HUVECs were grown in monolayer on glass slides and then treated with 1 mM $MnCl_2$ or 20 ng/mL VEGF for 10 min. These cells were further incubated with WOW-1 antibody for additional 30 min. These cells were fixed with paraformaldehyde for 10 min, blocked with 5% bovine serum albumin for 30 min, and incubated with FITC-conjugated anti-mouse IgG. These cells were washed, mounted with coverslips, and analyzed under a florescent microscope (Leica). Alternatively, cells were further incubated with anti-VEGFR-2 antibody and incubated with TRITC-conjugated anti-rabbit IgG. These cells were washed, mounted, and analyzed under confocal microscopy (Leica).

Western Blot Analysis

HUVECs were lysed following the experiment using lysis buffer (50 mM Tris-HCl (pH 7.4), 150 mM NaCl, 1% Nonidet P-40, 1% Triton X-100, 1% sodium deoxycholate, 0.1% SDS, 5 mM iodoacetamide, 2 mM phenylmethylsulfonyl fluoride, 2 mM EDTA, 10 mM NaF, 10 mM Na2P2O7, 10 µg/mL leupeptin, 4 µg/mL pepstatin, and 0.1 units/mL aprotinin). Cell lysates were centrifuged at 13,000×g for 10 min at 4° C. Supernatants were collected and assayed for protein concentration using the Bio-Rad protein assay method (Hercules, Calif.). Cell lysates were denatured using Laemmli sample buffer and proteins were separated by sodium dodecyl sulphate polyacrylamide gel electrophoresis and probed with indicated antibody. When appropriate, nitrocellulose membranes were stripped and blotted according to manufacturer's instructions.

Results

Silencing Effects of siRNA on Expression of Integrins in Endothelial Cells

We utilized small interfering RNAs (siRNAs) to down regulate expression of β subunits of various integrin heterodimers in primary EC. Upon transfection of EC with specific siRNAs, significant down-regulation of β1, β3, and β5 subunit expressions was achieved as evidenced by results of Western blotting analysis (FIGS. 7A, B, and C). Quantitative analysis revealed that the expression of β1, β3 and β5 integrins was down-regulated by 75, 70, and 80%, respectively, whereas the control siRNA did not show any effect on expression of any of the integrins tested (FIG. 7A, B, C). Cell surface expression of β1, β3, and β5 integrins following siRNA transfection were conformed by FACS analysis. Results revealed that transfection of HUVECs with specific siRNAs resulted in 74, 65, and 76% decreases in surface expression of β1, β3, and β5 integrins, respectively (FIG. 7D, E, F). Each siRNA was specific for its respective β subunit, since siRNAs did not affect expression levels of other subunits (not shown). These results conclusively indicated that siRNAs down-regulated the total expression, as well as cell surface levels, of specific β integrins in endothelial cells.

Cell Adhesion Profiling of EC Lacking β1, β3, and β5 Integrin Subunits

Adhesion of endothelial cells to extracellular matrix (ECM) components through cell surface integrins are known to required for endothelial cell growth, differentiation, and survival. Endothelial cell adhesion to ECM induces cellular proliferation and programmed cell death of non-adherent cells in suspension. Integrin ligand ligation induces a wide variety of intracellular signaling, including tyrosine phosphorylation of FAK, increased inositol lipid synthesis, cyclin synthesis, and expression of several cell survival factors. Endothelial cell surface integrins mediate adhesion to ECM proteins, including vitronectin, laminin, collagen, von Willebrand factor, and fibrinogen. To examine endothelial cell adhesion to various ECM proteins following inhibition of expression of specific integrin subunits, HUVECs transfected with integrin-specific siRNA were plated on various integrin ligand coated plates and ability of EC to adhere to the distinct extracellular matrix components were tested. Representative images and quantitative results are shown in FIGS. 8A and 8B, respectively. Inhibition of expression of the β1 subunit abolished EC adhesion to both collagen and laminin, but not to vitronectin. Silencing of the β3 subunit completely inhibited EC adhesion to vitronectin, but not to collagen or laminin. Inhibition of expression of the β5 subunit only partially (~50%) inhibited cell attachment to vitronectin and had no substantial effect on adhesion to other tested extracellular matrix components. These observations indicated that sister integrins did not functionally compensate after expression of a specific integrin was silenced in HUVECs.

Vitronectin (αvβ3) and Collagen (α5β1) Receptors Modulate Endothelial Cell Migration Extracellular matrix provides critical support for proliferating vascular endothelium through adhesive interaction with endothelial cell surface integrins. Extracellular matrix also provides the scaffold essential for maintaining the organization of vascular endothelial cells in to blood vessels. Endothelial cell adhesion to extracellular matrix is required for endothelial cell proliferation, migration, and morphogenesis. Integrin-mediated migration of endothelial cells also plays a crucial role in vascular remodeling involved in angiogenesis, embryonic vasculogenesis, and re-endothelialization in arteries following angioplasty. To examine which of the endothelial integrins trigger endothelial cell migration, HUVECs were transfected with various β-integrin specific siRNAs and these cells were plated on various extracellular matrix components. A wound was created across the cell monolayer by scraping away a swath of cells and the extent of wound healing due to the transfected EC was measured after 12 hours. Representative images are shown in FIG. 9A. Percentages of wound recovery were quantified (FIG. 9B). Control EC were able to completely close the wound on vitronectin and was assigned value of 100%. EC plated on collagen and laminin shown 85% and 30% recovery respectively. EC transfected with siRNA targeting the β1 subunit were almost completely unable to heal wounds on collagen, but were not substantially different from control EC on vitronectin and laminin. Silencing of β3 and β5 subunits diminished wound recovery on vitronectin by 50 and 30%, respectively, without any effect on collagen and laminin. The results of these assays demonstrate that the critical integrin subunits for regulation of endothelial cell communication with extracellular matrix are β3 and β1. As above, no compensatory effects were observed.

αvβ3 Integrin is Crucial for Endothelial Cell Morphogenesis

During angiogenesis, proliferating and migrating endothelial cells organize to form three-dimensional capillary networks. This processes initiates with transition of endothelial cells into spindle-shaped morphology. This is followed by endothelium alignment and connection into solid, multicellular, precapillary cord-like structures that form an integrated polygonal network. During this vascular morphogenesis, extracellular matrix serves as an adhesive support and, through interaction with integrins, provides crucial signaling to regulate endothelial cell shape and contractility. To examine which integrin is crucial during endothelial cell morphogenesis, HUVECs were transfected with various β-integrin specific siRNAs and angiogenic properties of EC were assessed using a capillary tube formation assay on Matrigel. Capillary tube forming ability of unstimulated as well as VEGF-stimulated cells was tested. Silencing of the β1 subunit affected capillary formation in the absence as well as in the presence of VEGF. As shown in FIG. 10A, the regularity of the typical honeycomb-like pattern was disturbed resulting in incomplete connections between cellular cords. Among three different siRNA transfections, knockdown of the β3 subunit produced the most severe inhibitory effect on capillary growth; silencing of β3 completely abolished the formation of cellular cords by these EC both in the absence and presence of VEGF (FIG. 10A). Down regulation of β5 integrin subunit substantially, but not completely, impaired capillary growth of unstimulated EC and, to a lesser extent, of VEGF-stimulated cells. Quantitative aspects of capillary growth of all three EC lines are shown in FIG. 10B. Thus, it appears that knockdown of β3 subunit was the most effective in inhibiting angiogenic response in vitro. Therefore, we further focused on β3 integrin, which forms a complex exclusively with αV subunit on EC to produce $\alpha_v\beta_3$ heterodimer.

$\alpha_v\beta_3$ Integrin Affinity Modulation and Association with VEGFR-2

Integrin affinity relates to conformational modification in the integrin heterodimer to strength of ligand binding. Usually non-integrin receptors cause alterations in the integrin cytoplasmic domain ultimately modulating integrin activation state. Several receptor tyrosine kinases (RTKs), G-protein coupled receptors, and cytokines have been shown to modulate integrin activation state. To study the synergism between $\alpha_v\beta_3$ integrin and RTKs such as VEGFR-2 on endothelial cell surface, HUVECs were induced with VEGF and integrin affinity was estimated. A genetically engineered antibody WOW-1 was used as a probe to detect $\alpha_v\beta_3$ in the high affinity state on the surface of EC in the monolayer. WOW-1 Fab is a monomeric soluble ligand which binds only to the activated form of $\alpha_v\beta_3$. Stimulation with VEGF-A165 increased WOW-1 binding to EC by 6-fold compared to resting cells as measured by FACS analysis (FIG. 11A). Importantly, the mature form of VEGF-D, VEGF-DΔNΔC, known to be specific for VEGFR-2 on EC of blood vessel origin, was also potent inducer of WOW-1 Fab binding, indicating that VEGFR-2 but not VEGFR-1 is primarily receptor mediating $\alpha_v\beta_3$ integrin activation.

The results of WOW-1 binding to HUVECs in a pre-confluent monolayer in response to VEGF-A165, VEGF-DΔNΔC, or $Mn^{2+}$ are shown in FIG. 11B. All treatments induced WOW-1 binding and binding was most evident at the cellular borders. To further investigate whether activated $\alpha_v\beta_3$ integrin forms a complex with VEGFR-2, HUVECs were induced with VEGF and stained with WOW-1 and VEGFR-2 antibody. Surprisingly on VEGF-stimulated EC, activated $\alpha_v\beta_3$ co-localized with VEGFR-2 on cell borders (FIG. 11C). Thus, our results establish that VEGFR-2-dependent activation of $\alpha_v\beta_3$ integrin leads to macromolecular interaction between $\alpha_v\beta_3$ integrin and the VEGF receptor-2 in endothelial cells.

Activated αVβ3 Integrin is Index for Enhanced Tumor Vasculature

To further emphasize whether αvβ3 integrin interact with VEGFR-2 on endothelial cells of proliferating blood vessel, we have selected biopsy specimens of human prostate carcinomas that express high expression of VEGF. Triple staining of serial tissue sections of the prostate tumors with WOW-1 antibodies (to localize activated $\alpha_v\beta_3$), with Abs against CD31 (to identify EC), and with Abs against VEGFR-2 (to localize VEGFR-2) was used (FIG. 12A). As in he in vitro studies presented above, activated αVβ3 co-localized with VEGFR-2 in vasculature of prostate carcinomas (FIG. 12A). The distribution of VEGFR-2 and WOW-1 staining was virtually identical in most of carcinoma samples (FIG. 12B). This result clearly indicated that activated αvβ3 integrin physically associated with VEGFR-2 on endothelial cells of proliferating blood vessels.

Next, we performed WOW-1 staining of normal prostate tissues to compare to prostate carcinomas. Based on CD31 staining, the prostate carcinoma tissue is characterized by 6-fold increase in vascular density compared to normal tissue (FIGS. 12 C and D). The vessels of normal prostate tissue were poorly stained with the WOW-1 antibody, whereas prostate tumor vessels were clearly WOW-1-positive, suggesting that activation of $\alpha_v\beta_3$ might serve as a marker of pathological angiogenesis. Quantification of WOW-1 density revealed a 2.7-fold increase in $\alpha_v\beta_3$ activation in prostate carcinomas compared to normal prostate tissues (FIG. 12E). Thus, quantification of αvβ3 integrin could be used as index for tumor angiogenesis. Thus, our in vivo analyses provide evidence that $\alpha_v\beta_3$ is activated on EC at sites of angiogenesis. Co-localization of activated $\alpha_v\beta_3$ with VEGFR-2 indicates a possible cross-talk between these receptors not only in vitro but also in vivo.

VEGFR-2/β3 Integrin Cross-Talk in EC

It was reported that knockouts of β3 and β5 subunits in mice resulted in upregulation of the expression level of VEGFR-2 on EC. However, as shown in FIGS. 13 A, B, and C, silencing of expression of β1, β3, or β5 integrin using siRNA had no effect on VEGFR-2 levels in EC. Thus, it is most likely that upregulation of VEGFR-2 in β3-null mice occurs during development as a compensatory mechanism due to the result of prolonged down-regulation of $\alpha_v\beta_3$ integrin. We also assessed how inhibition of expression of β subunits affected VEGFR-2 activation in EC. In control EC, treatment with VEGF induced substantial phosphorylation of VEGFR-2 (FIG. 14D). This response was not affected by silencing of β1 integrin (FIG. 14D). In contrast, ablation of β3 expression by a specific siRNA resulted in ~3-fold decrease of VEGFR-2 phosphorylation in response to VEGF. Silencing of the β5 subunit resulted in a modest decrease of phosphorylation VEGFR-2 (FIG. 14 D). Thus, it appears that β3, but not β1 or β5, integrin influenced VEGFR-2 activation on EC.

Next, we assessed whether activation of $\alpha_v\beta_3$ by externally added activating antibodies influenced activation of VEGFR-2 in response to VEGF. As shown in FIG. 14E, three different β3-specific activating antibodies, LIBS-1, AP-7.3, and CRC-54, augmented VEGFR-2 phosphorylation in VEGF-treated EC. In contrast, antibodies that blocked $\alpha_v\beta_3$ provided 2-fold inhibition of VEGFR-2 phosphorylation. Thus, not only expression but also activity of $\alpha_v\beta_3$ integrin appears to control VEGF-induced phosphorylation of VEGFR-2, demonstrating a functional cross-talk between these two receptors.

Example 3

Method: Angiogenesis Assay in Matrigel
Experimental Details

The effect of $\alpha_v\beta_3$/VEGFR2 complex inhibiting peptides in accordance with the present invention on angiogenic function was assessed by tube formation assay on the basement membrane matrix preparation. Six well plates were coated with 0.5 mL of Matrigel according to the manufacturer's instructions. HUVECs (Human Umbilical vascular endothelial cells) were detached from the tissue culture flasks using 20 mM EDTA. Cells were washed twice with sterile PBS and seeded on Matrigel-coated plates in combination of presence/absence of VEGF and inhibitory peptide. Cells were further incubated at 37° C. for 8 h. The tube formation was observed using an inverted phase contrast microscope (Leica) and photographs were taken from each well. Using ImagePro software, the degree of tube formation was quantified by measuring the length of tubes in random fields.

FIG. 14 illustrates (A) photographs of endothelial cell tube formation in a matrigel assay for endothelials cells subjected to VEGF, a peptide in accordance with the present invention, and VEGF in conjunction with a peptide in accordance with the present invention, and (B) a graph showing the results.

Results

The results were indicated that VEGF induced the endothelial cell tube formation by at least 450 μm/mm². Treatment of endothelial cells with these peptides also inhibited the tube formation at least by 50%. Even upon induction with VEGF treatment. These data clearly indicate that pre-phosphorylated beta 3 integrin cytoplasmic peptide prevent VEGF induced endothelial tube formation in vitro.

Comparative Example

Data showing the phosphorylation status of beta 3 integrin upon LM609 treatment (original antibody used to create vitaxin) is indicated in FIG. 15. Phosphorylation of beta 3 depends on the complex formation (this is a functional read-out). If phosphorylation still occurs, beta 3 integrin can still send a signal (in other words, the receptor is still operational). At the same time, its binding ability is completely blocked. Thus, we monitor integrin function at the different level. This set of data means that LM609 (vitaxin) blocks only ligand binding but not signaling. Comparison of this data with DiYF shows that phosphorylation occurs in response to VEGF and is a prerequisite for complex formation. One more time: complex formation and phosphorylation of beta 3 are inter-dependent events.

HUVEC cells were serum starved for 3 hours and further incubated with these antibodies for 2 hours at room temperature. Cells were induced with 20 ng/ml VEGF for 5 mins and analyzed for phosphorylation of beta3 integrin by Western blot analysis.

Example 4

Methods

Matrigel plug assays were performed in age- and sex-matched C57/Bl6 background mice. Each animal received an abdominal subcutaneous injection of 500 μL Matrigel mixed with VEGF (60 ng/mL), heparin (60 units/mL) and 50 mM of control (SEQ ID NO: 43)
(YGRKKRRQRRR GDTANNPL FKEATSTFT-COOH)

or beta-3 integrin cytoplasmic domain inhibitory peptide (SEQ ID NO: 44)
(YGRKKRRQRRR G DTANNPL Yp KEATSTFT-COOH).

After 7 days, the animals were euthanized and dissected. Matrigel plugs were removed and digested using 5 mL Drabkin reagent and neovascularization was assessed using a hemoglobin assay as per the manufacturer's protocol (FIG. 16).

Results

To examine the effect of beta-3 integrin cytoplasmic domain inhibitory peptide on angiogenesis we subcutaneously implanted VEGF-A-containing Matrigel with either 50 mM of control peptide (SEQ ID NO: 43)
(YGRKKRRQRRR G DTANNPL FKEATSTFT-COOH)

or with equal amount of beta-3 integrin cytoplasmic domain inhibitory peptide (SEQ ID NO: 44)
(YGRKKRRQRRR G DTANNPLYpKEATSTFT-COOH).

Angiogenic response was measured based on the amount of hemoglobin extracted from Matrigel. As shown in FIG. 17, the hemoglobin concentration was at least 3.5 fold lower in Matrigel plugs treated with beta-3 integrin cytoplasmic domain inhibitory peptide compared to control peptide containing Matrigel.

Example 5

Cell Adhesion Assay

To examine endothelial cell adhesion to various ECM proteins following inhibition of expression of specific integrin subunits, HUVECs were plated on various integrin ligand coated plates and ability of EC to adhere to the distinct extracellular matrix components were tested after administration of a control peptide (SEQ ID NO: 43)
(YGRKKRRQRRR G DTANNPL FKEATSTFT-COOH)

or with equal amount of beta-3 integrin cytoplasmic domain inhibitory peptide (SEQ ID NO: 44)
(YGRKKRRQRRR G DTANNPLYpKEATSTFT-COOH).

FIG. 18A shows that the inhibiting peptide had no effect on cell adhesion compared to a control peptide.

Endothelial Cell Migration

To examine the effect of the inhibiting peptide on endothelial cell migration, VEGF-induced migratory activity of endothelial cells was measured after administration of a control peptide (SEQ ID NO: 43)
(YGRKKRRQRRR G DTANNPL FKEATSTFT-COOH)

or with equal amount of beta-3 integrin cytoplasmic domain inhibitory peptide (SEQ ID NO: 44)
(YGRKKRRQRRR G DTANNPLYpKEATSTFT-COOH)

to the endothelial cells. FIG. 18B shows that the inhibiting peptide prevented endothelial cell migration and inhibited capillary formation compared to the control peptide.

Example 6

To examine the effect of cylic inhibiting peptides on mouse aortic ring angiogensis, thoracic aortas from WT mice were removed under aseptic conditions and spliced into 1 mm thick rings. Thoracic aortic rings were placed between two layers of growth factor depleted Matrigel and allowed to solidify at room temperature. Matrigels were administered VEGF and 50 μM control peptides or with equal amounts of inhibiting peptide 1 (RR cyclic (NPLXK) (SEQ ID NO: 39), disulfide bridge cycle), inhibiting peptide 2 (RR cyclic (NITXR) (SEQ ID NO: 40), disulfide bridge cycle), inhibiting peptide 3 (RRRKKRKRRR cyclic (NPLXK) (SEQ ID NO: 41), disulfide bridge cycle), and inhibiting peptide 4 (RRRKKRKRRR cyclic (NITXR) (SEQ ID NO: 42), disulfide bridge cycle), where X is γ-carboxyglutamic acid. Microvessel outgrowth was visualized by phase contrast microscopy and numbers of vessels growing from each aortic ring were counted and photographed every two days using Leica phase contrast microscope after 1 week. FIG. 19 shows inhibiting peptides 1-4 inhibited angiogenesis of the mouse aortic rings in the presence of VEGF Example 7

To examine the effect of beta-3 integrin cytoplasmic domain inhibitory peptides on angiogenesis we subcutaneously implanted VEGF-A-containing Matrigel with either 100 μM of control peptide or with equal amount of inhibiting peptide 1 (RR cyclic (NPLXK) (SEQ ID NO: 39), disulfide bridge cycle), inhibiting peptide 2 (RR cyclic (NITXR) (SEQ ID NO: 40), disulfide bridge cycle), inhibiting peptide 3 (RRRKKRKRRR cyclic (NPLXK) (SEQ ID NO: 41), disulfide bridge cycle), and inhibiting peptide 4 (RRRK-KRKRRR cyclic (NITXR) (SEQ ID NO: 42), disulfide bridge cycle), where X is γ-carboxyglutamic acid. Angiogenic response was measured based on the amount of hemoglobin extracted from Matrigel. As shown in FIG. 20, the hemoglobin concentration was at least 5 fold lower in Matrigel plugs treated with the inhibiting peptides compared to control peptide containing Matrigel.

Example 8

To the examine the effect of beta-3 integrin cytoplasmic domain inhibitory peptides on tumor progression we subcutaneously implanted tumors in mice and then treated the mice with either 100 μM of control peptide or with equal amount of inhibiting peptide 1 (RR cyclic (NPLXK) (SEQ ID NO: 7), disulfide bridge cycle), inhibiting peptide 2 (RR cyclic (NITXR) (SEQ ID NO: 8), disulfide bridge cycle), inhibiting peptide 3 (RRRKKRKRRR cyclic (NPLXK) (SEQ ID NO: 7), disulfide bridge cycle), inhibiting peptide 4 (RRRKKRKRRR cyclic (NITXR) (SEQ ID NO: 8), disulfide bridge cycle), inhibiting peptide 5 (RR linear (NPLXK) (SEQ ID NO: 7)); and inhibiting peptide 6 (RR linear (NITXR) (SEQ ID NO: 8)), where X is γ-carboxyglutamic acid. As shown in FIG. 21, the inhibiting peptides substantially reduced tumor progression compared to a control with the cyclic inhibiting peptide reducing tumor progression as measured in tumor volume by at least 10 times after 15 days.

Example 9

To the examine the effect of beta-3 integrin cytoplasmic domain inhibitory peptides on tumor progression we treated human melanoma cells (WM-164) with either 100 μM of control peptide or with equal amount of inhibiting peptide 07-240 (HIV-TAT-(NPLXK) (SEQ ID NO: 7)), inhibiting peptide 07-241 (HIV-TAT-(NPLDK) (SEQ ID NO: 9)), inhibiting peptide 07-243 (HIV-TAT-(NITXR) (SEQ ID NO: 8)), and inhibiting peptide 07-244 (HIV-TAT-(NITDR) (SEQ ID NO: 10)), where X is γ-carboxyglutamic acid. As shown in FIG. 22, the inhibiting peptides induced apoptosis in melanoma cells compared to a control.

It will be appreciated that all patents and publications disclosed in this application are incorporated by reference in their entirety.

Having described the invention, the following is claimed:

1. A pharmaceutical composition comprising a synthetic peptide, the peptide consisting of about 10 to about 50 amino acids and comprising an amino acid sequence substantially homologous to a portion of VEGFR2, wherein the amino acid sequence is selected from the group consisting of: SEQ ID NO: 18, SEQ ID NO: 19, SEQ ID NO: 20, SEQ ID NO: 21, SEQ ID NO: 22, SEQ ID NO:23, and SEQ ID NO: 24, the peptide inhibits interaction of $\alpha_v\beta_3$ integrin with VEGFR2.

* * * * *

UNITED STATES PATENT AND TRADEMARK OFFICE
CERTIFICATE OF CORRECTION

| | |
|---|---|
| PATENT NO. | : 9,592,269 B2 |
| APPLICATION NO. | : 14/937289 |
| DATED | : March 14, 2017 |
| INVENTOR(S) | : Tatiana Byzova et al. |

It is certified that error appears in the above-identified patent and that said Letters Patent is hereby corrected as shown below:

In the Specification

Column 1, Lines 12-15, delete "This invention was made with government support under Grant No. NIH Grant PPG HL073311 awarded by National institute of Health. The government has certain rights in the invention" and insert --This invention was made with government support under HL073311 awarded by the National Institutes of Health. The government has certain rights in the invention.--

Signed and Sealed this
Twentieth Day of March, 2018

Andrei Iancu
*Director of the United States Patent and Trademark Office*